(12) United States Patent
Peruzzi et al.

(10) Patent No.: US 10,308,939 B2
(45) Date of Patent: Jun. 4, 2019

(54) USE OF AN MIRNA TO REDUCE PROLIFERATION OF A CANCER CELL

(71) Applicant: Board of Supervisors of Louisiana State University and Agricultural and Mechanical College, Baton Rouge, LA (US)

(72) Inventors: Francesca Peruzzi, New Orleans, LA (US); Duane Jeansonne, New Orleans, LA (US)

(73) Assignee: BOARD OF SUPERVISORS OF LOUISIANA STATE UNIVERSITY, Baton Rouge, LA (US)

( * ) Notice: Subject to any disclaimer, the term of this patent is extended or adjusted under 35 U.S.C. 154(b) by 9 days.

(21) Appl. No.: 15/880,032

(22) Filed: Jan. 25, 2018

(65) Prior Publication Data

US 2018/0155726 A1   Jun. 7, 2018

Related U.S. Application Data

(60) Division of application No. 15/410,832, filed on Jan. 20, 2017, now abandoned, which is a continuation-in-part of application No. PCT/US2015/041266, filed on Jul. 21, 2015.

(60) Provisional application No. 62/026,800, filed on Jul. 21, 2014.

(51) Int. Cl.
*A61K 48/00* (2006.01)
*C07H 21/02* (2006.01)
*C07H 21/04* (2006.01)
*C12N 15/113* (2010.01)
*A61K 9/00* (2006.01)
*A61K 31/7125* (2006.01)

(52) U.S. Cl.
CPC ........ *C12N 15/1135* (2013.01); *A61K 9/0019* (2013.01); *A61K 31/7125* (2013.01); *C12N 15/113* (2013.01); *C12N 2310/141* (2013.01)

(58) Field of Classification Search
CPC .. C12N 15/113; C12N 2310/11; A61K 31/713
See application file for complete search history.

(56) References Cited

U.S. PATENT DOCUMENTS

2011/0105341 A1   5/2011   Semizarov et al.
2014/0147454 A1   5/2014   Chakraborty et al.

FOREIGN PATENT DOCUMENTS

WO   WO 2013/063544   5/2013
WO   WO 2014/179765   11/2014

OTHER PUBLICATIONS

Hayashi et al. p63RhoGEF-mediated formation of a single polarized lamellipodium is required for chemotactic migration in breast carcinoma cells. FEBS Lett. Mar. 18, 2013. vol. 587. No. 6. pp. 698:705.
Jeansonne et al. Differential Effects of MicroRNAs on Glioblastoma Growth and Migration. Genes. Mar. 2013. vol. 4. No. 1. pp. 46-64.
Collins. Spliceosomal RNA infrastructure: The network of splicing components and their regulation by miRNAs. Adv Exp Med Bioi. 2011. vol. 722. pp. 1-18.
Jeansonne et al., Anti-tumoral effects of miR-3189-3p in glioblastoma. J Bioi Chem. Mar. 27, 2015, vol. 290, No. 13, pp. 8067-8080.
Elbashir et al., The EMBO Journal, 2001, vol. 20, No. 23, pp. 6877-6881.

*Primary Examiner* — Amy H Bowman
(74) *Attorney, Agent, or Firm* — Baker Donelson

(57) ABSTRACT

A method is provided for decreasing at least one of the proliferation and the migration of a cancer cell comprising contacting a cancer cell with an effective amount of a pharmaceutically acceptable composition comprising a microRNA (miRNA) having a nucleotide sequence having at least 80% sequence similarity to the nucleotide sequence of miR-3189-3p derived from the miR-3189 mitron of the Growth Differentiation Factor 15 (GDF15) gene. The methods and compositions are advantageous for inhibiting proliferation and migration of, but not limited to, glioblastoma cells, melanoma cells, and breast cancer cells.

11 Claims, 26 Drawing Sheets

Specification includes a Sequence Listing.

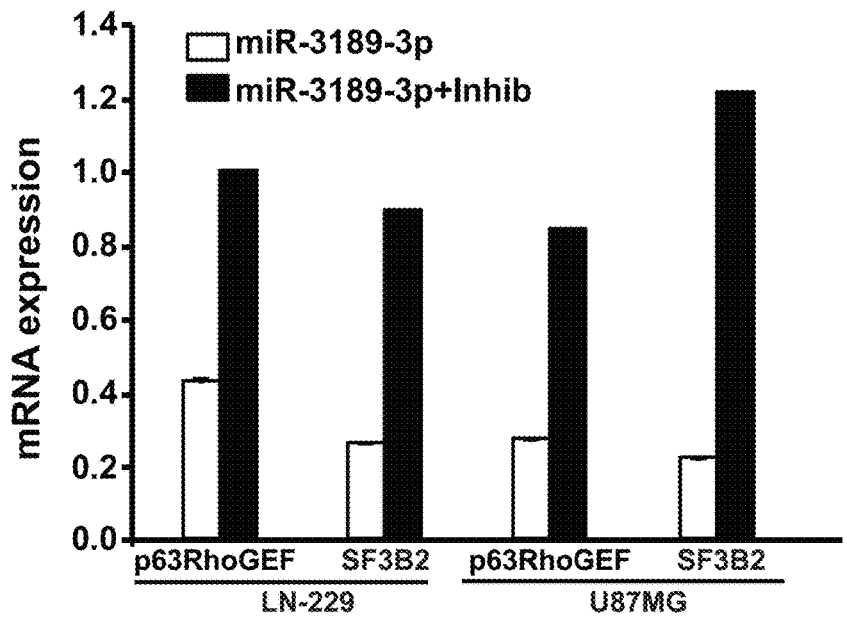
*Fig. 2A*
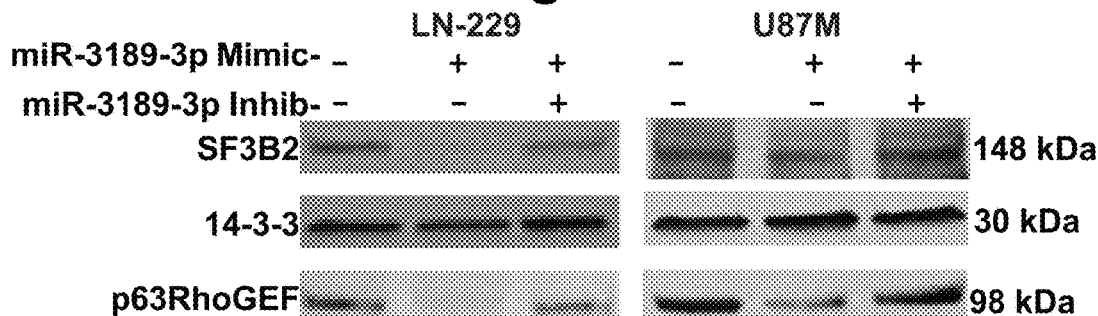
*Fig. 2B*
5' ACCUCUCCCGCAGUUCCCAAGGA Site 1 (79-86) SEQ ID NO: 16
         |||||||
3'     GAUGGGGUAGUCUGGGUUCCC miR-3189-3p SEQ ID NO: 2
5' UAAAUAAAGCUGUUUCCCAAGGA Site 2 (138-145) SEQ ID NO: 17
         |||||||
3'     GAUGGGGUAGUCUGGGUUCCC miR-3189-3p SEQ ID NO: 2
*Fig. 2C*

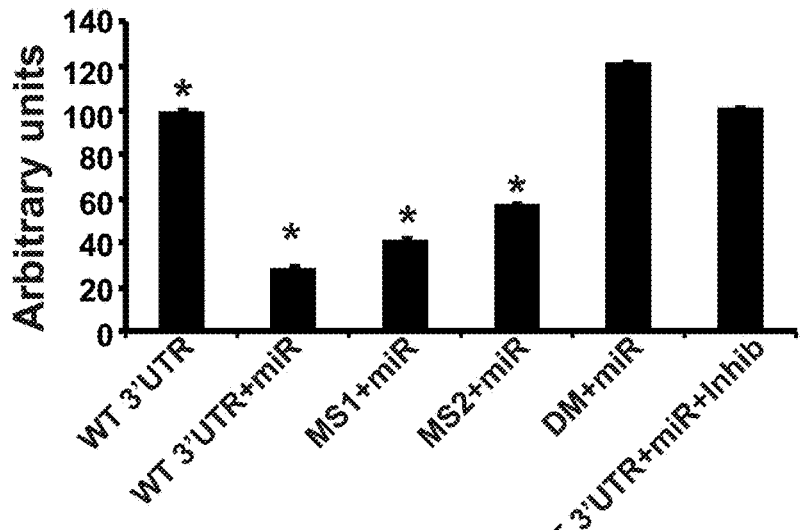
*Fig. 2D*
```
5' CUCAGCCGCCUAUUCCCAAGGA   Site 1 (44-51)   SEQ ID NO: 18
           |||||||
3'   GAUGGGGUAGUCUGGGUUCCC   miR-3189-3p SEQ ID NO: 2
5' AGGAGAACACCUAGACCCAAGGA   Site 2 (158-165) SEQ ID NO: 19
           |||||||
3'   GAUGGGGUAGUCUGGGUUCCC   miR-3189-3p SEQ ID NO: 2
5' AAGGACUUUUUUCUGCCCAAGGA   Site 3 (176-183) SEQ ID NO: 20
           |||||||
3'   GAUGGGGUAGUCUGGGUUCCC   miR-3189-3p SEQ ID NO: 2
```
*Fig. 2E*
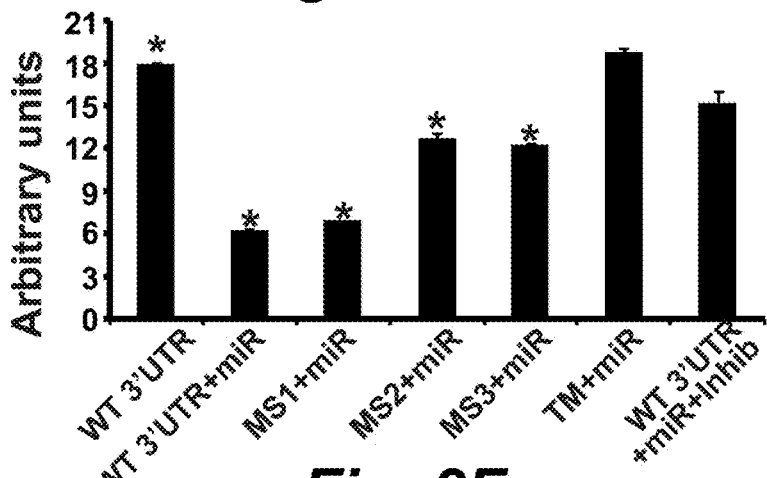
*Fig. 2F*

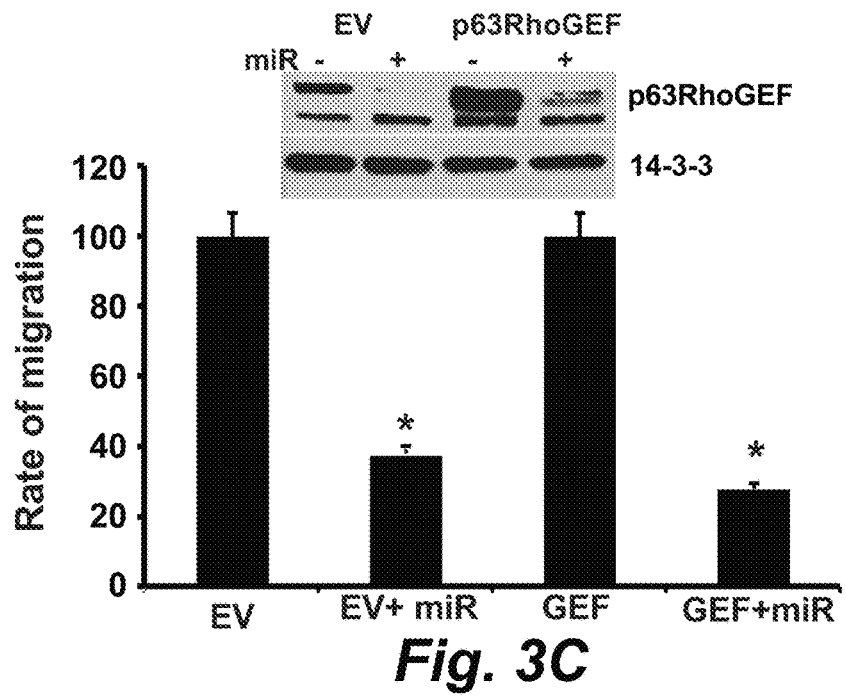
Fig. 3C
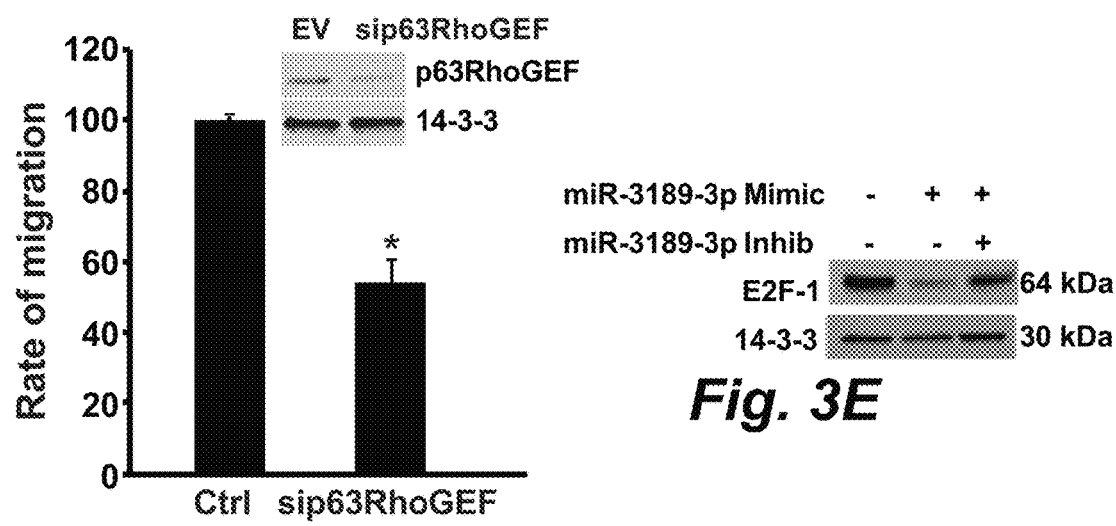
Fig. 3D
Fig. 3E

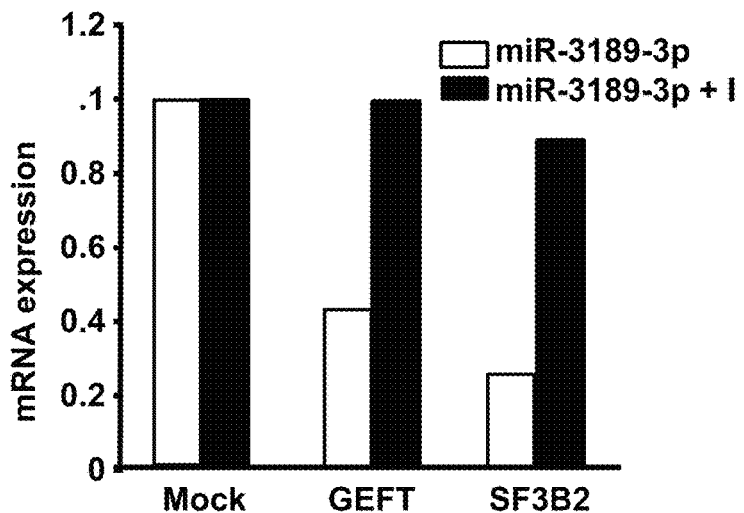
*Fig. 11B*
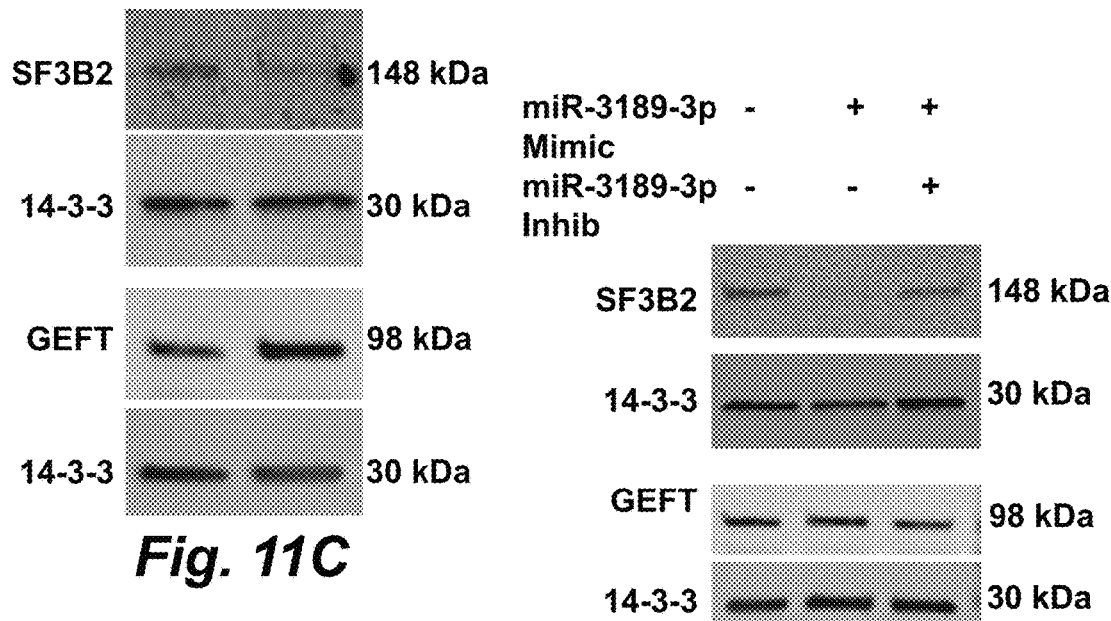
*Fig. 11C*
*Fig. 11D*

SEQUENCE LISTING

<160> NUMBER OF SEQ ID NOS: 22

<210> SEQ ID NO 1
<211> LENGTH: 73
<212> TYPE: RNA
<213> ORGANISM: Artificial sequence
<220> FEATURE:
<223> OTHER INFORMATION: miR-3189 microRNA

<400> SEQUENCE: 1
gccucaguug ccccaucugu gcccugggua ggaauauccu ggauccccuu gggucugaug     60
ggguagccga ugc                                                        73

<210> SEQ ID NO 2
<211> LENGTH: 21
<212> TYPE: RNA
<213> ORGANISM: Artificial sequence
<220> FEATURE:
<223> OTHER INFORMATION: miRNA-3189-p microRNA

<400> SEQUENCE: 2
cccuuggguc ugauggggua g                                               21

<210> SEQ ID NO 3
<211> LENGTH: 35
<212> TYPE: DNA
<213> ORGANISM: Artificial sequence
<220> FEATURE:

<223> OTHER INFORMATION: Forward primer for ORF of p63RhoGEF

<400> SEQUENCE: 3
ggtggaattc tgcagatatg cgggggggc acaaa        35

<210> SEQ ID NO 4
<211> LENGTH: 40
<212> TYPE: DNA
<213> ORGANISM: Artificial sequence
<220> FEATURE:
<223> OTHER INFORMATION: Reverse primer for ORF of p63RhoGEF

<400> SEQUENCE: 4
ccactgtgct ggatttacag ctcatcttca tccagcttgg        40

<210> SEQ ID NO 5
<211> LENGTH: 35
<212> TYPE: DNA
<213> ORGANISM: Artificial sequence
<220> FEATURE:
<223> OTHER INFORMATION: Forward primer for ORF of SF3B2

<400> SEQUENCE: 5
ggtggaattc tgcagatatg gcgacggagc atccc        35

<210> SEQ ID NO 6
<211> LENGTH: 47
<212> TYPE: DNA
<213> ORGANISM: Artificial sequence
<220> FEATURE:
<223> OTHER INFORMATION: Reverse primer for ORF of SF3B2

<400> SEQUENCE: 6
ccactgtgct ggatctaaaa cttgaactcc ttatatttct tgctgcc        47

<210> SEQ ID NO 7
<211> LENGTH: 30
<212> TYPE: DNA
<213> ORGANISM: Artificial sequence
<220> FEATURE:
<223> OTHER INFORMATION: Forward primer for 3'UTR of p63RhoGEF genomic
      sequence

<400> SEQUENCE: 7
ccgctcgagc tggtgaaaac catgggggtg        30

<210> SEQ ID NO 8
<211> LENGTH: 41
<212> TYPE: DNA
<213> ORGANISM: Artificial sequence
<220> FEATURE:
<223> OTHER INFORMATION: Reverse primer for 3'UTR of p63RhoGEF genomic
      sequence

<400> SEQUENCE: 8
ataagaatgc ggccgcgcag cctcggtgat ataacaaaac c        41

<210> SEQ ID NO 9
<211> LENGTH: 31
<212> TYPE: DNA
<213> ORGANISM: Artificial sequence
<220> FEATURE:
<223> OTHER INFORMATION: Forward primer for 3'UTR of SF3B2 genomic
      sequence

<400> SEQUENCE: 9

```
ccgctcgagt tcaagttttta ggtcccctca c                                         31
```

```
<210> SEQ ID NO 10
<211> LENGTH: 46
<212> TYPE: DNA
<213> ORGANISM: Artificial sequence
<220> FEATURE:
<223> OTHER INFORMATION: Reverse primer for 3'UTR of SF3B2 genomic
      sequence

<400> SEQUENCE: 10
ataagaatgc ggccgcggag gctcaggagt gttaaatatt catctc                          46
```

```
<210> SEQ ID NO 11
<211> LENGTH: 38
<212> TYPE: DNA
<213> ORGANISM: Artificial sequence
<220> FEATURE:
<223> OTHER INFORMATION: Forward primer for p63RhoGEF site 1 mutagenesis

<400> SEQUENCE: 11
tcagccgcct attcccttc cagcttcagg gcagtcct                                    38
```

```
<210> SEQ ID NO 12
<211> LENGTH: 46
<212> TYPE: DNA
<213> ORGANISM: Artificial sequence
<220> FEATURE:
<223> OTHER INFORMATION: Forward primer for p63RhoGEF site 2 mutagenesis

<400> SEQUENCE: 12
tggaggagaa cacctagacc cttccacttt tttctgccca aggaac                          46
```

```
<210> SEQ ID NO 13
<211> LENGTH: 46
<212> TYPE: DNA
<213> ORGANISM: Artificial sequence
<220> FEATURE:
<223> OTHER INFORMATION: Forward primer for p63RhoGEF site 3 mutagenesis

<400> SEQUENCE: 13
cccaaggact ttttctgcc cttccaacac agtttccttc agctcc                           46
```

```
<210> SEQ ID NO 14
<211> LENGTH: 50
<212> TYPE: DNA
<213> ORGANISM: Artificial sequence
<220> FEATURE:
<223> OTHER INFORMATION: Forward primer for SF3B2 site 1 mutagenesis

<400> SEQUENCE: 14
gaaccacctc tcccgcagtt cccttccact tgtcatttca tgttcttatt                      50
```

```
<210> SEQ ID NO 15
<211> LENGTH: 62
<212> TYPE: DNA
<213> ORGANISM: Artificial sequence
<220> FEATURE:
<223> OTHER INFORMATION: Forward primer for SF3B2 site 2 mutagenesis

<400> SEQUENCE: 15
gacctgtttt gtaaataaag ctgtttccct tccaaagaga tgaatattta acactcctga           60
gc                                                                          62
```

```
<210> SEQ ID NO 16
```

```
<211> LENGTH: 23
<212> TYPE: RNA
<213> ORGANISM: Artificial sequence
<220> FEATURE:
<223> OTHER INFORMATION: SF3B2 Site 1 (79-86)

<400> SEQUENCE: 16
accucucccg caguucccaa gga                                              23

<210> SEQ ID NO 17
<211> LENGTH: 23
<212> TYPE: RNA
<213> ORGANISM: Artificial sequence
<220> FEATURE:
<223> OTHER INFORMATION: SF3B2 Site 2 (138-145)

<400> SEQUENCE: 17
uaaauaaagc uguuucccaa gga                                              23

<210> SEQ ID NO 18
<211> LENGTH: 22
<212> TYPE: RNA
<213> ORGANISM: Artificial sequence
<220> FEATURE:
<223> OTHER INFORMATION: p63RhoGEF Site 1 (44-51)

<400> SEQUENCE: 18
cucagccgcc uauucccaag ga                                               22

<210> SEQ ID NO 19
<211> LENGTH: 23
<212> TYPE: RNA
<213> ORGANISM: Artificial sequence
<220> FEATURE:
<223> OTHER INFORMATION: p63RhoGEF Site 2 (158-165)

<400> SEQUENCE: 19
aggagaacac cuagacccaa gga                                              23

<210> SEQ ID NO 20
<211> LENGTH: 23
<212> TYPE: RNA
<213> ORGANISM: Artificial sequence
<220> FEATURE:
<223> OTHER INFORMATION: p63RhoGEF Site 3 (176-183)

<400> SEQUENCE: 20
aaggacuuuu uucugcccaa gga                                              23

<210> SEQ ID NO 21
<211> LENGTH: 27
<212> TYPE: RNA
<213> ORGANISM: Artificial sequence
<220> FEATURE:
<223> OTHER INFORMATION: miR-3189-5p

<400> SEQUENCE: 21
guugccccau cugugcccug gguagga                                          27

<210> SEQ ID NO 22
<211> LENGTH: 25
<212> TYPE: RNA
<213> ORGANISM: Artificial sequence
<220> FEATURE:
<223> OTHER INFORMATION: anti-miR-3189-39 mirVana
```

```
<400> SEQUENCE: 22
ugccccaucu gugcccuggg uagga                                                25
```

USE OF AN MIRNA TO REDUCE PROLIFERATION OF A CANCER CELL

CROSS REFERENCE TO RELATED APPLICATIONS

This application is a Divisional of U.S. patent application Ser. No. 15/410,832 filed Jan 20, 2017 entitled "A THERAPEUTIC OLIGONUCLEOTIDE FOR THE TREATMENT OF CANCER," which is a continuation-in-part of co-pending PCT Application No. PCT/US2015/041266, filed Jul. 21, 2015 and titled "A THERAPEUTIC OLIGONUCLEOTIDE FOR THE TREATMENT OF CANCER", where the PCT claims priority to and the benefit of U.S. Provisional Patent Application Ser. No. 62/026,800 filed on Jul. 21, 2014 and titled "A THERAPEUTIC OLIGONUCLEOTIDE FOR THE TREATMENT OF CANCER", both of which are herein incorporated by reference in their entireties.

STATEMENT ON FUNDING PROVIDED BY THE U.S. GOVERNMENT

This invention was made with Government support under contracts RO1 CA095518 and P20 GM103501 awarded by the National Institutes of Health. The government has certain rights in the invention.

FIELD OF THE DISCLOSURE

The present disclosure relates generally to a small molecule compound for reducing at least one of the proliferation and migration of a cancer cell. In particular, the present disclosure relates to the use of a microRNA oligonucleotide reducing at least one of the proliferation and migration of a glioblastoma cell, a melanoma cell, or a breast cancer cell.

INCORPORATION OF SEQUENCE LISTING

The entire contents of a paper copy of the "Sequence Listing" and a computer readable form of the sequence listing on diskette, containing the file named 2222272050_ST25.txt are herein incorporated by reference. The support for the sequences can be found throughout the specification.

BACKGROUND

Glioblastomas are deadly cancers characterized by rapid cell proliferation, high invasiveness, and resistance to radio- and chemotherapy (Nakada et al., (2007) *Cell. Mol. Life Sci.* 64: 458-478). Patients with this aggressive tumor, which accounts for nearly 50% of all adult brain tumors, have a median survival of approximately 15 months (Nagasawa et al., (2012) *Neurosurgery Clinics N. Am.* 23: 307-322). The standard treatment for glioblastoma involves invasive surgery and radiotherapy, which is often followed by chemotherapy with temolozomide (Hegi et al., (2005) *New Eng. J. Med.* 352: 997-1003). As the development of novel therapeutic treatments for glioblastoma are desperately needed, it is essential to understand the molecular mechanisms supporting growth and survival of this highly malignant and practically incurable brain tumor.

Triple negative breast cancer (TNBC) is an aggressive subtype of breast cancer characterized by the lack of estrogen receptor, progesterone receptor, and HER-2. Consequently, TNBC cannot be treated by the available hormone therapies and receptor targeted treatments. MYC, a regulatory gene involved in cell growth, metabolism, differentiation, and apoptosis, is disproportionately overexpressed in many TNBCs, making it a valuable therapeutic target.

MicroRNAs (miRNAs) are non-translated RNA species typically of 19 to 25 nucleotides in length whose function is to mediate post-transcription regulation of gene expression. miRNAs bind to the 3' untranslated region (3'UTR) of target messenger RNAs (mRNAs), resulting in translation inhibition or degradation of the mRNA transcript and subsequent reduction in protein production.

Clinically, specific miRNAs may serve as a therapeutic target or therapeutic agent depending on their role in human health and disease, a notion that is particularly relevant for the treatment of various cancers. In this regard, intense research is focused on inhibiting an overexpressed miRNA molecule or reintroducing the depleted miRNA molecule, respectively, for the treatment of various cancers. As a therapeutic agent, miRNAs are particularly promising as they are relatively cheap to synthesize, and because as their intrinsic stability confers a longer in vitro activity. In addition, since they are endogenously produced by the cells their expression can be triggered by different agents and/or molecular tools; therefore suggesting their use in combination with other anti-cancer drugs, such as fenofibrate.

SUMMARY

One aspect of the disclosure, therefore, encompasses embodiments of a method for decreasing at least one of the proliferation and the migration of a cancer cell, the method comprising contacting a cancer cell with an effective amount of a pharmaceutically acceptable composition comprising a microRNA (miRNA), wherein said miRNA has a nucleotide sequence having at least 80% sequence similarity to the nucleotide sequence SEQ ID NO: 2, thereby decreasing at least one of the proliferation and migration of the cancer cell as compared to a control.

In some embodiments of this aspect of the disclosure, the cancer cell can be a glial tumor cell, a melanoma cell, or a breast cancer cell.

In some embodiments of this aspect of the disclosure, the glial tumor cell can be an astrocytoma tumor cell, an ependymal tumor cell, a glioblastoma multiforme tumor cell, or a primitive neuroectodermal tumor cell. In some embodiments of this aspect of the disclosure, the glioblastoma multiforme can be located in the brain or the spinal cord of the subject.

In some embodiments of this aspect of the disclosure, the miRNA can reduce the expression of at least one of p63RoGEF and SF3B2 splicing factor in the cancer cell, or modulate the effect of MYC in the cancer cell.

In some embodiments of this aspect of the disclosure, the cancer cell can be an isolated cancer cell, a cultured cell, a cell in a tissue of an animal or human patient, or progeny thereof.

In embodiments of this aspect of the disclosure, the miRNA can have a nucleotide sequence having at least 85%, 90%, 93%, 95%, 96%, 97%, 98%, 99%, or 100% sequence similarity to the nucleotide sequence of SEQ ID NO: 2.

In some embodiments of this aspect of the disclosure, the miRNA can have the nucleotide sequence of SEQ ID NO: 2.

Another aspect of the disclosure encompasses embodiments of method for treating a cancer comprising administering to an animal or human subject in need thereof an effective amount of a pharmaceutically acceptable composition comprising a microRNA (miRNA), wherein said miRNA has a nucleotide sequence having at least 80% sequence similarity to the nucleotide sequence of SEQ ID NO: 2, thereby decreasing at least one of the proliferation and migration of the cancer cell as compared to a control.

In some embodiments of this aspect of the disclosure, the cancer can be a glial tumor, melanoma cell, or a breast cancer cell.

In some embodiments of this aspect of the disclosure, the glial tumor cell can be an astrocytoma tumor cell, an ependymal tumor cell, a glioblastoma multiforme tumor cell, or a primitive neuroectodermal tumor cell.

In some embodiments of this aspect of the disclosure, the glioblastoma multiforme can be located in the brain or the spinal cord of the subject.

In some embodiments of this aspect of the disclosure, the miRNA reduces the expression of at least one of p63RoGEF and SF3B2 splicing factor in the cancer cell, or modulates the effect of MYC in the cancer cell.

In some embodiments of this aspect of the disclosure, the miRNA can have a nucleotide sequence having at least 85%, 90%, 93%, 95%, 96%, 97%, 98%, 99%, or 100% sequence similarity to the nucleotide sequence of SEQ ID NO: 2.

In some embodiments of this aspect of the disclosure, the miRNA can have the nucleotide sequence of miR-3189-3p according to SEQ ID NO: 2.

In some embodiments of this aspect of the disclosure, the pharmaceutically acceptable composition can be administered to the animal or human subject intravenously, subcutaneously, or intratumorally.

In some embodiments of this aspect of the disclosure, the pharmaceutically acceptable composition can be formulated to deliver the miRNA across the blood-brain barrier or to deliver the miRNA as a nucleic acid expression product to the cells of the cancer Yet another aspect of the disclosure encompasses embodiments of a composition comprising an oligonucleotide capable of hybridizing under physiological conditions to a nucleotide sequence that is the complement of the nucleotide sequence SEQ ID NO: 2, or the complement thereof, and in an amount effective to reduce at least one of the proliferation and the migration of a cancer cell in a patient administered said composition, and a pharmaceutically acceptable carrier.

In some embodiments of this aspect of the disclosure, the oligonucleotide can have a nucleotide sequence having at least 90% similarity to the nucleotide sequence SEQ ID NO: 2.

In some embodiments of this aspect of the disclosure, the oligonucleotide can have a nucleotide sequence SEQ ID NO: 2.

In some embodiments of this aspect of the disclosure, the composition can further comprise a therapeutic agent therapeutically effective against the cancer cell.

In some embodiments of this aspect of the disclosure, the cancer cell can be a glioblastoma cell, a melanoma cell, or a breast cancer cell.

Still another aspect of the disclosure encompasses embodiments of a kit comprising at least one of: (a) reagents for preparation of samples from blood samples; (b) reagents for creating or synthesizing an miRNA oligonucleotide having at least 80% sequence similarity to the nucleotide sequence of SEQ ID NO: 2, wherein said reagents are in suitable container means, and wherein said reagents are packaged either in aqueous media or in lyophilized form, and instructions for employing the kit components for the synthesis or therapeutic use of the miRNA oligonucleotide in a patient in need thereof.

BRIEF DESCRIPTION OF THE DRAWINGS

Many aspects of the disclosure can be better understood with reference to the following drawings.

FIG. 1A illustrates the relative expression of miR-3189-3p (SEQ ID NO: 2) in controls, astrocytomas and glioblastomas (n=9/group).

FIG. 1B illustrates phase contrast images showing the morphology of LN-229 and U87MG cells following transfection with miR-3189-3p (SEQ ID NO: 2) or miR-3189-3p (SEQ ID NO: 2)+anti-miR-3189-3p (SEQ ID NO: 22) (miR-3189-3p+inhib). Images were acquired at 48 h post-transfection.

FIG. 1C illustrates cell proliferation assay performed 72 h post-transfection of the indicated cell lines with mock (ctrl), miR-3189-3p (SEQ ID NO: 2), or miR-3189-3p (SEQ ID NO: 2)+inhibitor and quantified using CellTiter 96 AQueous One Solution Cell Proliferation Assay® (MTS) reagent. Results are expressed as percent growth/mock-treated control.

FIG. 1D cell cycle analysis of LN-229 cells transfected with mock (ctrl), miR-3189-3p (SEQ ID NO: 2) and anti-miR-3189-3p (SEQ ID NO: 22) (Inhib). Cells were stained with Guava Cell Cycle reagent and cell cycle distribution (%) was quantified by flow cytometry using a FACSAria.

FIG. 1E illustrates cell cycle analysis of U87MG cells transfected with mock (ctrl), miR-3189-3p (SEQ ID NO: 2) and anti-miR-3189-3p (SEQ ID NO: 22) (Inhib). Cells were stained with Guava Cell Cycle reagent and cell cycle distribution (%) was quantified by flow cytometry using a FACSAria. Asterisks indicate statistically significant differences with $p<0.05$.

FIG. 1F illustrates representative images of a scratch assay to monitor migration of controls (mock-transfected) and miR-3189-3p (SEQ ID NO: 2) transfected LN-229 cells; original magnification 10×. Migration into the cell-free area was monitored by time-lapse imaging in a VivaView fluorescent microscope. The same experiment was performed in U87MG cells and data are shown below the images. Asterisks indicate statistically significant differences with $p<0.05$.

FIGS. 2A-2F illustrate that miR-3189-3p directly targets the 3'UTR sequences of SF3B2 and p63RhoGEF.

FIG. 2A is a graph illustrating the results of qRT-PCR showing expression of p63RhoGEF and SF3B2 mRNAs in cells transfected with miR-3189-3p (SEQ ID NO: 2), and cells transfected with miR-3189-3p (SEQ ID NO: 2)+anti-miR-3189-3p (SEQ ID NO: 22). Results are expressed as fold-change compared to mock-treated cells.

FIG. 2B illustrates Western blots for SF3B2 and p63RhoGEF proteins performed on lysates from LN-229 and U87MG cells transfected with mock, miR-3189-3p (SEQ ID NO: 2), or miR-3189-3p (SEQ ID NO: 2)+anti-miR-3189-3p (SEQ ID NO: 22) (Inhib) for 48 h.

FIG. 2C illustrates predicted binding sites for miR-3189-3p (SEQ ID NO: 2) in the SF3B2 3'UTR sequences. The bases mutated in the microRNA binding site are shown in italics.

FIG. 2D is a graph illustrating the results of luciferase assays of LN-229 cells co-transfected with psiCHECK2/SF3B2 3'UTR and the mutants in the miR-3189-3p (SEQ ID NO: 2) putative binding sites (MS1 and MS2) and miR-3189-3p (SEQ ID NO: 2)+/−anti-miR-3189-3p (SEQ ID NO: 22) (Inhib).

FIG. 2E illustrates predicted binding sites for p63RhoGEF 3'UTR sequences. The bases mutated in the microRNA binding site are shown in italics.

FIG. 2F is a graph illustrating the results of luciferase assays of LN-229 cells co-transfected with psiCHECK2/ p63RhoGEF 3'UTR and mutants (MS1, MS2 and MS3) and miR-3189-3p (SEQ ID NO: 2)+/−anti-miR-3189-3p (SEQ ID NO: 22) (Inhib). MS1-3 indicates specific microRNA binding site mutants; DM & TM indicate double- and triple-binding site mutants. Asterisks indicate statistically significant differences with p<0.05.

FIGS. 3A-3E illustrate that miR-3189-3p (SEQ ID NO: 2) regulates LN-229 cell growth and migration through the down-regulation of SF3B2 and p63RhoGEF.

Figure 3A:
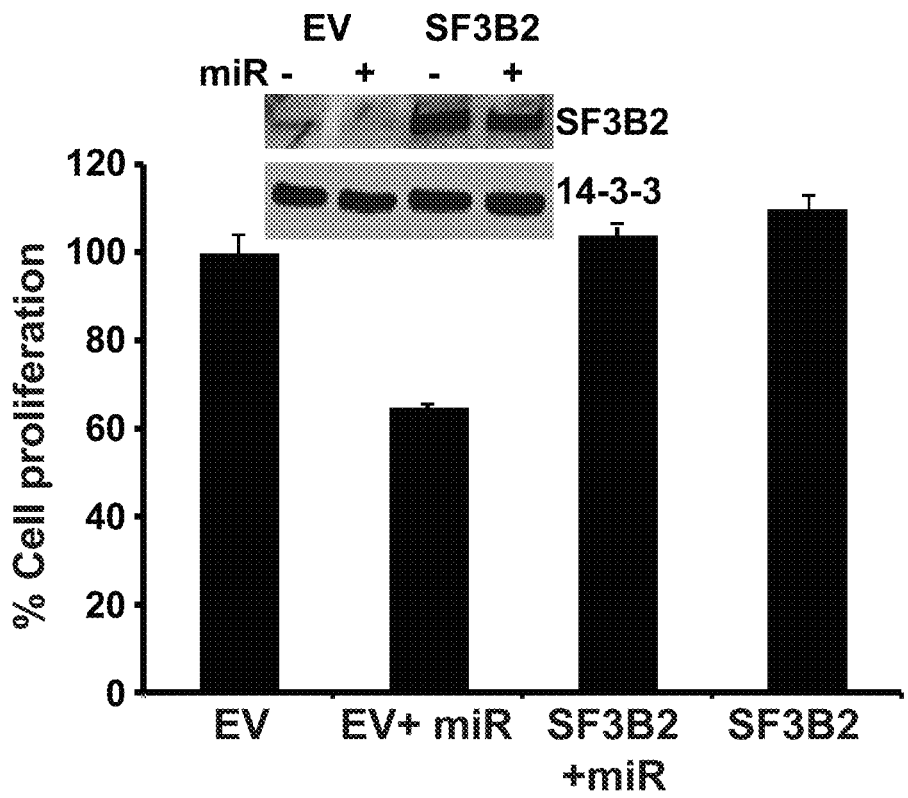

FIG. 3A is a graph illustrating the results of a cell growth assay performed 72 h after transient transfection of LN-229/pcDNA3.1 (EV) or LN-229/SF3B2 with miR-3189-3p (SEQ ID NO: 2). The inset shows levels of expression of SF3B2 in the indicated experimental conditions. Results are expressed as percent growth/mock-treated control.

Figure 3B:
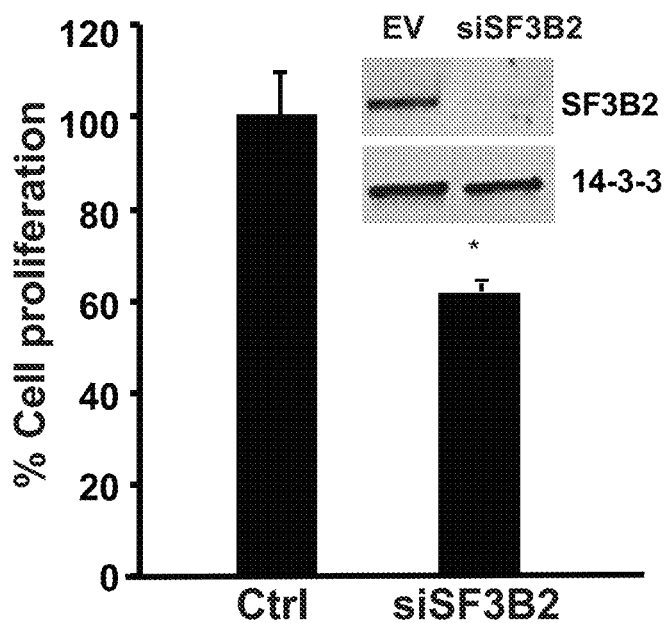

FIG. 3B is a graph illustrating the results of cell growth assay performed with mock-treated control or siSF3B2-treated LN-229 cells at 72 h post-transfection. Results are expressed as percent growth/mock-treated control. Statistically significant differences (p<0.05) are represented with an asterisk.

FIG. 3C is a graph illustrating the results of scratch assays to monitor migration of cells expressing the p63RhoGEF gene (GEF). The inset shows levels of expression of p63RhoGEF protein in the indicated conditions. Statistically significant differences (p<0.05) are represented with an asterisk.

FIG. 3D is a graph illustrating a plot of a scratch assay to monitor migration of mock-treated control or sip63RhoGEF-treated LN-229 cells. The inset shows levels of expression of p63RhoGEF protein in the indicated conditions. Statistically significant differences (p<0.05) are represented with an asterisk.

FIG. 3E illustrates Western blots for E2F-1 protein expression performed on lysates from cells transfected with mock, miR-3189-3p (SEQ ID NO: 2), or miR-3189-3p (SEQ ID NO: 2)+anti-miR-3189-3p (SEQ ID NO: 22) (Inhib). 14-3-3ζ antibody was used to show equal loading of cellular lysates. Statistically significant differences (p<0.05) are represented with an asterisk.

FIGS. 4A-4G illustrate that biophotonic measurements of orthotopic GBM xenografts in vivo show significant tumor suppressor activity of miR-3189-3p (SEQ ID NO: 2).

Figure 4A:
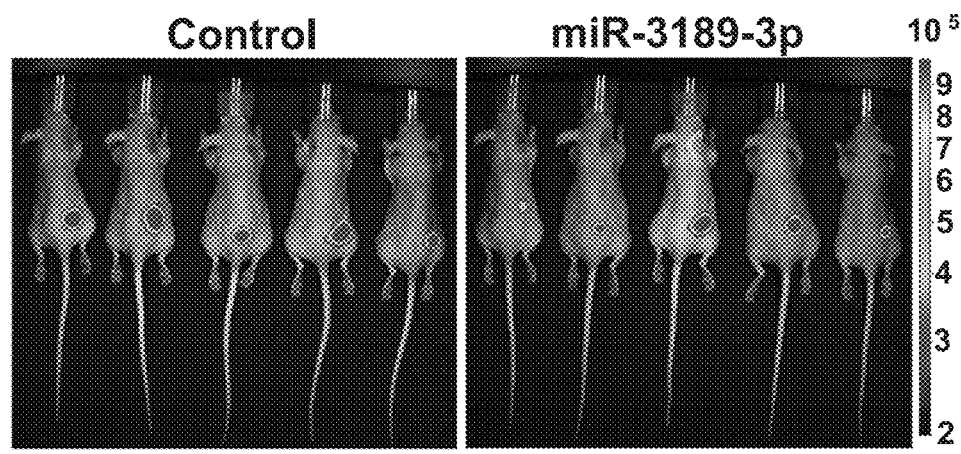

FIG. 4A illustrates fluorescent images of pmCherry/LN-229 cells mock-transfected (control) or transfected with miR-3189-3p (SEQ ID NO: 2) implanted subcutaneously in nude mice (n=5/group) (p<0.05).

Figure 4B:
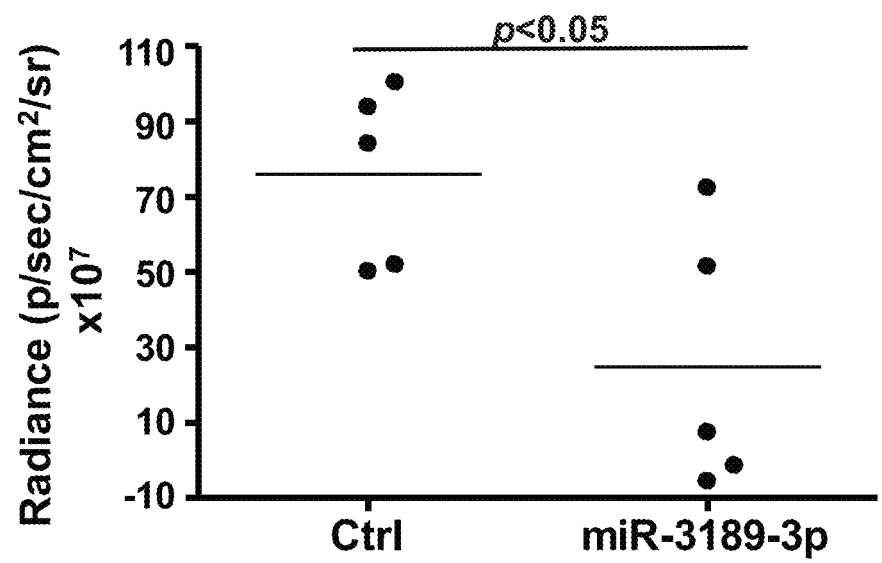

FIG. 4B illustrates a plot of tumor burden 3 weeks post-injection with control or miR-3189-3p (SEQ ID NO: 2)-transfected LN-229-mCherry cells. Relative fluorescence values are represented as photon flux per second, square centimeter and steradian (p/sec/cm²/sr).

Figure 4C:
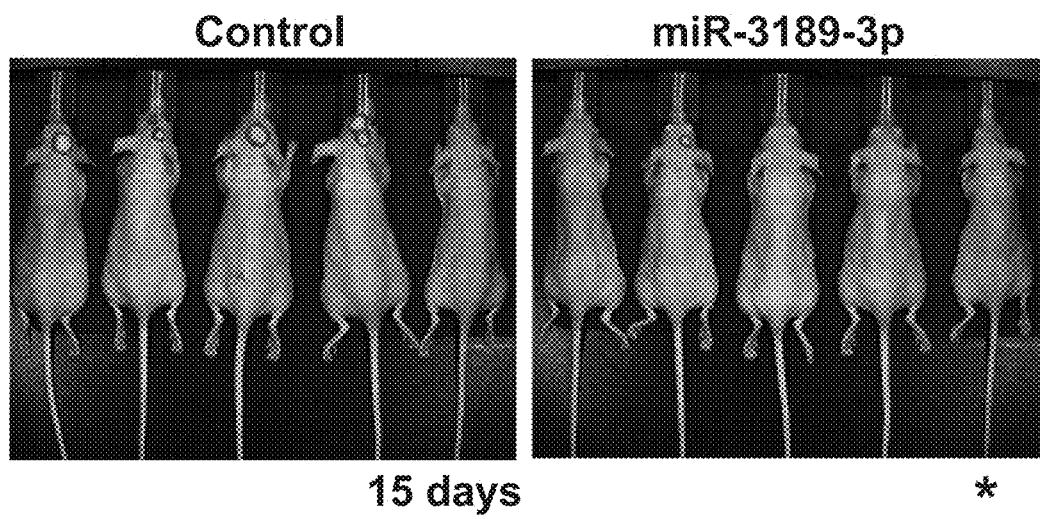

FIG. 4C illustrates luciferase/U87MG cells mock-transfected (control) or transfected with miR-3189-3p (SEQ ID NO: 2) and injected intracranially in nude mice (n=5/group). Images were taken after 15 days.

Figure 4D:
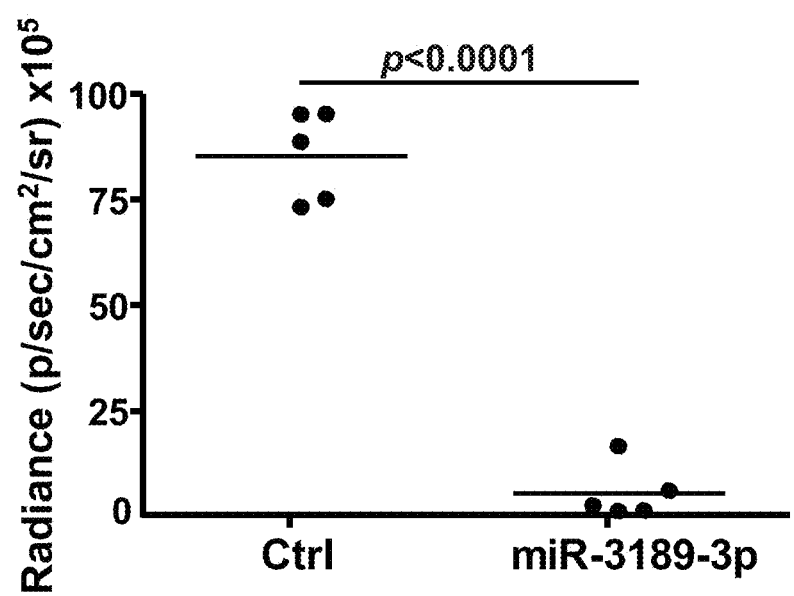

FIG. 4D illustrates luciferase/U87MG cells mock-transfected (control) or transfected with miR-3189-3p (SEQ ID NO: 2) were injected intracranially in nude mice (n=5/group). Relative plots of radiance after 15 d are shown.

Figure 4E:
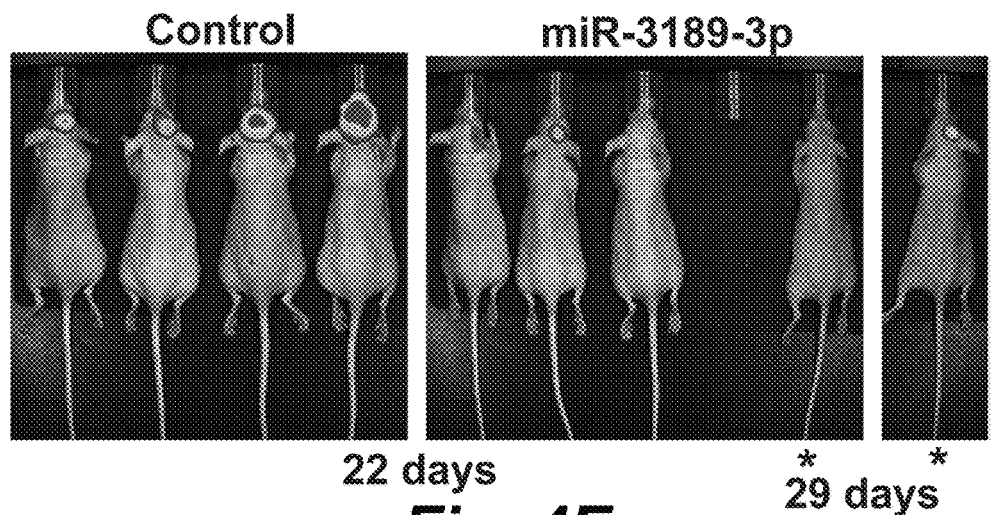

FIG. 4E illustrates luciferase/U87MG cells mock-transfected (control) or transfected with miR-3189-3p (SEQ ID NO: 2) were injected intracranially in nude mice (n=5/group). Images were taken after 22 days. The asterisks indicate the same mouse at day 29. The mouse missing in the miR-3189-3p (SEQ ID NO: 2) group at day 21 died of tumor-unrelated reasons.

Figure 4F:
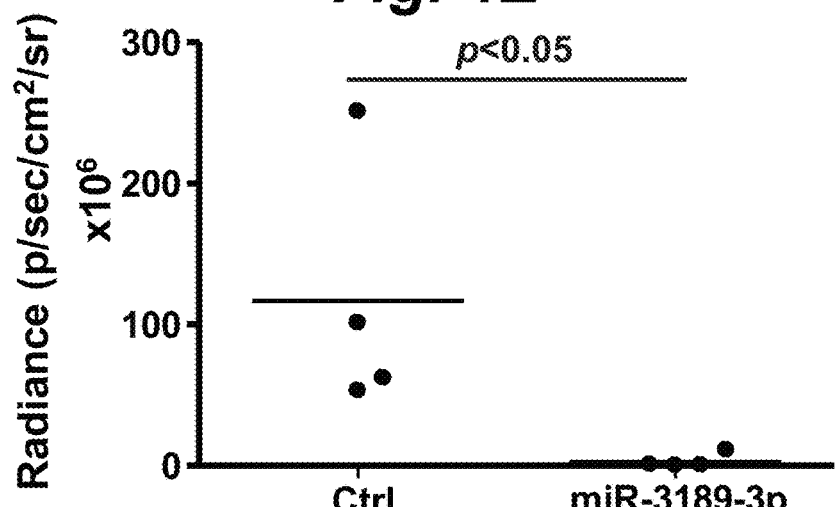

FIG. 4F is a graph illustrating the results of luciferase/U87MG cells mock-transfected (control) or transfected with miR-3189-3p (SEQ ID NO: 2) injected intracranially in nude mice (n=5/group). Images were taken after 22 days. Relative plots of radiance after 22 d are shown.

Figure 4G:
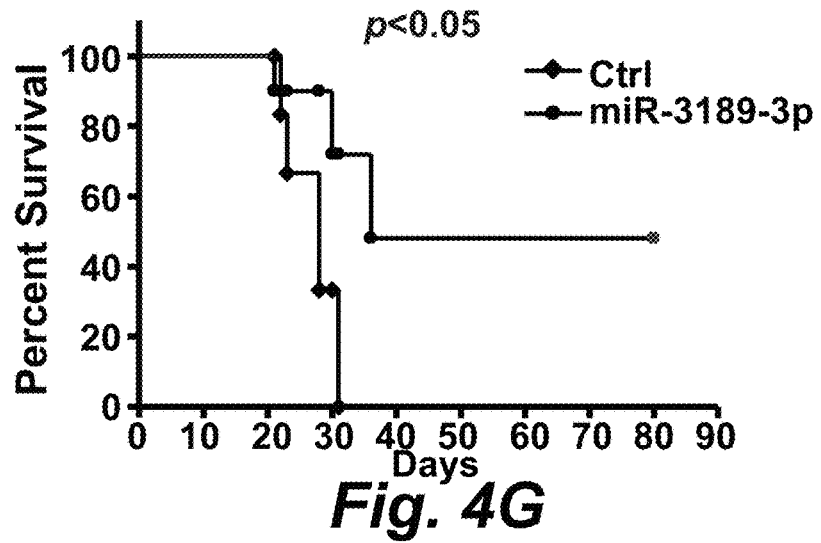

FIG. 4G illustrates Kaplan-Meier curves comparing mice bearing mock-transfected (ctrl) or miR-3189-3p (SEQ ID NO: 2)-transfected luciferase/U87MG cells. Statistical analysis reveals significantly longer survival (p<0.05) of mice injected with miR-3189-3p (SEQ ID NO: 2) transfected cells.

FIGS. 5A-5D illustrate the evaluation of GDF15, SF3B2, and p63RhoGEF mRNAs in clinical samples.

Figure 5A:
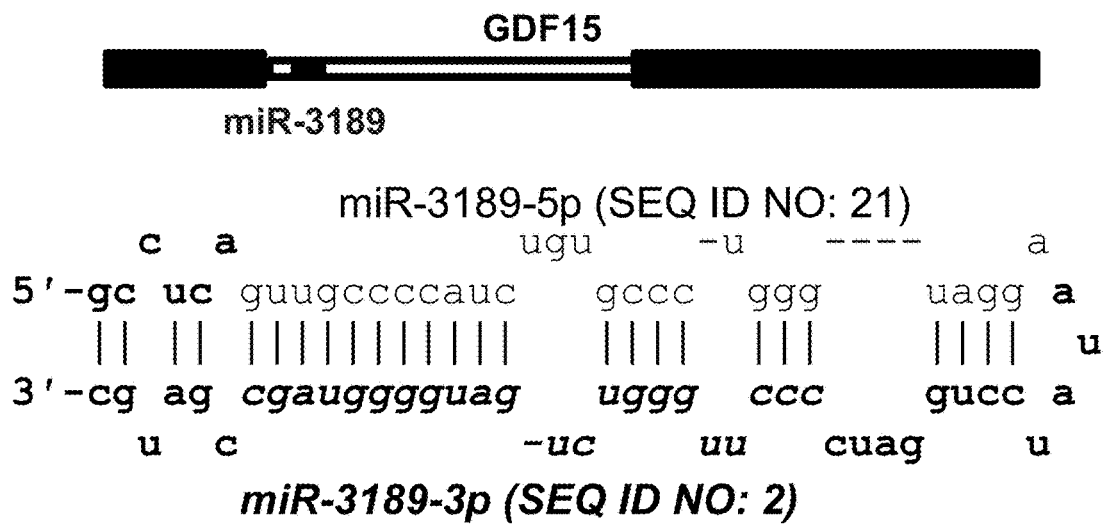

FIG. 5A illustrates a schematic of the human GDF15 gene encoding miR-3189 (SEQ ID NO: 1) within the exon and of the stem-loop structure of miR-3189 containing -3p and -5p mature microRNAs (SEQ ID Nos: 2 and 21, respectively). Note that this location arrangement is typical of mirtrons.

Figure 5B:
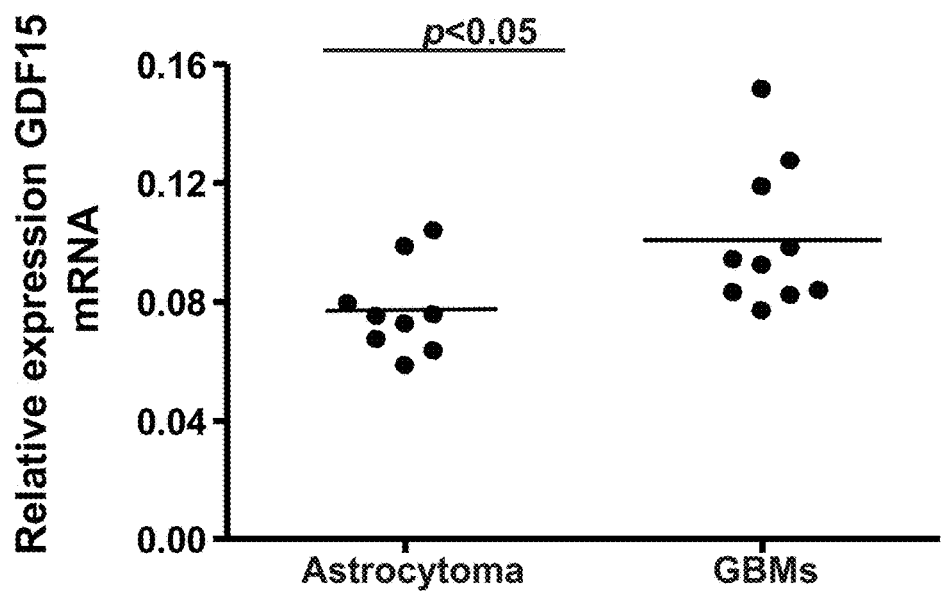

FIG. 5B illustrates a plot showing the greater expression of GDF15 mRNA in human astrocytoma and glioblastoma clinical samples relative to control brain samples, calculated as 1/ΔCt. T-test results (p-values) are shown in the graphs.

Figure 5C:
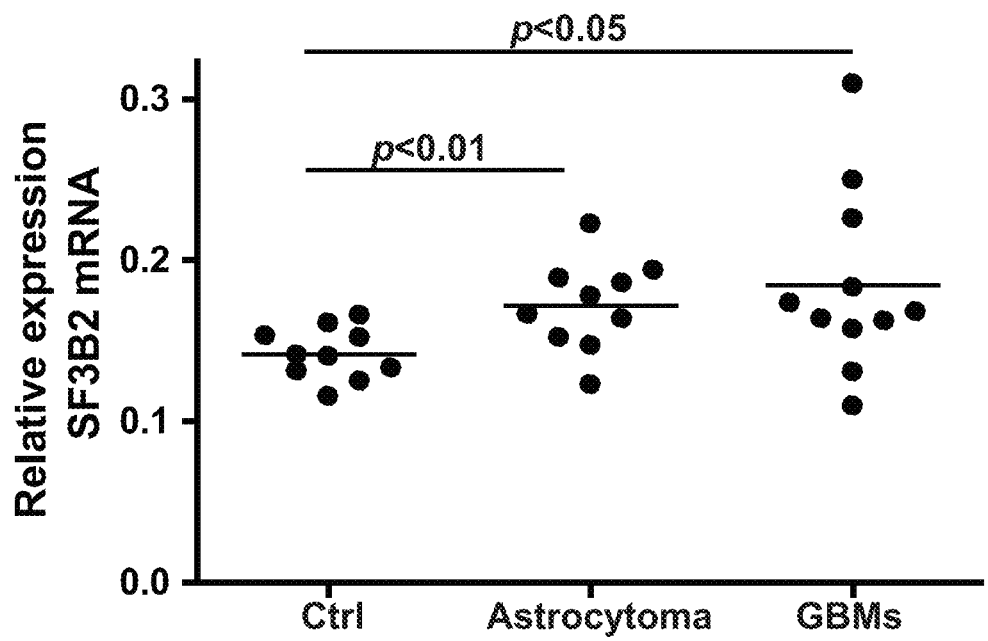

FIG. 5C illustrates the relative expression of SF3B2 mRNA in human astrocytoma and glioblastoma clinical samples, calculated as 1/ΔCt. Note that GDF15 mRNA was undetectable in control brain samples. T-test results (p-values) are shown in the graphs.

Figure 5D:
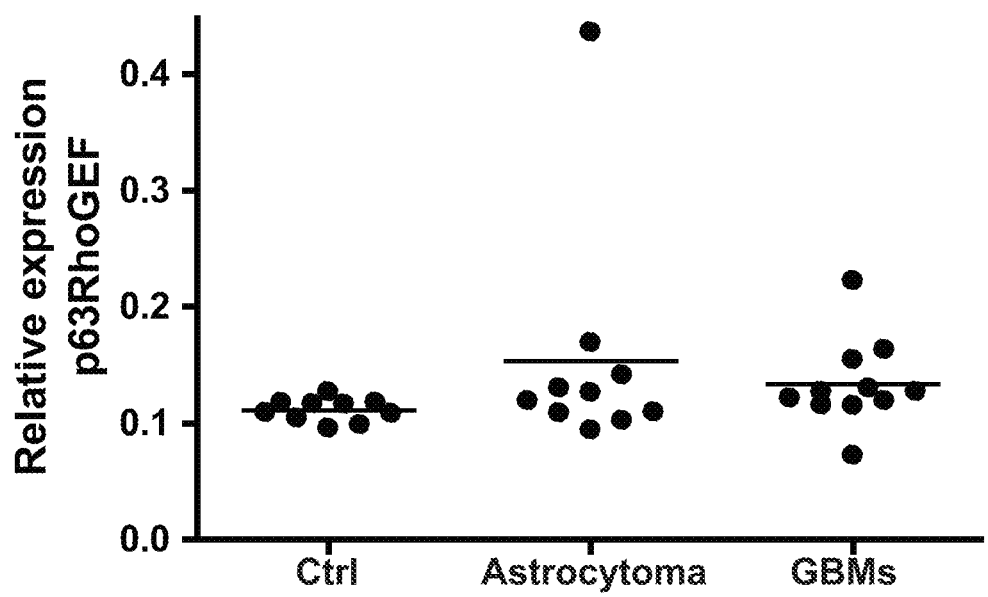

FIG. 5D illustrates the relative expression of p63RhoGEF mRNA in human astrocytoma and glioblastoma clinical samples, calculated as 1/ΔCt. Note that GDF15 mRNA was undetectable in control brain samples. T-test results (p-values) are shown in the graphs.

FIGS. 6A-6E illustrate that fenofibrate treatment up-regulates GDF15 and miR-3189-3p (SEQ ID NO: 2) expression in LN-229 and U87MG cells.

Figure 6A:
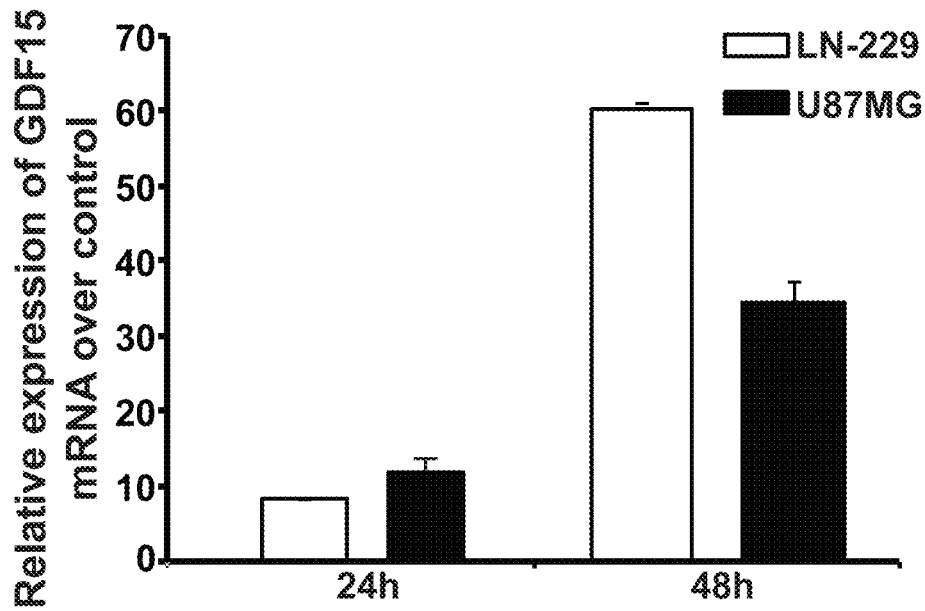

FIG. 6A illustrates real-time PCR to detect GDF15 mRNA expression at the indicated time points after fenofibrate treatment. Results are expressed as fold-change ($2^{-\Delta\Delta Ct}$ method) of the mRNA in fenofibrate-treated LN-229 cells compared to untreated (p<0.05).

Figure 6B:
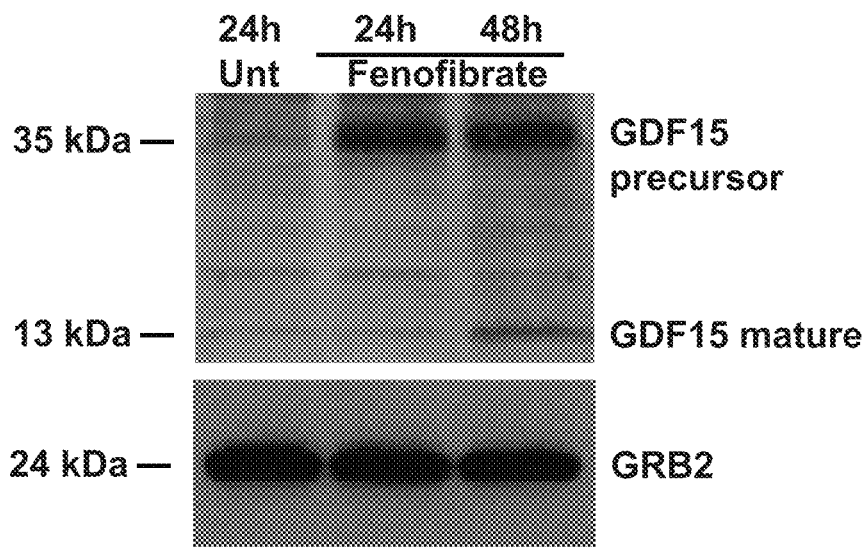
Figure 6C:
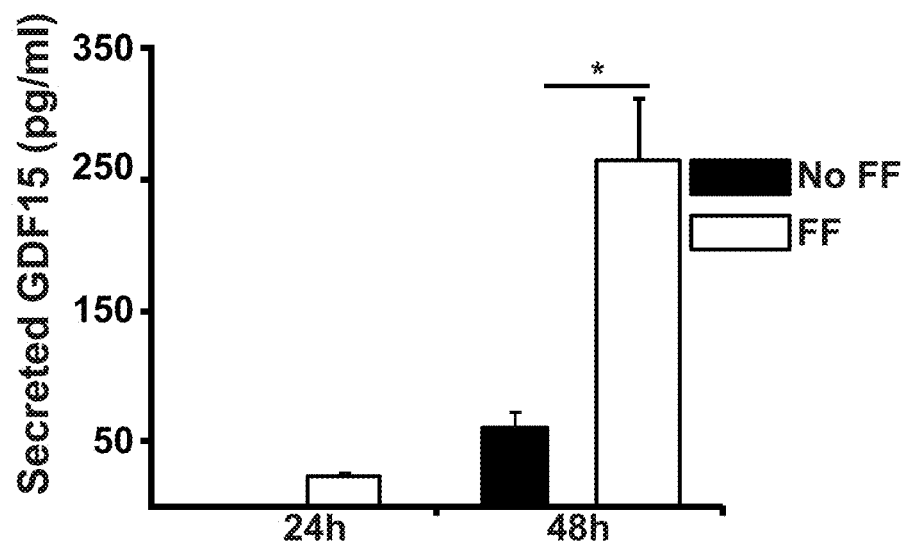

FIG. 6B illustrates mature and precursor GDF15 proteins detected by Western blots produced under the same experimental conditions as in FIG. 6A. GRB2 antibody was used to show equal loading of cellular lysates FIG. 6C illustrates the use of ELISA to detect secreted mature (active) GDF15 protein in the culturing medium obtained from LN-229 cells treated with fenofibrate (FF) and control (no FF). The data represent change in GDF15 levels in medium from fenofibrate-treated cells compared to untreated. All the differences in expression levels were statistically significant (p<0.05).

Figure 6D:
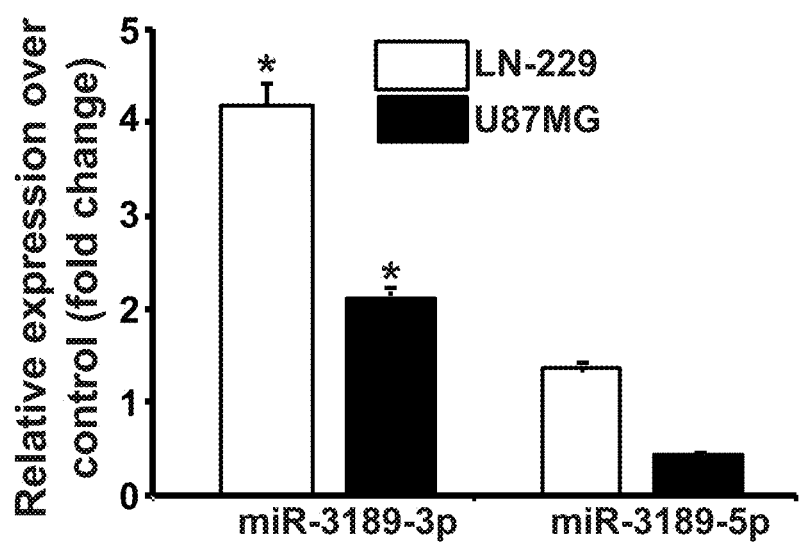

FIG. 6D illustrates the relative expression of miR-3189-3p (SEQ ID NO: 2) and miR-3189-5p (SEQ ID NO: 21) in LN-229 and U87MG cells treated for 48 h with fenofibrate. A fold-change of less than 2 means unchanged levels compared to controls. Only those with the asterisk had a p<0.05 when compared to controls.

Figure 6E:
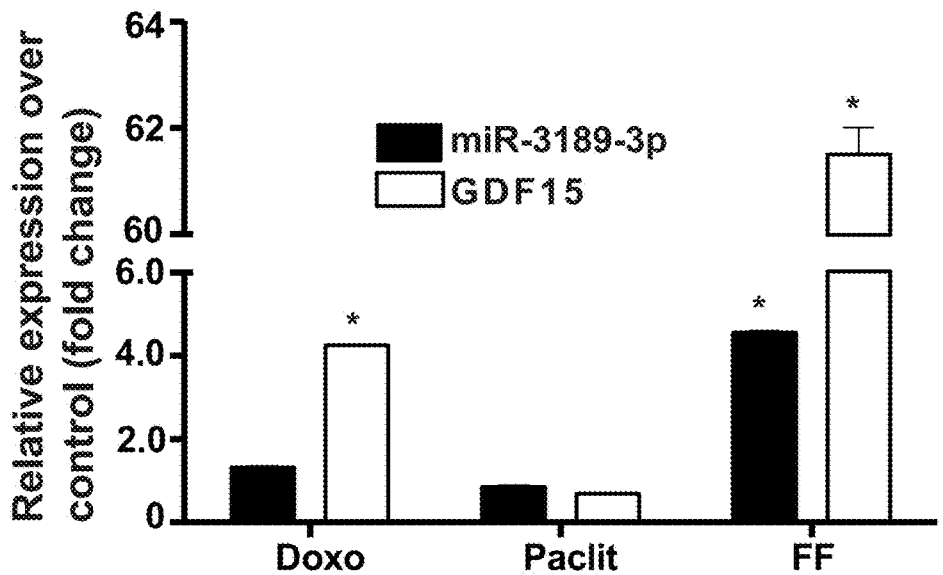

FIG. 6E illustrates a bar graph representing relative expression of GDF15 and miR-3189-3p (SEQ ID NO: 2) in LN-229 cells treated with doxorubicin (Doxo), paclitaxel (Paclit) and fenofibrate (FF) for 48 h. A fold-change <2 means unchanged levels compared to controls. Only those with the asterisk had a p<0.05 when compared to controls.

FIGS. 7A-7D illustrate that MiR-3189-3p is up-regulated and incorporated into the RNA-induced silencing complex (RISC) in cells treated with fenofibrate.

Figure 7A:
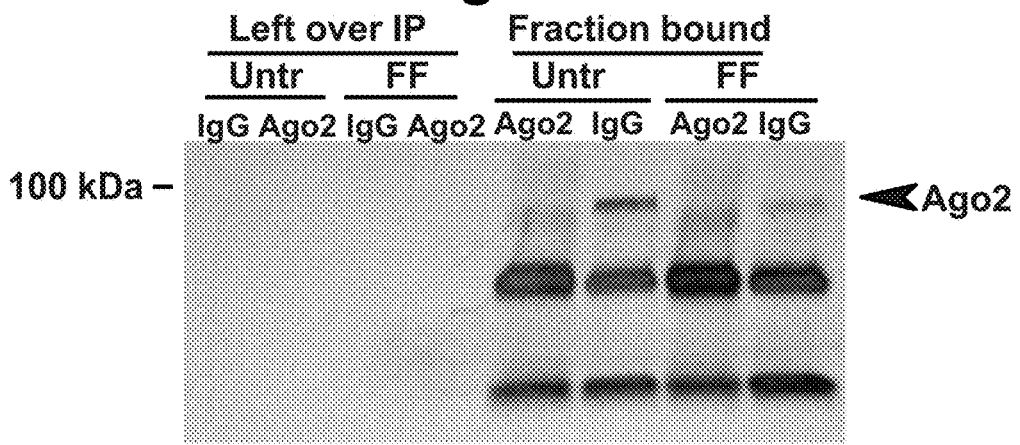

FIG. 7A illustrates a Western blot to detect Ago2 after immunoprecipitation of lysates obtained from untreated and fenofibrate-treated cells. "Left over IP" represents the fraction of lysates obtained after overnight incubation with Ago2 antibody or the control isotype IgG, and is used as negative control.

Figure 7B:
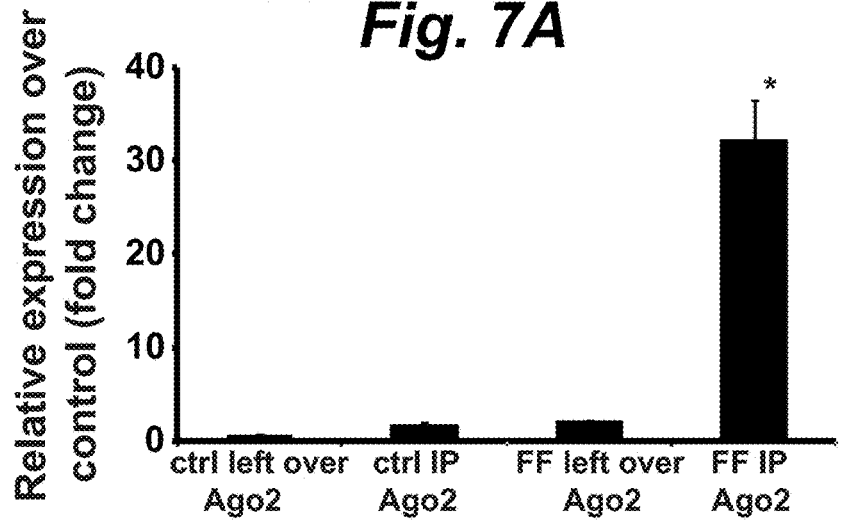

FIG. 7B illustrates real-time PCR to detect miR-3189-3p (SEQ ID NO: 2). Results are expressed as fold-change of the microRNAs in fenofibrate-treated cells (FF) compared to untreated. The enrichment of microRNAs or mRNAs in RISC was calculated according to the formula $2^{-(CtAgo2-CtIgG)}$ and normalized over RNU6B.

Figure 7C:
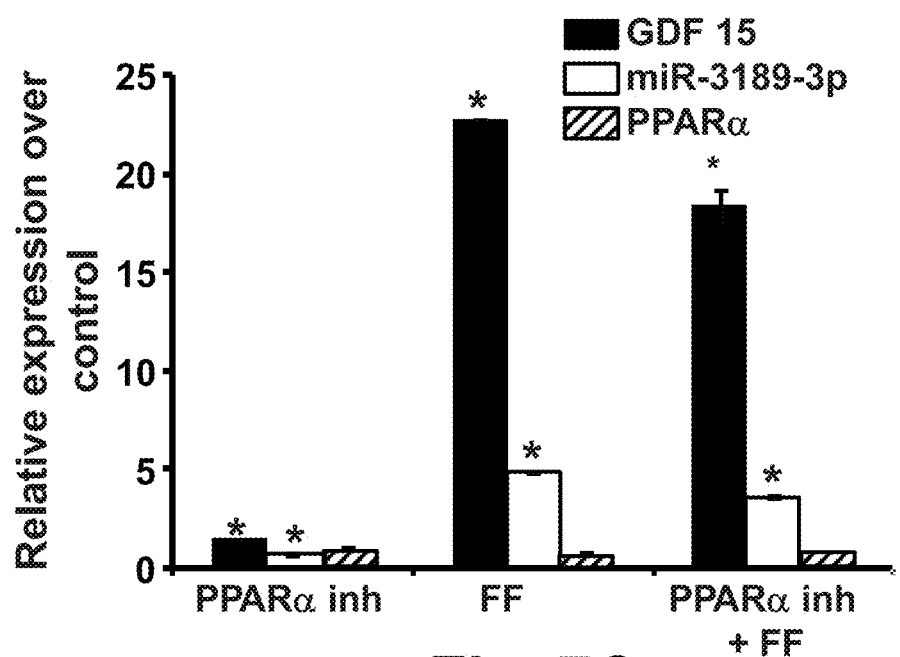

FIG. 7C illustrates relative expression of GDF15 in the indicated conditions (treatments and transfections) compared to controls. Asterisks indicate statistically significant differences in the indicated conditions compared to the respective controls (p<0.05).

Figure 7D:
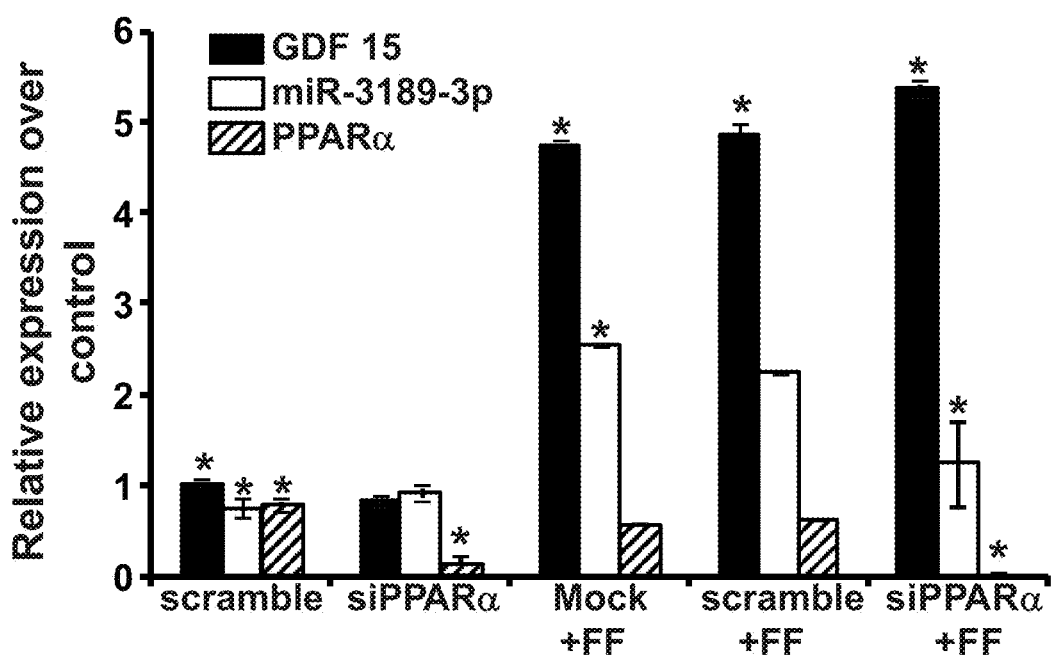

FIG. 7D illustrates relative expression of miR-3189-3p (SEQ ID NO: 2) in the indicated conditions (treatments and transfections) compared to controls. Asterisks indicate statistically significant differences in the indicated conditions compared to the respective controls (p<0.05).

Figure 8A:
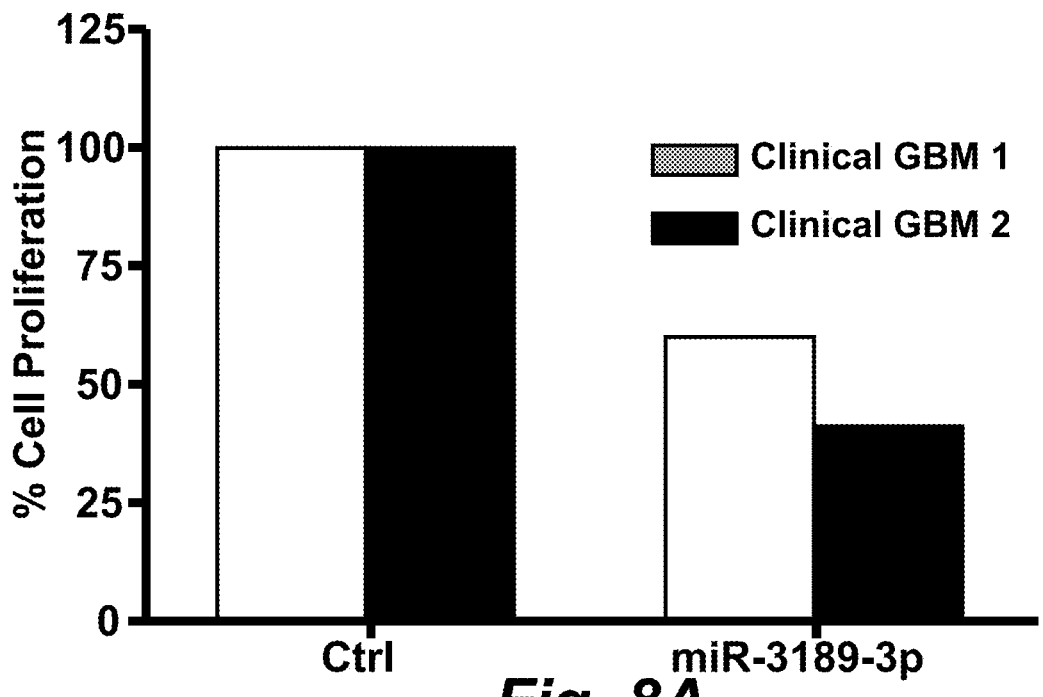
Figure 8B:
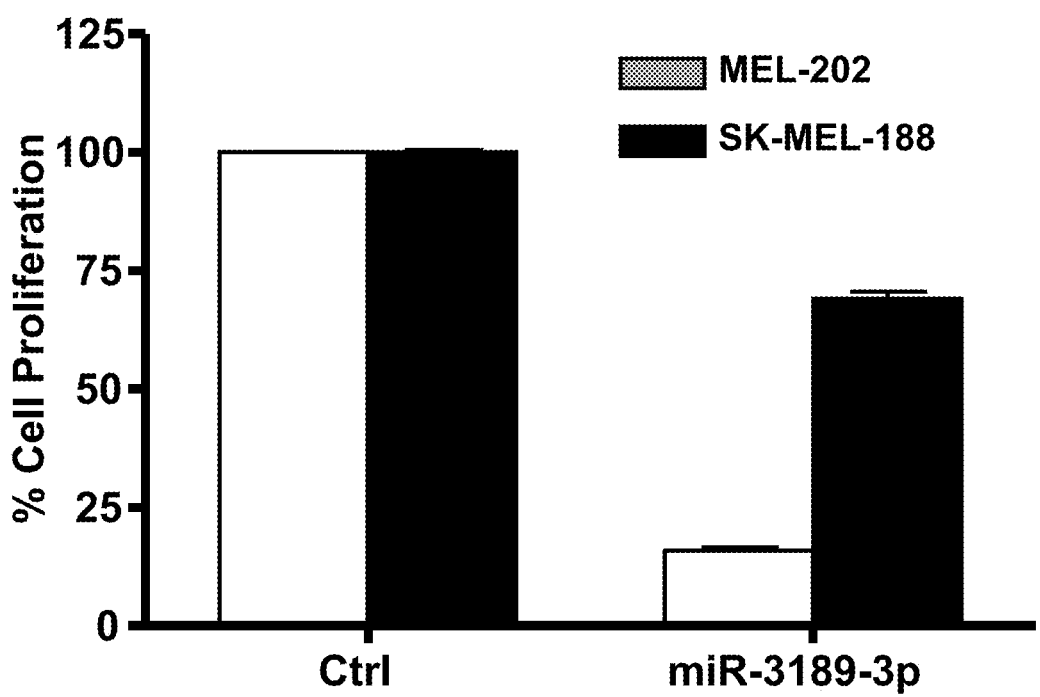

FIGS. 8A-8B illustrate the impairment of cell proliferation by miR-3189-3p (SEQ ID NO: 2) in primary GBM tumors and in melanoma.

FIG. 8A is a graph illustrating the results of a cell proliferation assay of clinical GBM cells transfected with control or miR-3189-3p (SEQ ID NO: 2).

FIG. 8B is a graph illustrating the results of a cell proliferation assay of melanoma cell lines transfected with control or miR3189-3p (SEQ ID NO: 2).

Figure 9:
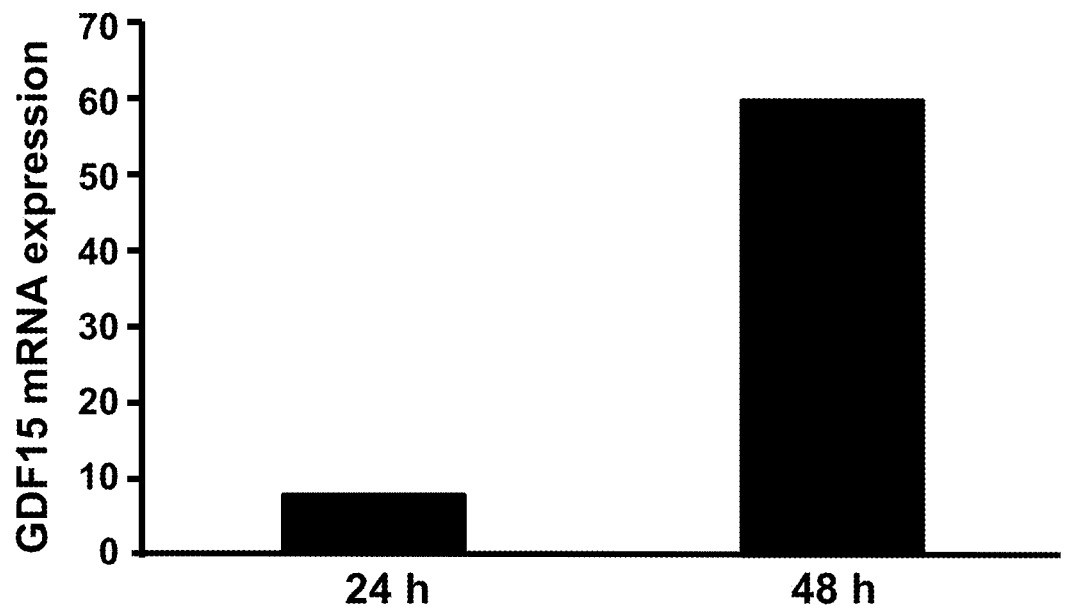

FIG. 9 illustrates that fenofibrate treatment up-regulates GDF15 mRNA and protein expression in LN-229 cells. Real-time PCR was used to detect GDF15 mRNA expression at the indicated time points after fenofibrate treatment. Results are expressed as fold-change ($2^{-\Delta\Delta Ct}$ method) of the mRNA in fenofibrate-treated LN-229 cells compared to untreated.

Figure 10A:
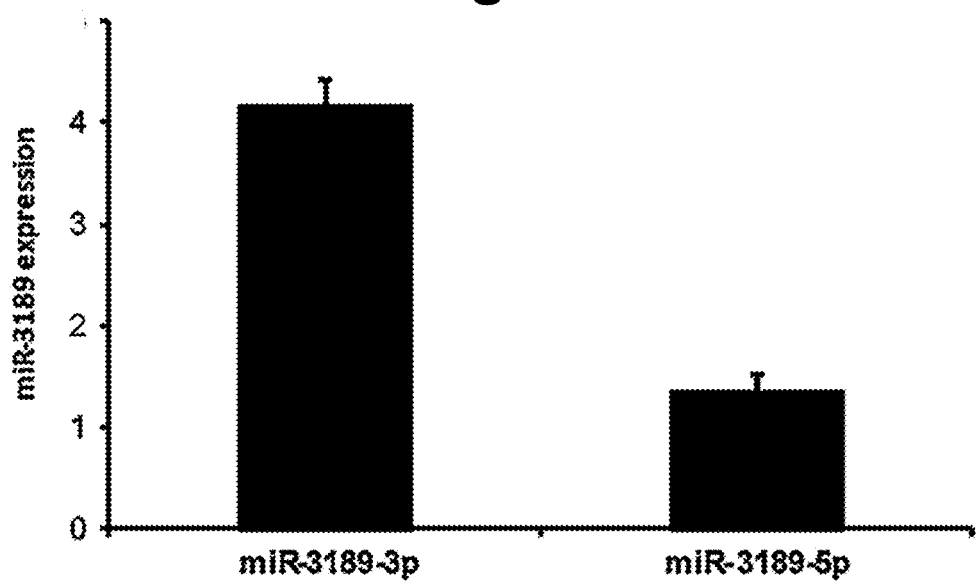
Figure 10B:
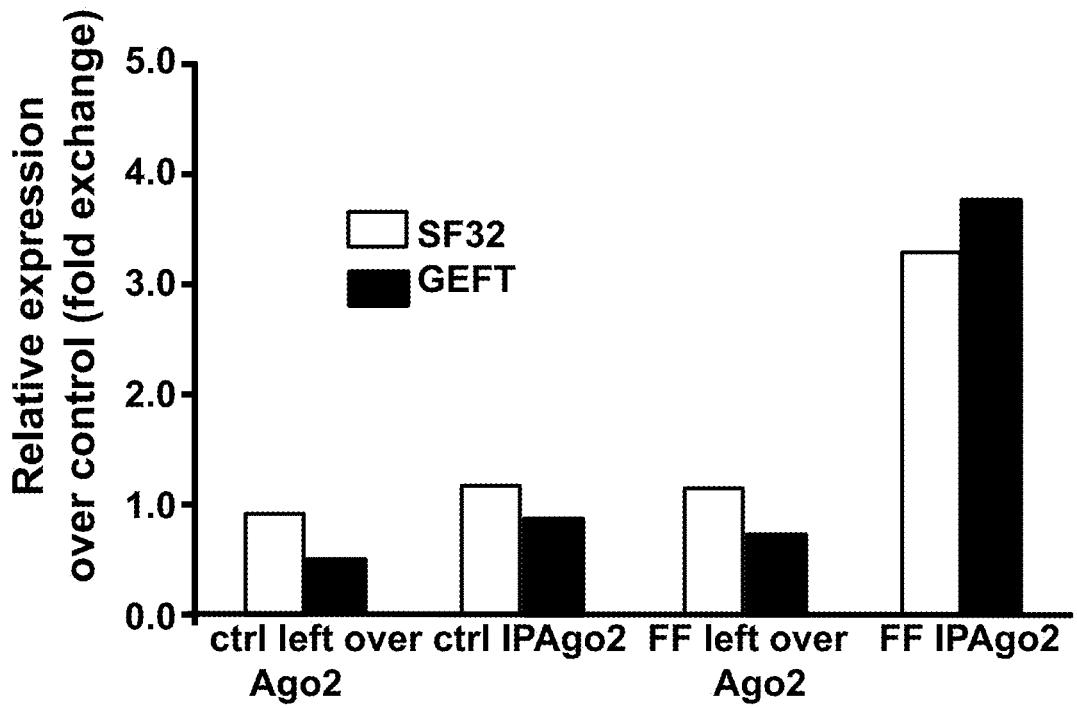

FIGS. 10A-10B illustrate that miR-3189-3p (SEQ ID NO: 2) is up-regulated and incorporated into the RNA-induced silencing complex (RISC) in cells treated with fenofibrate.

FIG. 10A is a graph illustrating the results of real-time PCR to detect miR-3189-3p (SEQ ID NO: 2) and miR-3189-5p (SEQ ID NO: 21) expression. Results are expressed as fold-change of the miRNAs in fenofibrate treated cells (FF) compared to untreated.

FIG. 10B is a graph illustrating SF3B2 and p63RhoGEF incorporation into Ago2 following treatment with fenofibrate. The enrichment of miRNAs or mRNAs in RISC was calculated according to the formula $2^{-(CtAgo2-CtIgG)}$ and normalized over RNU6B for miRNAs and GAPDH for mRNA.

FIGS. 11A-11D illustrate that fenofibrate treatment results in down-regulation of miR-3189-3p (SEQ ID NO: 2) target mRNAs and proteins in LN-229 cells.

Figure 11A:
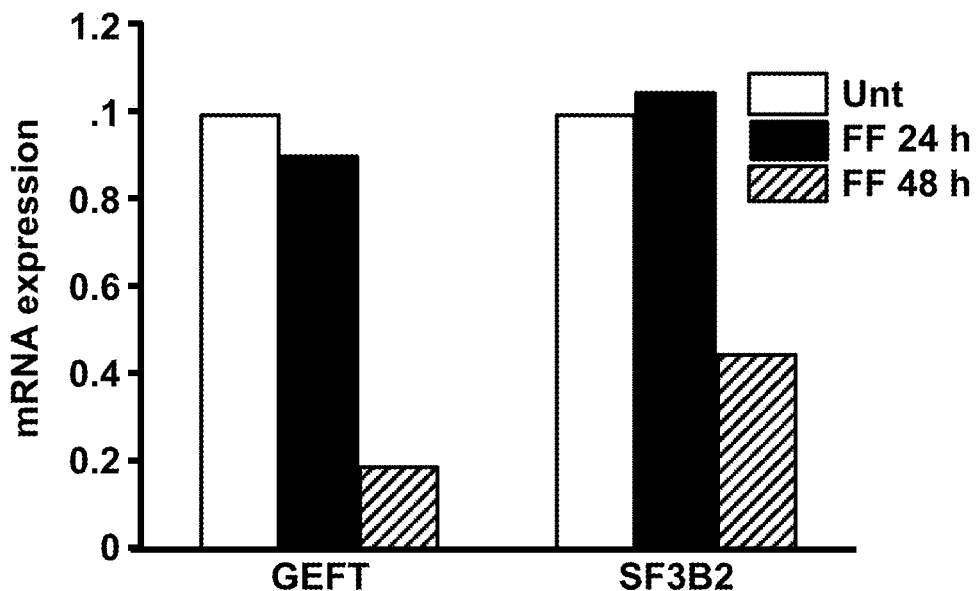

FIG. 11A is a graph illustrating qRT-PCR data showing changes in p63RhoGEF and SF3B2 mRNAs after fenofibrate treatment for 24 and 48 h. Results are expressed as fold-change of the mRNA in fenofibrate-treated cells compared to the untreated.

FIG. 11B is a graph illustrating qRT-PCR showing expression of p63RhoGEF and SF3B2 mRNAs in mock-transfected (ctrl), cells transfected with miR-3189-3p (SEQ ID NO: 2), and cells transfected with miR-3189-3p (SEQ ID NO: 2)+anti-miR-3189-3p (SEQ ID NO: 22). Results are expressed as fold-change compared to mock-treated cells.

FIG. 11C is a digital image illustrating Western blots for SF3B2 and p63RhoGEF proteins performed on lysates from cells that were untreated or treated with fenofibrate (FF) for 48 h. 14-3-3 antibody was used to show equal loading of cellular lysates.

FIG. 11D is a digital image illustrating Western blots for SF3B2 and p63RhoGEF proteins performed on lysates from cells transfected with mock, miR-3189-3p (SEQ ID NO: 2), or miR-3189-3p (SEQ ID NO: 2)+anti-miR-3189-3p (SEQ ID NO: 22) for 48 h.

Figure 12A:
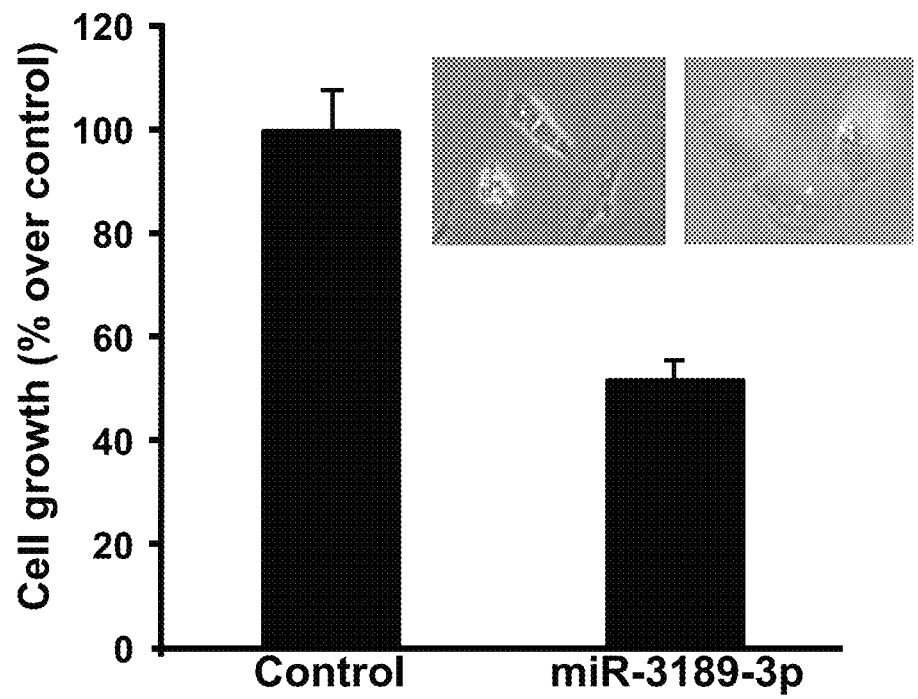
Figure 12B:
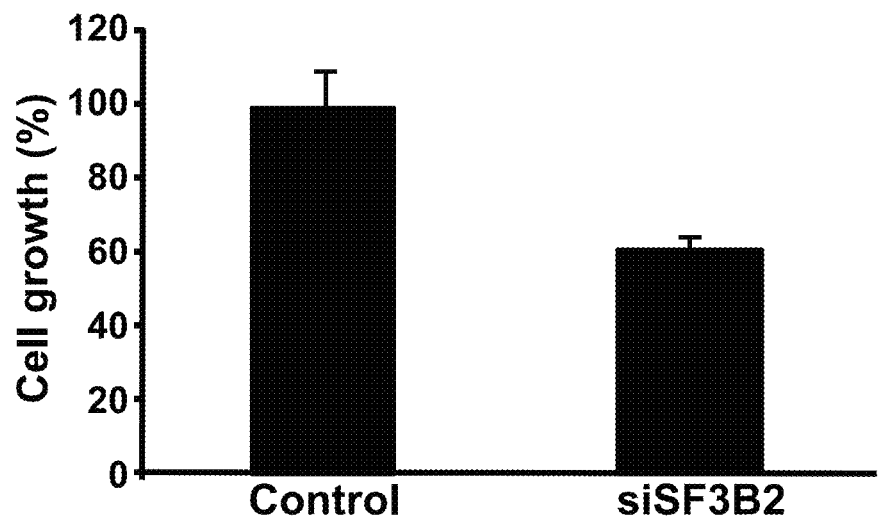

FIGS. 12A-12B illustrate that miR-3189-3p (SEQ ID NO: 2) alters the morphology and impairs the growth and migration of LN-229 glioblastoma cells.

FIG. 12A illustrates a cell growth assay performed 72 h post transfection with mock (ctrl), miR-3189-3p (SEQ ID NO: 2) or miR-3189-3p (SEQ ID NO: 2)+inhibitor and quantified using MTS reagent. Results are expressed as percent growth/mock-treated control. Inset phase contrast images showing the morphology of LN-229 cells following transfection with miR-3189-3p (SEQ ID NO: 2) or miR-3189-3p (SEQ ID NO: 2)+anti-miR-3189-3p (SEQ ID NO: 22); original magnification 10×. Images were acquired at 48 h post-transfection.

FIG. 12B illustrates a cell cycle analysis of LN-229 cells transfected with mock (ctrl), miR-3189-3p (SEQ ID NO: 2) and anti-miR-3189-3p (SEQ ID NO: 22). Cells were stained with Guava Cell Cycle reagent and cell cycle distribution (%) was quantified by flow cytometry using a FACSAria.

Figure 13A:
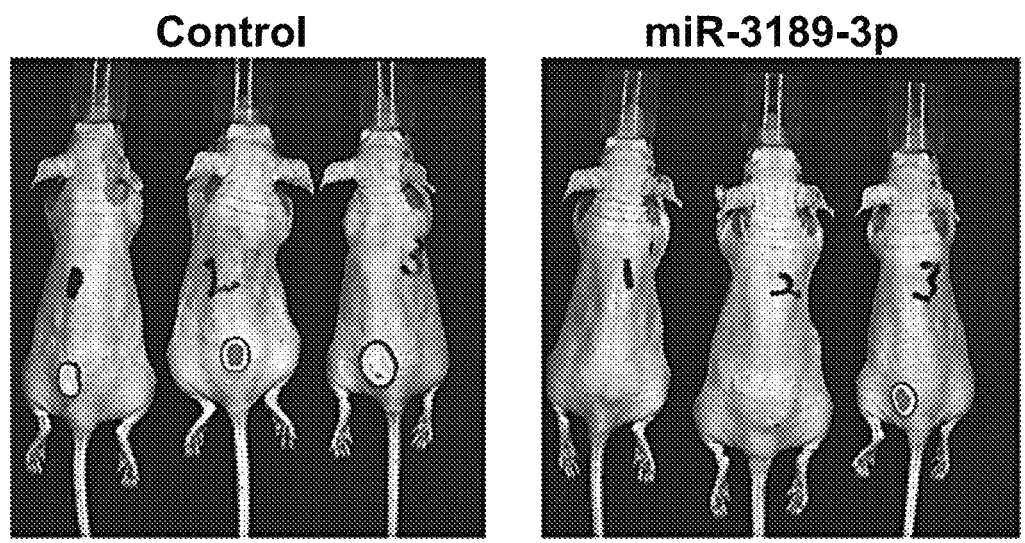
Figure 13B:
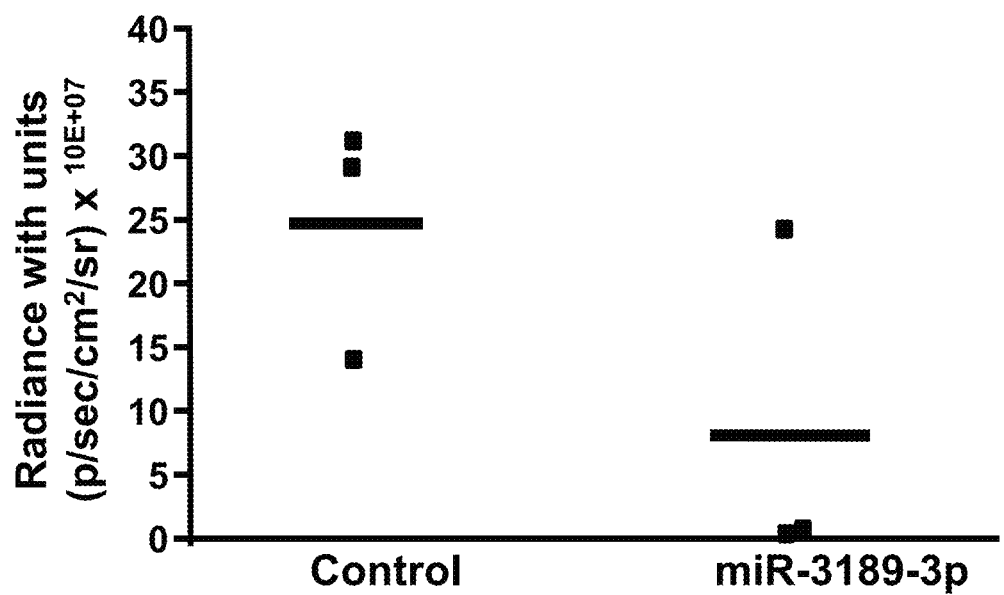

FIGS. 13A-13B illustrate that miR-3189-3p (SEQ ID NO: 2) blocks the growth of human glioblastoma cells in vivo.

FIG. 13A illustrates images of luciferase activity in U87MG cells implanted subcutaneously in nude mice.

FIG. 13B illustrates a plot of tumor burden 10 day post-injection with control or miR-3189-3p (SEQ ID NO: 2) transfected U87MG cells.

Figure 14A:
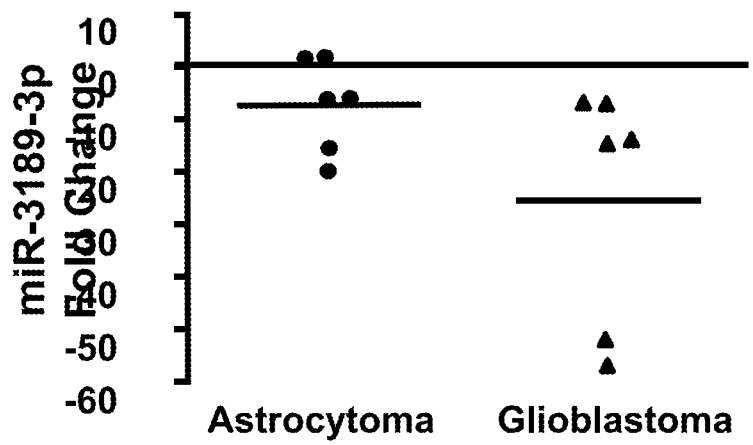
Figure 14B:
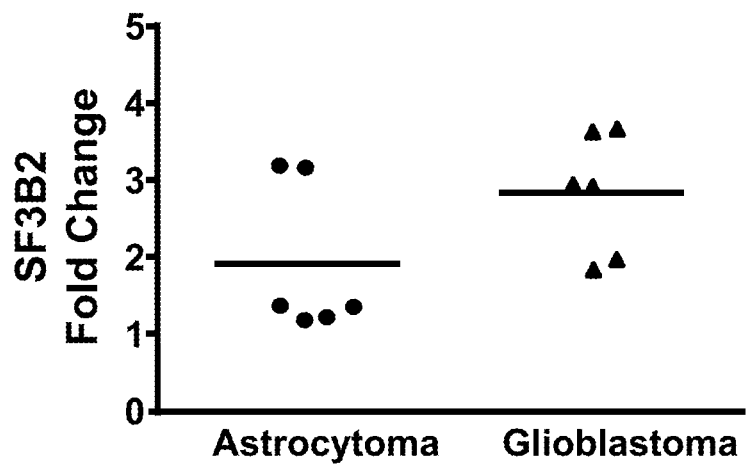
Figure 14C:
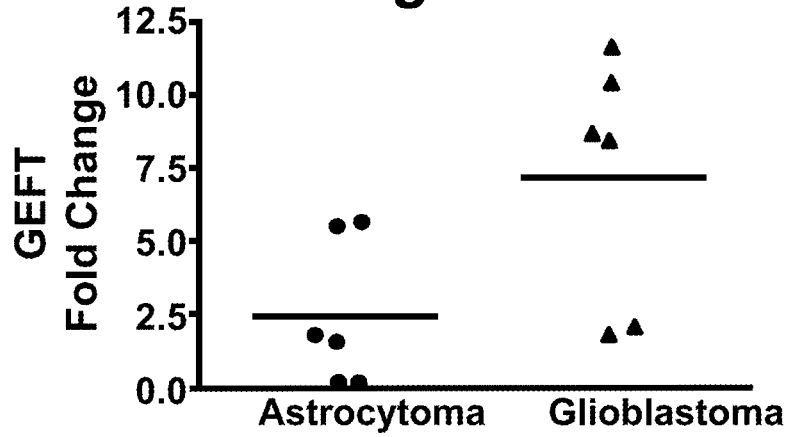

FIGS. 14A-14C illustrate that MiR-3189-3p expression inversely correlates with tumor grade and SF3B2 and GEFT expression in patient brain tumor samples.

FIG. 14A illustrates a real-time PCR analysis of RNA isolated from astrocytoma and glioblastoma samples correlating with tumor grade.

FIG. 14B illustrates a real-time PCR analysis of RNA isolated from astrocytoma and glioblastoma samples correlating with SF3B2 expression.

FIG. 14C illustrates a real-time PCR analysis of RNA isolated from astrocytoma and glioblastoma samples correlating with GEFT expression.

Figure 15:
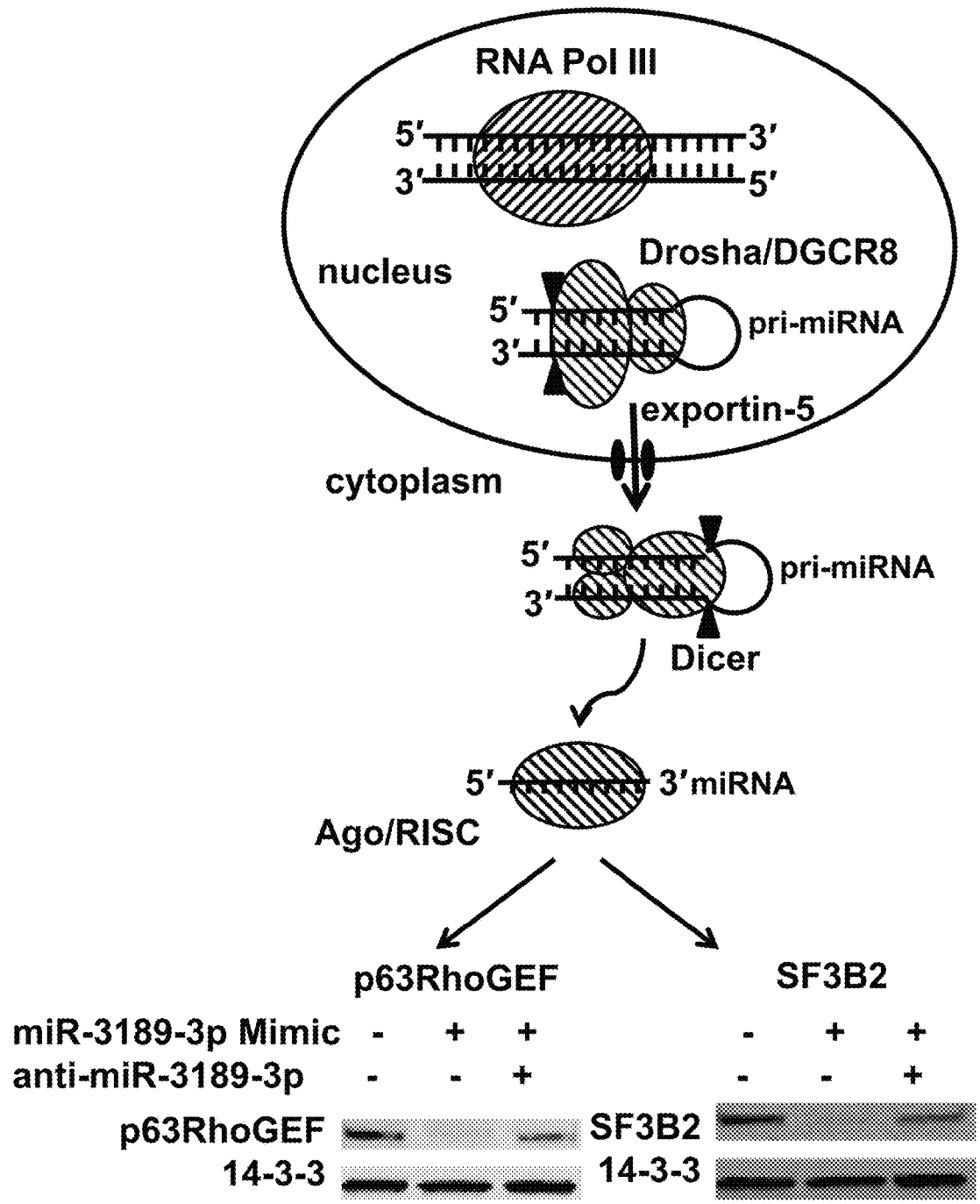

FIG. 15 illustrates a schematic showing the processing of miR-3189 to generate mature miR-3189-3p (SEQ ID NO: 2) and the targeting and down-regulation of the expression of the guanine nucleotide exchange factor, p63RhoGEF, and the SF3B2 splicing factor.

Figure 16A:
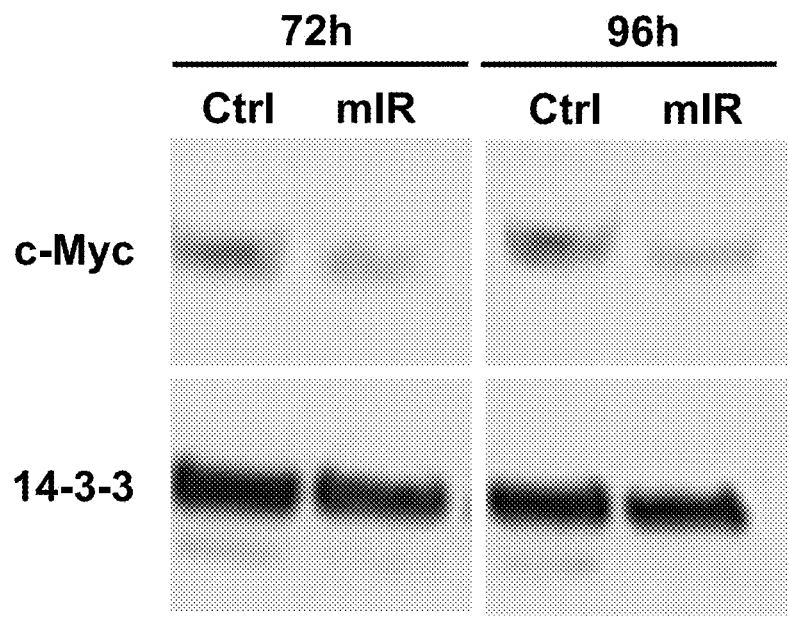
Figure 16B:
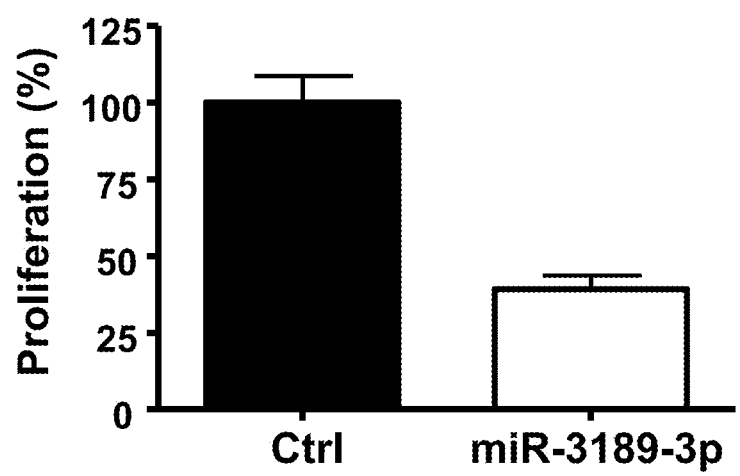

FIGS. 16A and 16B illustrate that the miR-3189-3p reduces levels of c-Myc protein and impairs the proliferation of TNBC cells.

FIG. 16A is a digital image of a Western blot showing that miR-3189-3p downregulated c-Myc protein levels 72 h post-transfection and 96 h post-transfection. 14-3-3 protein was used as the control for comparison.

FIG. 16B illustrates a graph showing that a cell proliferation assay performed 72 h post-transfection of MBA-MD-231 cells with mock (Ctrl) and miR-3189-3p revealed a significant decrease (p<0.05) in cell proliferation after miR-3189-3p treatment. Results are from two different experiments and are expressed in % growth/growth of control.

Figure 17A:
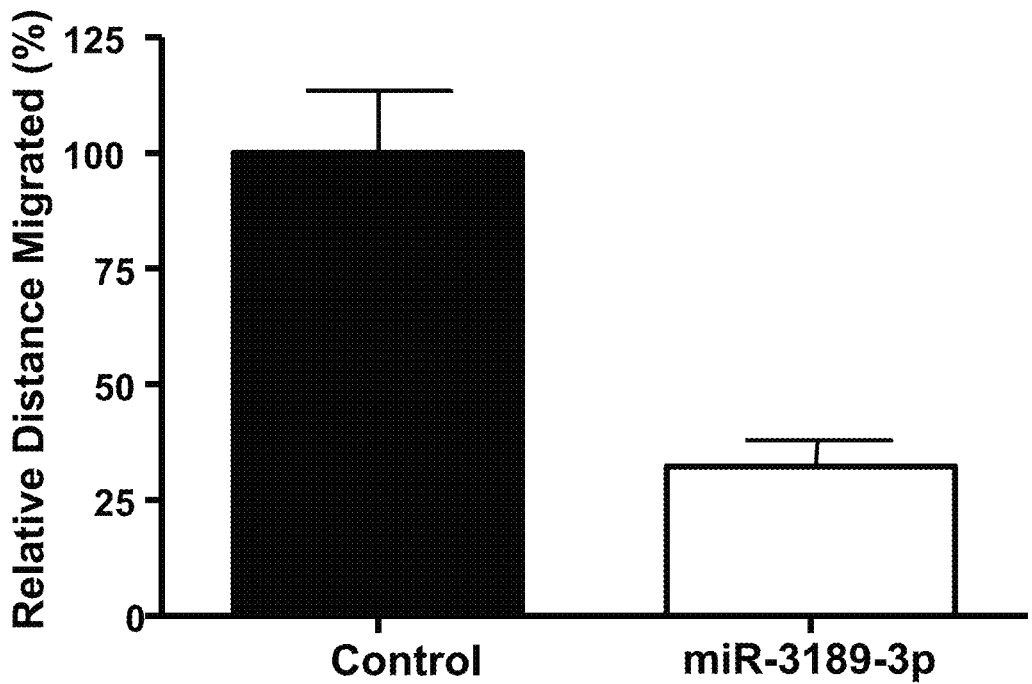
Figure 17B:
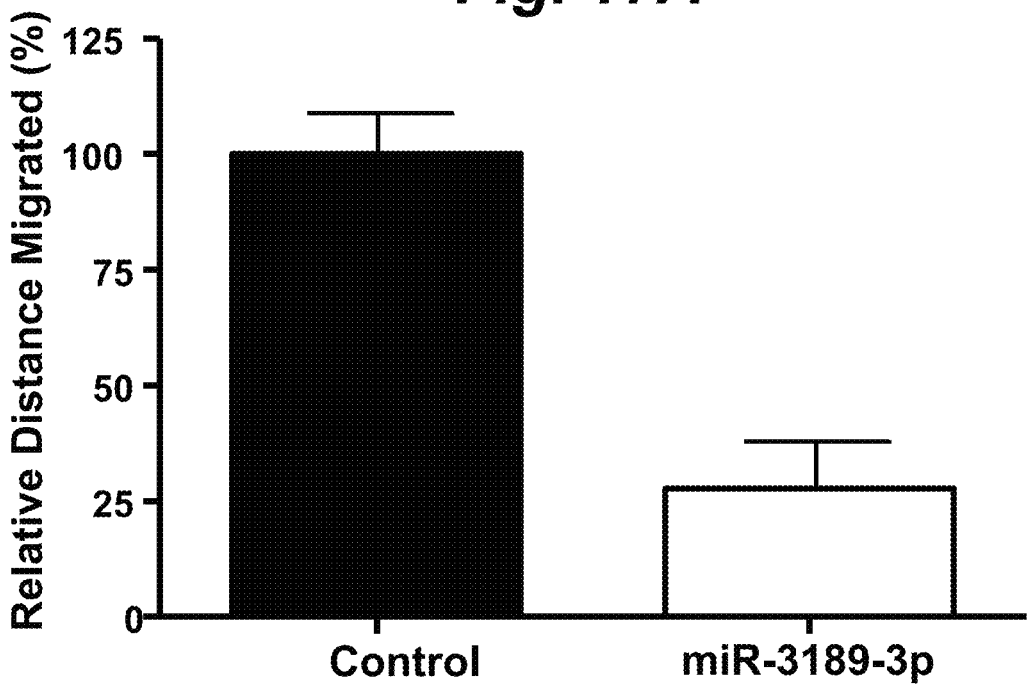

FIGS. 17A and 17B illustrate that treatment with miR-3189-3p blocks migration of Triple Negative Breast cancer (TNBC) cells.

FIG. 17A is a graph illustrating that MBA-MD-231 cells transfected with miR-3189-3p showed a significant ($p<0.05$) decrease in cell migration. Migration into the open groove was monitored by time-lapse imaging via a Vivaview fluorescent microscope set to capture an image every 30 mins. Results and representative images of the scratch assay conducted with 200,000 cells/60 mm plate.

FIG. 17B is a graph illustrating that MBA-MD-231 cells transfected with miR-3189-3p showed a significant ($p<0.05$) decrease in cell migration. Migration into the open groove was monitored by time-lapse imaging via a Vivaview fluorescent microscope set to capture an image every 30 mins. Results and representative images of the scratch assay conducted with 150,000 cells/60 mm plate.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, toxicology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Definitions

The term "cancer", as used herein, shall be given its ordinary meaning, as a general term for diseases in which abnormal cells divide without control. In particular, cancer refers to angiogenesis-related cancer. Cancer cells can invade nearby tissues and can spread through the bloodstream and lymphatic system to other parts of the body.

There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult.

Benign tumors have less of a tendency to invade and are less likely to metastasize. Brain tumors spread extensively within the brain but do not usually metastasize outside the brain.

The term "glioma" as used herein refers to a cancer of the central nervous system that begins in glial cells (i.e., cells that surround and support nerve cells and includes oligodendrocytes, astrocytes, microglia, and ependymal cells). Gliomas are particularly serious in terms of both incidence and malignancy, and are classified into seven or more types such as glioblastoma and anaplastic astrocytoma according to their detailed pathological tissue type. Disease stage (tumor size, presence of distal metastasis) and histological malignancy are used when determining the degree of malignancy of primary brain tumors.

Histological malignancy is classified into four levels, i.e., G1 to G4 according to the Guidelines for the Treatment of Brain Tumors ((2002) Kanehara & Co., Ltd.), and these correspond to WHO1 to WHO4, respectively. The larger the number, the higher the degree of malignancy. For example, the malignancy of glioblastoma is G4 (WHO4), while the malignancy of anaplastic astrocytoma is G3 (WHO3), and both G3 and G4 are classified as malignant.

The term "breast cancer" as used herein refers to, but is not limited to. Triple Negative breast cancer (TNBC), an aggressive subtype of breast cancer characterized by the lack of estrogen receptor, progesterone receptor, and HER-2. Consequently, TNBC cannot be treated by the available hormone therapies and receptor targeted treatments.

The term "MYC" as used herein refers to a regulatory gene involved in cell growth, metabolism, differentiation, and apoptosis, is disproportionately overexpressed in many TNBCs, making it a valuable therapeutic target. Myc (c-Myc) codes for a transcription factor. The protein encoded by this gene is a multifunctional, nuclear phosphoprotein that plays a role in cell cycle progression, apoptosis and cellular transformation.

A mutated version of Myc is found in many cancers, which causes Myc to be constitutively (persistently) expressed. This leads to the unregulated expression of many genes, some of which are involved in cell proliferation, and results in the formation of cancer. Malfunctions in Myc have also been found in carcinoma of the cervix, colon, breast, lung and stomach. Myc is thus viewed as a promising target for anti-cancer drug.

The term "decreasing at least one of the proliferation and the migration of a cell" as used herein refers to a reduction or inhibition of the replication in vivo or in cultured conditions of a cell or the migration of said cell either on the surface of a culture plate or from a site of a tumor to a different location in an animal or human having a tumor.

The term "contacting a cell or population of cells" as used herein refers to delivering a probe according to the present disclosure to an isolated or cultured cell or population of cells, or administering the probe in a suitable pharmaceutically acceptable carrier to the target tissue of an animal or human. Administration may be, but is not limited to, intravenous delivery, intraperitoneal delivery, intramuscular delivery, subcutaneous delivery, or by any other method known in the art. One advantageous method is to deliver directly into a blood vessel leading into a target organ or tissue such as a prostate, and so reducing dilution of the probe in the general circulatory system.

The term "microRNA (miRNA)" as used herein refers to single-stranded molecules that are generally 21 to 22 nucleotides in length, though lengths of 19 and up to 23 nucleotides have been reported. The miRNAs are each processed from a longer precursor RNA molecule ("precursor miRNA"). Precursor miRNAs are transcribed from non-protein-encoding genes. The precursor miRNAs have two regions of complementarity that enables them to form a stem-loop- or fold-back-like structure, which is cleaved in animals by a ribonuclease III-like nuclease enzyme called Dicer, as shown, for example, in FIG. 15. The processed miRNA is typically a portion of the stem.

The processed miRNA (also referred to as "mature miRNA") becomes part of a large complex to down-regulate a particular target gene or its gene product. Examples of animal miRNAs include those that imperfectly basepair with the target, which halts translation. siRNA molecules also are processed by Dicer, but from a long, double-stranded RNA molecule. siRNAs are not naturally found in animal cells, but they can direct the sequence-specific cleavage of an mRNA target through a RNA-induced silencing complex (RISC).

The term "miRNA" generally refers to a single-stranded molecule, but in specific embodiments, molecules of the present disclosure will also encompass a region or an additional strand that is partially (between 10% and 50% complementary across length of strand), substantially (greater than 50% but less than 100% complementary across length of strand) or fully complementary to another region of the same single-stranded molecule or to another nucleic acid. Thus, nucleic acids of the disclosure may encompass a molecule that comprises one or more complementary or self-complementary strand(s) or "complement(s)" of a particular sequence. For example, precursor miRNA may have a self-complementary region, which is up to 100% complementary. miRNA probes or nucleic acids of the invention can include, can be or can be at least 60, 65, 70, 75, 80, 85, 90, 95, 96, 97, 98, 99 or 100% complementary to their target.

The term "synthetic nucleic acid" as used herein refers to a nucleic acid that does not have all or part of a chemical structure or sequence of a naturally-occurring nucleic acid. Consequently, it will be understood that the term "synthetic miRNA" refers to a "synthetic nucleic acid" that functions in a cell or under physiological conditions as a naturally occurring miRNA.

While embodiments of the disclosure may involve synthetic miRNAs or synthetic nucleic acids, in some embodiments the nucleic acid molecule(s) need not be "synthetic." In certain embodiments, a non-synthetic nucleic acid or miRNA employed in methods and compositions of the invention may have the entire sequence and structure of a naturally occurring mRNA or miRNA precursor or the mature mRNA, or miRNA. For example, non-synthetic miRNAs used in methods and compositions of the invention may not have one or more modified nucleotides or nucleotide analogs. In these embodiments, the non-synthetic miRNA may or may not be recombinantly produced. In particular embodiments, the nucleic acid in methods and/or compositions of the invention is specifically a synthetic miRNA and not a non-synthetic miRNA (that is, not a miRNA that qualifies as "synthetic"); though other embodiments specifically involve a non-synthetic miRNA and not a synthetic miRNA. Any embodiments discussed with respect to the use of synthetic miRNAs can be applied with respect to non-synthetic miRNAs, and vice versa.

A synthetic miRNA or inhibitor may contain one or more design element(s). These design elements can include, but are not limited to: (i) a replacement group for the phosphate or hydroxyl of the nucleotide at the 5' terminus of the complementary region; (ii) one or more sugar modifications in the first or last 1 to 6 residues of the complementary region; or, (iii) non-complementarity between one or more nucleotides in the last 1 to 5 residues at the 3' end of the complementary region and the corresponding nucleotides of the miRNA region. A variety of design modifications are known in the art, see below.

A synthetic miRNA can have a nucleotide at its 5' end of the complementary region in which the phosphate and/or hydroxyl group has been replaced with another chemical group (referred to as the "replacement design"). In some cases, the phosphate group is replaced, while in others, the hydroxyl group has been replaced. The replacement group may be biotin, an amine group, a lower alkylamine group, an acetyl group, 2'O-Me (2'oxygen-methyl), DMTO (4,4'-dimethoxytrityl with oxygen), fluorescein, a thiol, or acridine, though other replacement groups are well known to those of skill in the art and can be used as well. This design element can also be used with a miRNA inhibitor.

A synthetic miRNA having one or more sugar modifications in the first or last 1 to 6 residues of the complementary region (referred to as the "sugar replacement design"). In certain cases, there is one or more sugar modifications in the first 1, 2, 3, 4, 5, 6 or more residues of the complementary region, or any range derivable therein. In additional cases, there are one or more sugar modifications in the last 1, 2, 3, 4, 5, 6 or more residues of the complementary region, or any range derivable therein, have a sugar modification. It will be understood that the terms "first" and "last" are with respect to the order of residues from the 5' end to the 3' end of the region. In particular embodiments, the sugar modification is a 2'O-Me modification, a 2'F modification, a 2'H modification, a 2'amino modification, a 4'thioribose modification or a phosphorothioate modification on the carboxy group linked to the carbon at position 6'. There may be one or more sugar modifications in the first or last 2 to 4 residues of the complementary region or the first or last 4 to 6 residues of the complementary region. This design element can also be used with a miRNA inhibitor. Thus, a miRNA inhibitor can have this design element and/or a replacement group on the nucleotide at the 5' terminus.

A synthetic miRNA or inhibitor may have one or more nucleotides in the last 1 to 5 residues at the 3' end of the complementary region not complementary to the corresponding nucleotides of the miRNA region ("non-complementarity") (referred to as the "non-complementarity design"). The non-complementarity may be in the last 1, 2, 3, 4, and/or 5 residues of the complementary miRNA. A non-complementarity may have at least 2 nucleotides in the complementary region.

The miRNA region and the complementary region may be on the same or separate polynucleotides. In cases in which they are contained on or in the same polynucleotide, the miRNA molecule will be considered a single polynucleotide. In embodiments in which the different regions are on separate polynucleotides, the synthetic miRNA will be considered to be comprised of two polynucleotides.

When the RNA molecule is a single polynucleotide, there can be a linker region between the miRNA region and the complementary region. The single polynucleotide may be capable of forming a hairpin loop structure as a result of bonding between the miRNA region and the complementary region. The linker constitutes the hairpin loop. It is contemplated that the linker region is, is at least, or is at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 residues in length, or any range derivable therein. In certain embodiments, the linker can be between 3 and 30 residues (inclusive) in length.

In addition to having a miRNA or inhibitor region and a complementary region, there may be flanking sequences as well at either the 5' or 3' end of the region. In some embodiments, there is or is at least 1, 2, 3, 4, 5, 6, 7, 8, 9, 10 nucleotides or more, or any range derivable therein, flanking one or both sides of these regions.

The term "naturally occurring" as used herein refers to something found in an organism without any intervention by a person; it could refer to a naturally-occurring wild-type or mutant molecule. A synthetic miRNA molecule may not have the sequence of a naturally occurring miRNA molecule. In other embodiments, a synthetic miRNA molecule may have the sequence of a naturally occurring miRNA molecule, but the chemical structure of the molecule, particularly in the part unrelated specifically to the precise sequence (non-sequence chemical structure) differs from chemical structure of the naturally occurring miRNA molecule with that sequence. In some cases, the synthetic miRNA has both a sequence and non-sequence chemical structure that are not found in a naturally-occurring miRNA. Moreover, the sequence of the synthetic molecules will identify which miRNA is effectively being provided or inhibited; the endogenous miRNA will be referred to as the "corresponding miRNA." Corresponding miRNA sequences that can be used in the context of the compositions and methods of the disclosure include, but are not limited to, all or a portion of those sequences in the SEQ IDs provided herein. In some embodiments, the sequence is, or is derived from, or contains all or part of, a sequence identified herein to target a particular miRNA (or set of miRNAs) that can be used with that sequence. Any 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130 140, 150, 160, 170, 180, 190, 200, 210, 220, 230, 240, 250, 260 or any number or range of sequences there between may be selected to the exclusion of all non-selected sequences.

The term "derivative" as used herein refers to a chemically modified or altered form of a naturally occurring molecule, while the terms "mimic" or "analog" refer to a molecule that may or may not structurally resemble a naturally occurring molecule or moiety, but possesses similar functions.

The term "moiety" as used herein refers to a smaller chemical or molecular component of a larger chemical or molecular structure. Nucleobase, nucleoside and nucleotide analogs or derivatives are well known in the art.

The term "nucleobase" as used herein refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in a manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, carboxyalkyl, amino, hydroxyl, halogen (i.e., fluoro, chloro, bromo, or iodo), thiol or alkylthiol moiety. Alkyl (e.g., alkyl, carboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-dimethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

The term "nucleoside" as used herein refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring. Different types of covalent attachment(s) of a nucleobase to a nucleobase linker moiety are known in the art.

The term "nucleotide" as used herein refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the invention.

Labeling methods and kits of the disclosure specifically contemplate the use of nucleotides that are both modified for attachment of a label and can be incorporated into a miRNA molecule. Such nucleotides include those that can be labeled with a dye, including a fluorescent dye, or with a molecule such as biotin. Labeled nucleotides are readily available; they can be acquired commercially or they can be synthesized by reactions known to those of skill in the art.

Modified nucleotides for use in the invention are not naturally occurring nucleotides, but instead, refer to prepared nucleotides that have a reactive moiety on them. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the other such chemical groups.

The reactive functionality may be bonded directly to a nucleotide, or it may be bonded to the nucleotide through a linking group. The functional moiety and any linker cannot substantially impair the ability of the nucleotide to be added to the miRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in many embodiments is alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors. Functional groups may be prepared according to ways known to those of skill in the art, including the representative information found in U.S. Pat. Nos. 4,404,289; 4,405,711; 4,337,063 and 5,268,486, and U.K. Patent 1,529,202, which are all incorporated by reference.

Amine-modified nucleotides may be used. The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribonucleotides: 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-aminodATP; N6-(4-amino)butyl-dATP, N6-(6-amino)butyl-dATP, N4-[2,2-oxy-bis-(ethylamine)]-dCTP; N6-(6-Amino)hexyl-dATP; 8-[(6-Amino)hexyl]-amino-dATP; 5-propargylamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

The term "miRNA inhibitor" as used herein refers to a nucleic acid of between about 17 to 25 nucleotides in length and comprises a 5' to 3' sequence that is at least 90% complementary to the 5' to 3' sequence of a mature miRNA. In certain embodiments, a miRNA inhibitor molecule is 17, 18, 19, 20, 21, 22, 23, 24, or 25 nucleotides in length, or any range derivable therein. Moreover, an miRNA inhibitor may have a sequence (from 5' to 3') that is or is at least 70, 75, 80, 85, 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature miRNA, particularly a mature, naturally occurring miRNA. One of skill in the art could use a portion of the miRNA sequence that is complementary to the sequence of a mature miRNA as the sequence for a miRNA inhibitor. Moreover, that portion of the nucleic acid sequence can be altered so that it is still comprises the appropriate percentage of complementarity to the sequence of a mature miRNA.

The term "complementary region" or "complement" refers to a region of a nucleic acid or mimetic that is or is at least 60% complementary to the mature, naturally occurring miRNA sequence. The complementary region is or is at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein. With single polynucleotide sequences, there may be a hairpin loop structure as a result of chemical bonding between the miRNA region and the complementary region. The complementary region may be on a different nucleic acid molecule than the miRNA region, in which case the complementary region is on the complementary strand and the miRNA region is on the active strand.

The term "expression" as used herein refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The term "gene" as used herein refers to a nucleic acid fragment that expresses a functional molecule such as, but not limited to, a specific protein, including regulatory sequences preceding (5' non-coding sequences) and following (3' non-coding sequences) the coding sequence.

The term "percentage of sequence identity" as used herein refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Polynucleotide and polypeptide sequences, variants thereof, and the structural relationships of these sequences can be described by the terms "homology", "homologous", "substantially identical", "substantially similar" and "corresponding substantially" which are used interchangeably herein. These terms as used herein refer to polypeptide or nucleic acid fragments wherein changes in one or more amino acids or nucleotide bases do not affect the function of the molecule, such as the ability to mediate gene expression or to produce a certain phenotype. These terms also refer to modification(s) of nucleic acid fragments that do not substantially alter the functional properties of the resulting nucleic acid fragment relative to the initial, unmodified fragment. These modifications include deletion, substitution, and/or insertion of one or more nucleotides in the nucleic acid fragment.

The term "pharmaceutically acceptable carrier, excipient, or vehicle" as used herein refers to a medium which does not interfere with the effectiveness or activity of an active ingredient and which is not toxic to the hosts to which it is administered. A carrier, excipient, or vehicle includes diluents, binders, adhesives, lubricants, disintegrates, bulking agents, wetting or emulsifying agents, pH buffering agents, and miscellaneous materials such as absorbents that may be needed in order to prepare a particular composition. Examples of carriers etc. include but are not limited to saline, buffered saline, dextrose, water, glycerol, ethanol, and combinations thereof. The use of such media and agents for an active substance is well known in the art.

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Abbreviations miRNA, microRNA; 3'UTR, 3' untranslated region; mRNA, messenger RNA; GBM. glioblastoma; FF, fenofibrate (propan-2-yl 2-{4-[(4-chlorophenyl)carbonyl]phenoxy}-2-methylpropanoate); RISC, RNA-induced silencing complex; GAPDH, glyceraldehyde phosphate dehydrogenase; GDF15, Growth Differentiation Factor 15; NAG-1, Nonsteroidal Anti-inflammatory drug-activated Gene-1; MIC-1, Macrophage Inhibitory Cytokine-1; TGF-β, Transforming Growth Factor-β; MTS, 3-(4,5-dimethylthiazol-2-yl)-5-(3-carboxymethoxyphenyl)-2-(4-sulfophenyl)-2H-tetrazolium; TN BC, Triple negative breast cancer.

Description

The present invention is directed to compositions and methods relating to the use of miRNAs related to such, for therapeutic applications, particularly those methods and compositions related to pathological conditions directly or indirectly related to miR-3189 expression or the aberrant expression thereof.

MicroRNAs are short single-stranded non-coding RNAs that regulate gene expression by incomplete base pairing with mRNAs. Alterations in microRNA expression have been associated with a variety of pathologies including cancer. In addition to their impact in carcinogenesis, microRNAs have been investigated for their potential values in diagnosis, prognosis and cancer therapy. In this study, it was found that miR-3189-3p (SEQ ID NO: 2) is down-regulated in astrocytoma and glioblastoma clinical samples in comparison to unaffected brain tissue.

Genomic sequence analysis revealed that the nucleotide sequence encoding miR-3189 stem loop (SEQ ID NO: 1) is located in the intron of the Growth Differentiation Factor 15 (GDF15) gene. Increased expression of GDF15 in the LN-229 glioblastoma cell line following the treatment with fenofibrate was found (Jeansonne et al., (2013) *Genes* 4: 46-64). Fenofibrate is an agonist of peroxisome proliferator-activated receptor alpha (PPARα) commonly used as a lipid-lowering drug, which has strong antiglioblastoma properties (Drukala et al., (2010) *Mol. Cancer* 9: 159; VVilk et al., (2014) *Mol. Cell Biol.* 35: 182-198).

GDF15, also known as Nonsteroidal Anti-inflammatory drug-activated Gene-1 (NAG-1) or Macrophage Inhibitory Cytokine-1 (MIC-1), is a member of the Transforming Growth Factor-β (TGF-β) superfamily (Mimeault &Batra (2010) *J. Cell. Physiol.* 224: 626-635; Wang et al., (2013) *Biochem. Pharmacol.* 85: 597-606). The GDF15 gene is encoded by two exons, which produce a precursor protein further cleaved to generate a 112 amino acid mature GDF15 peptide that is secreted into the extracellular matrix as a biologically active dimer (Eling et al, (2006) *J. Biochem. Molecular Biol.* 39, 649-655).

GDF15 can be induced by anti-inflammatory drugs, cytotoxic agents, PPAR agonists, and anticancer drugs (Jeansonne et al., (2013) *Genes* 4: 46-64; Kim et al., (2013) *Mediators Inflammation* 2013: 641851). Increased GDF15 mRNA expression has been reported in patients during malignant progression to glioblastomas (Li et al, (2009) *Cancer Res.* 69: 2091-2099), and others have reported that expression levels of GDF15 are up-regulated in glioblastoma cells in response to cytotoxic stimuli during chemotherapy treatment (Jeansonne et al., (2013) *Genes* 4: 46-64; Chiu et al., (2011) *BMC Cancer* 11, 146; Yoshioka et al., (2008) *J. Biol. Chem.* 283: 33129-33137).

The precursor sequence encoded by miR-3189 (SEQ ID NO: 1) contains two mature microRNA sequences within the stem-loop: miR-3189-3p (SEQ ID NO: 2) and miR-3189-5p (SEQ ID NO: 21), of 21 and 25 nucleotides in length, respectively. The biological function of these microRNAs has never been described.

Ectopic expression of miR-3189-3p (SEQ ID NO: 2) has now been shown to inhibit glioblastoma cell growth and migration through down-regulation of SF3B2 and p63RhoGEF, respectively. In comparison to normal brain tissue, astrocytoma and glioblastoma clinical samples have increased levels of GDF15 and decreased levels of miR-3189-3p (SEQ ID NO: 2), and that these changes correlated with increased expression of SF3B2 and p63RhoGEF. Finally, the subcutaneous and intracranial growth of glioblastoma cells expressing miR-3189-3p (SEQ ID NO: 2) was significantly reduced when compared to the parental control cells, thus further supporting the role of this microRNA as a tumor suppressor.

miR-3189 (SEQ ID NO: 1) has been previously identified as a possible mirtron expressed in melanoma (Stark et al., (2010) *PloS one* 5, e9685), and an inhibitory effect of miR-3189-5p (SEQ ID NO: 21) on TGFβR2 has been hypothesized (Sivadas et al., (2013) *Genes, Chromosomes Cancer* 52: 1042-1052), but a function attributed to miR-3189-3p (SEQ ID NO: 2) or miR-3189-5p (SEQ ID NO: 21) has not been validated experimentally. Mirtrons are microRNAs encoded within introns and their biogenesis follows a non-canonical, Drosha/DGCR8-independent, pathway that relies on the mRNA splicing and on RNA lariats debranching enzymes (Lai, E. C. (2003) *Curr. Biol.* 13: R925-936). Differently from canonical pre-microRNA stem-loops, microRNAs generated from the 3' (-3p) of the mirtron hairpin appear to be more stable than those generated from the 5' (-5p) (Okamura e al, (2007) *Cell* 130: 89-100). This may explain why, even if miR-3189-5p (SEQ ID NO: 21) expression was slightly and variably induced by mitogenic stimuli (10% FBS), this microRNA was not detected in the Ago2-immunoprecipitated complex.

The present disclosure shows that overexpression of miR-3189-3p (SEQ ID NO: 2) in LN229 and U87MG cells resulted in morphological changes accompanied by attenuation of cell proliferation and migration (FIGS. 1A-1F). Indeed, the anti-proliferative effect miR-3189-3p (SEQ ID NO: 2) prevented the generation of stable cell lines expressing this microRNA. MicroRNA gene target prediction databases indicated the splicing factor SF3B2 and the Rho guanine nucleotide exchange factor p63RhoGEF as the top putative targets. Given their validated role in proliferation and migration (see below) their role in the biological effects of miR-3189-3p (SEQ ID NO: 2) was investigated. Overexpression of miR-3189-3p (SEQ ID NO: 2) in LN-229 and U87MG cells resulted in down-regulation of SF3B2 and p63RhoGEF mRNAs (FIG. 2A) and proteins (FIG. 2B).

Although the down-regulation of SF3B2 and p63RhoGEF mRNAs was comparable in the two cell lines, it was stronger at the level of proteins in LN-229 cells. This may suggest a different mechanism of post-transcriptional regulation for these proteins in the two types of cells tested. Nevertheless, expression of miR-3189-3p (SEQ ID NO: 2) had a strong biological effect on both LN-229 and U87MG cells, impairing their migration and growth. These effects were shown to be mediated through down-regulation of p63RhoGEF and SF3B2, respectively.

With respect to p63RhoGEF, previous reports have shown a role for this protein in cell migration (Swenson-Fields et al., (2008) *Mol. Cell.* 32: 43-56; Tang et al., (2013) *Cancer Res.* 73: 6206-6218). Specifically it was demonstrated that the expression of p63RhoGEF is essential for lamellipodial polarization during serum-induced chemotaxis (Orr et al., (2012) *Mol, Systems Biol.* 8: 573). The findings are in agreement with a role for p63RhoGEF in cell motility, since siRNA against p63RhoGEF impaired migration of LN-229 cells (FIG. 3D). Further, the results showing the inhibitory effect of miR-3189-3p (SEQ ID NO: 2) on p63RhoGEF overexpressing cells (FIG. 3C) demonstrate that inhibition of cell migration by miR-3189-3p (SEQ ID NO: 2) is only partially due to the down-regulation of p63RhoGEF. Such result may not be surprising, since other members of the RhoA family of guanine nucleotide exchange factors, such as SLIT-ROBO Rho GTPase activating protein 2 (SRGAP2) and Rho guanine nucleotide exchange factor (GEF) 12 (ARCHGEF12) are other putative targets of miR-3189-3p (SEQ ID NO: 2) and may equally contribute to the impaired cell migration by miR-3189-3p (SEQ ID NO: 2). Likewise, the striking change in cellular morphology upon expression of miR-3189-3p (SEQ ID NO: 2) might be the result of this microRNA targeting multiple genes involved in cytoskeletal remodeling.

It has been reported that the expression of the transcription factor E2F-1 is dependent on the presence of SF3B2 in the cell (Orr et al., (2012) *Mol, Systems Biol.* 8: 573). Furthermore, E2F-1 has been shown to be a master regulator of cell cycle progression (DeGregori et al., (1995) *Mol. Cell Biol.* 15: 4215-4224; Matsumura et al., (2003) *Cell Cycle* 2: 333-338). Therefore, it is not surprising that SF3B2 down-regulation by miR-3189-3p (SEQ ID NO: 2) in glioblastoma delayed cell growth. This effect was shown to be dependent on SF3B2, as overexpression of this gene in the presence of miR-3189-3p (SEQ ID NO: 2) restored the proliferative capacity of LN-229 cells (FIG. 3A). The antiproliferative activity of miR-3189-3p (SEQ ID NO: 2) was also demonstrated in vivo in nude mice bearing subcutaneous LN-229/pmCherry (FIGS. 4A and 4B) or U87MG/luciferase tumors and with intracranial injection of U87MG/luciferase cells previously treated with vehicle or miR-3189-3p (SEQ ID NO: 2) (FIGS. 4C and 4E).

Figure 1A:
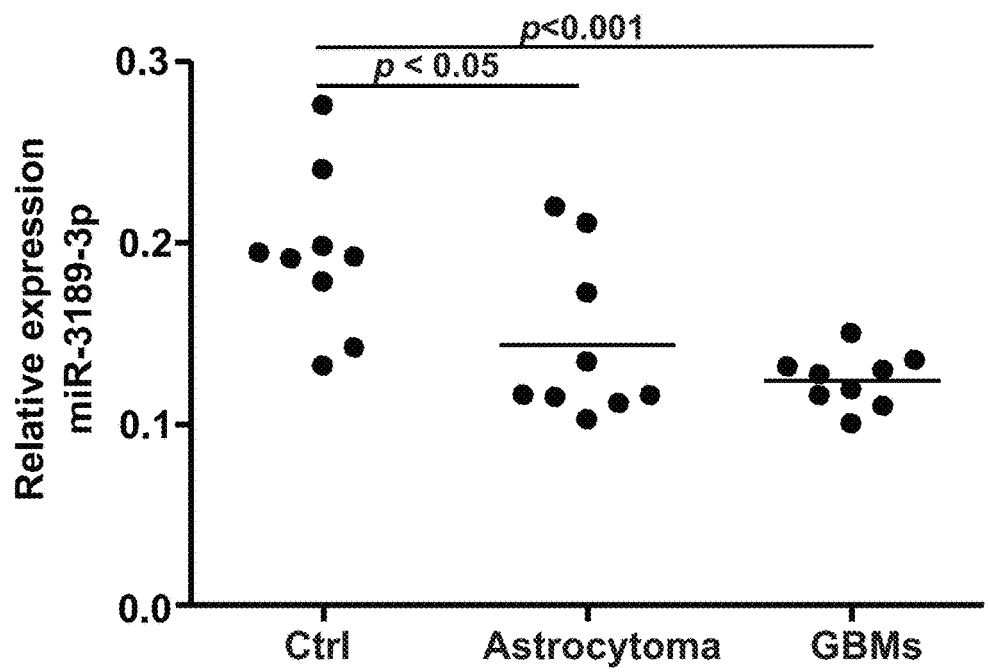
FIGS. 1A-1F illustrate that miR-3189-3p is down-regulated in glial tumors and affects growth and migration of glioblastoma cells in culture.

Accordingly, since the genomic sequence of miR-3189-3p (SEQ ID NO: 2) is located in the intron of GDF15, it was determined if this microRNA could be co-expressed and could have been involved in the activity of GDF15. The data indicate, however, that these two molecules are differentially regulated in various experimental and clinical settings. Analysis of clinical samples indicates that GDF15 is undetectable in control brain tissues and up-regulated in gliomas while miR-3189-3p (SEQ ID NO: 2) is present in normal brain tissue and down-regulated in gliomas (FIGS. 5B and 1A, respectively). LN-229 cells were serum-starved and then stimulated with 10% FBS or EGF (50 ng/ml) for various time points. It was found that FBS treatment down-regulated GDF15, and both up-regulated miR-3189-3p (SEQ ID NO: 2) and miR-3189-5p (SEQ ID NO: 21), while EGF up-regulated GDF15 but did not significantly change expression of either microRNAs.

Cytotoxic agents such as etoposide and doxorubicin have been shown to increase GDF15 expression (Mimeault & Batra (2010) *J. Cell. Physiol.* 224: 626-635). However, among doxorubicin, paclitaxel and fenofibrate, only the latter was able to increase both GDF15 and miR-3189-3p (SEQ ID NO: 2) expression (FIG. 6E). It is likely that the discrepancy of these results with previous work is due to the type of cells utilized. Indeed, fenofibrate treatment triggered two times more GDF15 and miR-3189-3p (SEQ ID NO: 2) expression in LN-229 than in U87MG cells, suggesting variability in responses within the same type of tumor cells.

It was also observed that, at least in LN-229 cells, although fenofibrate treatment always induced expression of GDF15, such expression ranged between 5-6 folds to 60 folds (compare FIGS. 6A, 6E, 7C, and 7D) within 48 h treatment, while the range of miR-3189-3p (SEQ ID NO: 2) expression was consistently between 2.5 and 5. Again, this discrepancy may indicate that expression of GDF15 and of miR-3189-3p (SEQ ID NO: 2) are independently regulated and that expression of GDF15 likely follows a Gaussian curve with the pick in a dynamic range.

Overexpression of GDF15 protein or treatment of LN-229 cells with its soluble version did not elicit any morphological or biological effects in LN-229 cells in vitro. Similarly, the anti-miR-3189-3p (SEQ ID NO: 22) did not protect fenofibrate-treated cells from apoptosis, indicating that up-regulation of miR-3189-3p (SEQ ID NO: 2) is not required for fenofibrate-mediated cell death. Given the broad range of anticancer effects triggered by fenofibrate (Drukala et al., (2010) *Mol. Cancer* 9: 159; Wilk et al., (2014) *Mol. Cell Biol.* 35: 182-198; Araki et al., (2009) *Angiogenesis* 12: 221-229; Wilk et al., (2012) *Cell Cycle* 11: 2660-2671; Urbanska et al., (2008) *Int. J. Cancer* 123: 1015-1024; Panigrahy et al., (2008) *Proc. Nat. Acad. Sci. U.S.A.* 105, 985-990) and the activity of a single microRNA, it is not surprising that miR-3189-3p (SEQ ID NO: 2) is not contributing to the massive cell death mediated by fenofibrate.

Accordingly, the microRNA itself seems to have a cytostatic rather than cytotoxic effect on the cells (FIGS. 1A-1F). Treatment of glioblastoma cells with fenofibrate results in massive cell death, which occurs between 48 and 72 h post treatment and involves PPARα-dependent and -independent mechanisms (Drukala et al., (2010) *Mol. Cancer* 9: 159; Wilk et al., (2014) *Mol. Cell Biol.* 35: 182-198; Araki et al., (2009) *Angiogenesis* 12: 221-229; Wilk et al., (2012) *Cell Cycle* 11: 2660-2671; Urbanska et al., (2008) *Int. J. Cancer* 123: 1015-1024; Panigrahy et al., (2008) *Proc. Nat. Acad. Sci. U.S.A.* 105, 985-990). Up to 48 h post-treatment cells appear normal in morphology, although still suffering from mitochondrial dysfunction and metabolic crisis (Wilk et al., (2014) *Mol. Cell Biol.* 35: 182-198). Increased expression of GDF15 and/or miR-3189-3p (SEQ ID NO: 2) appears to be a PPARα-independent event (FIGS. 7C and 7D) and could be the result of mitochondrial stress and, similarly to induction of autophagy (Wilk et al., (2014) *Mol. Cell Biol.* 35: 182-198), it may reflect an attempt from the cells to counteract the toxic effects of fenofibrate.

miR-3189-3p (SEQ ID NO: 2) being highly incorporated into the Ago2 complex (FIGS. 7A-7D) indicates that it is functionally active in this context. While not wishing to be bound by any one theory, it is possible that the effect of miR-3189-3p (SEQ ID NO: 2) on its targets may augment a parallel, irreversible action (perhaps transcriptional) on the same targets exerted by fenofibrate through microRNA-independent mechanisms. Accordingly, the tumor suppressor activity in vitro and in vivo of an overexpressed miR-3189-3p (SEQ ID NO: 2) is contemplated to provide a therapy for glioblastoma, melanoma, and other cancers as well. For example, but not intended to be limiting, it has been found that miR-3189-3p (SEQ ID NO: 2), when expressed in breast cancer cells, will inhibit both the proliferation and migration of such cells, as shown in FIGS. 16A-17B. In particular, miR-3189-3p (SEQ ID NO: 2), when expressed in cancer cells that have originated from a mutation or change in regulation of the myc gene, is particularly effective in reducing or eliminating the changes induced by such a change in MYC.

In summary, therefore, glioblastoma is one of the most aggressive brain tumors. Up-regulation of Growth Differentiation Factor 15, GDF15, was found in glioblastoma cells treated with the anti-cancer agent fenofibrate. Sequence analysis of GDF15 revealed the presence of a microRNA, miR-3189, in the single intron. Expression of miR-3189-3p (SEQ ID NO: 2) was down-regulated in astrocytoma and glioblastoma clinical samples compared to control brain tissue. In vitro, functionality of miR-3189-3p (SEQ ID NO: 2) was tested by RNA-binding protein immunoprecipitation, and miR-3189-3p (SEQ ID NO: 2) co-immunoprecipitated with Argonaute 2 together with two of its major predicted gene targets, the SF3B2 splicing factor and the guanine nucleotide exchange factor p63RhoGEF. Overexpression of miR-3189-3p (SEQ ID NO: 2) resulted in a significant inhibition of cell proliferation and migration through direct targeting of SF3B2 and p63RhoGEF, respectively. miR-31893p levels were increased by treatment of glioblastoma cells with fenofibrate, a lipid-lowering drug with multiple anticancer activities. The attenuated expression of miR-3189-3p (SEQ ID NO: 2) in clinical samples paralleled the elevated expression of SF3B2, which could contribute to the activation of SF3B2 growth promoting pathways in these tumors. Finally, miR-3189-3p (SEQ ID NO: 2)-mediated inhibition of tumor growth in vivo further supported the function of this microRNA as a tumor suppressor.

In various aspects of the disclosure, a subject or patient may be selected for treatment based on expression and/or aberrant expression of one or more miRNA or mRNA, wherein aberrant expression is understood to relate to a level of expression differing from what is typically found in a non-cancerous cell of the same type. In still a further aspect, a subject or patient may be selected based on aberrations in miRNA expression, or biologic and/or physiologic pathway(s). A subject may be assessed for sensitivity, resistance, and/or efficacy of a therapy or treatment regime based on the evaluation and/or analysis of miRNA or mRNA expression or lack thereof. A subject may be evaluated for amenability to certain therapy prior to, during, or after administration of one or therapy to a subject or patient. Typically, evaluation or assessment may be done by analysis of the miRNA expression, as well as combination of other assessment methods that include but are not limited to histology, immunohistochemistry, blood work, etc.

Accordingly, the present disclosure provides methods and compositions for identifying genes that are direct targets for miR-3189 regulation or that are downstream targets of regulation following the miR-3189-mediated modification of upstream gene expression. Furthermore, the disclosure describes gene pathways and networks that are influenced by miR-3189 expression in biological samples. Many of these genes and pathways are associated with various cancers and other diseases. It is contemplated that the altered expression or function of miR-3189 in cells will lead to changes in the expression of these genes and contribute to the development of disease or other conditions. Introducing miR-3189 (for diseases where the miRNA is down-regulated) or a miR-3189 inhibitor (for diseases where the miRNA is up-regulated) into disease cells or tissues or subjects would result in a therapeutic response. The identities of key genes that are regulated directly or indirectly by miR-3189 and the disease with which they are associated are provided herein.

In certain aspects a cell receiving the miRNA species of the disclosure may be an epithelial, an endothelial, a mesothelial, a glial, a stromal, or a mucosal cell. The cell can be, but is not limited to a brain, a neuronal, or a skin cell. A cell, tissue, or subject may be a cancer cell, a cancerous tissue, harbor cancerous tissue, or be a subject or patient diagnosed or at risk of developing a disease or condition. In still a further aspect cancer includes, but is not limited to astrocytoma, glioma, glioblastoma, glioblastoma multiforme, or skin cancer.

In certain aspects, the cell, tissue, or target may not be defective in miRNA expression yet may still respond therapeutically to expression or over expression of a miRNA. miR-3189 could be used as a therapeutic target for any of these diseases. In certain embodiments 3189 or its compliment can be used to modulate the activity of miR-3189 in a subject, organ, tissue, or cell.

The disclosure further encompasses methods of modulating gene expression, or biologic or physiologic pathways in a cell, a tissue, or a subject comprising administering to the cell, tissue, or subject an amount of an isolated nucleic acid or mimetic thereof comprising a miR-3189 nucleic acid, mimetic, or inhibitor sequence in an amount sufficient to modulate the expression of a gene positively or negatively modulated by a miR-3189 miRNA. A "miR-3189 nucleic acid sequence" or "miR-3189 inhibitor" includes the full length precursor of miR-3189 (SEQ ID NO: 1), or complement thereof or processed (i.e., mature) sequence of miR-3189 and related sequences set forth herein, as well as 5, 6, 7, 8, 9, 10, 11, 12, 13, 14, 15, 16, 17, 18, 19, 20, 21, 22, 23, 24, 25, 26, 27, 28, 29 or more nucleotides of a precursor miRNA or its processed sequence, or complement thereof, including all ranges and integers there between. In certain embodiments, the miR-3189 nucleic acid sequence or miR-3189 inhibitor contains the full-length processed miRNA sequence or complement thereof and is referred to as the "miR-3189 full-length processed nucleic acid sequence" or "miR-3189 full-length processed inhibitor sequence." In still further aspects, the miR-3189 nucleic acid comprises at least 5, 6, 7, 8, 9, 10, 11, 12, 13, 14, 15, 16, 17, 18, 19, 20, 21, 22, 23, 24, 25, 50 nucleotide segment (including all ranges and integers there between) or complementary segment of a miR-3189 that is at least 75, 80, 85, 90, 95, 98, 99 or 100% identical to SEQ ID NO:1.

miR-3189 nucleic acids or complements thereof may also include various heterologous nucleic acid sequences, i.e., those sequences not typically found operatively coupled with miR-3189 in nature, such as promoters, enhancers, and the like. The miR-3189 nucleic acid is a recombinant nucleic acid, and can be a ribonucleic acid and/or a deoxyribonucleic acid. The recombinant nucleic acid may comprise a miR-3189 or miR-3189 inhibitor expression cassette, i.e., a nucleic acid segment that expresses a nucleic acid when introduce into an environment containing components for nucleic acid synthesis. In a further aspect, the expression cassette is comprised in a viral vector, or plasmid DNA vector or other therapeutic nucleic acid vector or delivery vehicle, including liposomes and the like. In a particular aspect, the miR-3189 nucleic acid is a synthetic nucleic acid. Moreover, nucleic acids of the disclosure may be fully or partially synthetic. In certain aspects, viral vectors can be administered at $1\times10^2$, $1\times10^3$, $1\times10^4$ $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$ pfu or viral particle (vp).

In a particular aspect, the miR-3189 nucleic acid or miR-3189 inhibitor is a synthetic nucleic acid. Moreover, nucleic acids of the disclosure may be fully or partially synthetic. In still further aspects, a DNA encoding such a nucleic acid of the disclosure can be administered at 0.001, 0.01, 0.1, 1, 10, 20, 30, 40, 50, 100, 200, 400, 600, 800, 1000, 2000, to 4000 µg or mg, including all values and ranges there between. In yet a further aspect, nucleic acids of the disclosure, including synthetic nucleic acid, can be administered at 0.001, 0.01, 0.1, 1, 10, 20, 30, 40, 50, 100, to 200 µg or mg per kilogram (kg) of body weight. Each of the amounts described herein may be administered over a period of time, including 0.5, 1, 2, 3, 4, 5, 6, 7, 8, 9, 10, minutes, hours, days, weeks, months or years, including all values and ranges there between.

In certain embodiments, administration of the composition(s) can be enteral or parenteral. In certain aspects, enteral administration is oral. In further aspects, parenteral administration is intralesional, intravascular, intracranial, intrapleural, intratumoral, intraperitoneal, intramuscular, intralymphatic, intraglandular, subcutaneous, topical, intrabronchial, intratracheal, intranasal, inhaled, or instilled. Compositions of the disclosure may be administered regionally or locally and not necessarily directly into a lesion.

In certain aspects of the disclosure one or more miRNA or miRNA inhibitor may modulate a single gene. In a further aspect, one or more genes in one or more genetic, cellular, or physiologic pathways can be modulated by one or more miRNAs or complements thereof, including miR-3189 nucleic acids and miR-3189 inhibitors in combination with other miRNAs.

A further embodiment of the disclosure is directed to methods of modulating a cellular pathway comprising administering to the cell an amount of an isolated nucleic acid comprising an miR-3189 nucleic acid sequence, and most advantageously miR-3189-3p (SEQ ID NO: 2), in an amount sufficient to modulate the expression, function, status, or state of a cellular pathway. Modulation of a cellular pathway includes, but is not limited to modulating the expression of one or more genes. Modulation of a gene can include inhibiting the function of an endogenous miRNA or providing a functional miRNA to a cell, tissue, or subject. Modulation refers to the expression levels or activities of a gene or its related gene product or protein, e.g., the mRNA levels may be modulated or the translation of an mRNA may be modulated, etc. Modulation may increase or up regulate a gene or gene product or it may decrease or down regulate a gene or gene product.

Still a further embodiment includes methods of treating a patient with a pathological condition such as, but not limited to, a glioblastoma or a melanoma, comprising one or more of of: (a) administering to the patient an amount of an isolated nucleic acid comprising a miR-3189 nucleic acid sequence such as miR-3189-3p (SEQ ID NO: 2) in an amount sufficient to modulate the expression of a cellular pathway; and (b) administering a second therapy, wherein the modulation of the cellular pathway sensitizes the patient to the second therapy. A second therapy can include administration of a second miRNA or therapeutic nucleic acid, or may include various standard therapies, such as chemotherapy, radiation therapy, drug therapy, immunotherapy, and the like.

It is contemplated that any method or composition described herein can be implemented with respect to any other method or composition described herein and that different embodiments may be combined. It is specifically contemplated that any methods and compositions discussed herein with respect to miRNA molecules, miRNA, genes and nucleic acids representative of genes may be implemented with respect to synthetic nucleic acids. In some embodiments the synthetic nucleic acid is exposed to the proper conditions to allow it to become a processed or mature nucleic acid, such as a miRNA under physiological circumstances.

Also, any embodiment of the disclosure involving specific genes (including representative fragments thereof), mRNA, or miRNAs by name is contemplated also to cover embodiments involving miRNAs whose sequences are at least 80, 81, 82, 83, 84, 85, 86, 87, 88, 89, 90, 91, 92, 93, 94, 95, 96, 97, 98, 99% identical to the mature sequence of the specified miRNA.

It will be further understood that shorthand notations are employed such that a generic description of a gene or marker thereof, or of a miRNA, refers to any of its gene family members (distinguished by a number) or representative fragments thereof, unless otherwise indicated. It is understood by those of skill in the art that a "gene family" refers to a group of genes having the same coding sequence or miRNA coding sequence. Moreover, unless otherwise indicated, a shorthand notation refers to related miRNAs (distinguished by a letter). Exceptions to these shorthand notations will be otherwise identified.

Glial Tumor Cell

Inhibition of glial tumor cell proliferation finds application in decreasing the size of glial tumors and in the treatment of glioma. In this respect, the present disclosure encompasses compositions and methods for treating glioma in a subject. Accordingly, the methods of the disclosure involve administering an effective amount of miR-3189-3p (SEQ ID NO: 2) or a derivative thereof, to a subject in need thereof to treat the glioma.

Thus, some embodiments of the methods of the present disclosure target malignant gliomas. In some embodiments, the methods targets glioblastoma multiforme and it is contemplated that embodiments of the methods may be applicable to the treatment of other gliomas including, but not limited to, anaplastic astrocytoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, and atypical teratoid/rhabdoid tumor.

Subjects benefiting from treatment according to the invention include subjects with a glioma, or subjects suspected of having a glioma, as evidenced by the presence of headaches, nausea and vomiting, seizures, loss of vision, pain, weakness, numbness in the extremities, and/or cranial nerve disorders as a result of increased intracranial pressure. In particular embodiments, the glioma being treated is glioblastoma multiforme. In accordance with this embodiment, the glioblastoma multiforme can be in the brain or spinal cord.

As used herein, treatment of cancer encompasses either reducing the growth of a tumor in the subject, reducing the clinical symptoms associated with tumor growth in the subject, and/or increasing survival time as compared to a subject not receiving treatment. For the purposes of the present disclosure, "treatment" refers to both therapeutic treatment and prophylactic or preventative measures. As such, those in need of treatment include those already with the disorder as well as those prone to have the disorder (e.g., by genetic predisposition or exposure to carcinogenic agents). Subjects who can be treated in accordance with the present invention include mammals, such as humans, domestic and farm animals, and zoo, sports, or pet animals, e.g., dogs, horses, cats, cows, etc. Most advantageously, the mammal herein is human.

Methods of the disclosure include reducing or eliminating activity of one or more miRNAs in a cell comprising introducing into a cell a miRNA inhibitor (which may be described generally herein as an miRNA, so that a description of miRNA, where appropriate, also will refer to a miRNA inhibitor); or supplying or enhancing the activity of one or more miRNAs in a cell. The present disclosure also concerns inducing certain cellular characteristics by providing to a cell a particular nucleic acid, such as a specific synthetic miRNA molecule or a synthetic miRNA inhibitor molecule and in particular miR-3189-3p (SEQ ID NO: 2) and miR-3189-5p) (SEQ ID NO: 21). However, in methods of the disclosure, the miRNA molecule or miRNA inhibitor need not be synthetic. They may have a sequence that is identical to a naturally occurring miRNA or they may not have any design modifications. In certain embodiments, the miRNA molecule and/or the miRNA inhibitor are synthetic, as discussed above.

The particular nucleic acid molecule provided to the cell is understood to correspond to a particular miRNA in the cell, and thus, the miRNA in the cell is referred to as the "corresponding miRNA." In situations in which a named miRNA molecule is introduced into a cell, the corresponding miRNA will be understood to be the induced or inhibited miRNA function. It is contemplated, however, that the miRNA molecule introduced into a cell is not a mature miRNA but is capable of becoming or functioning as a mature miRNA under the appropriate physiological conditions. In cases in which a particular corresponding miRNA is being inhibited by a miRNA inhibitor, the particular miRNA will be referred to as the "targeted miRNA." It is contemplated that multiple corresponding miRNAs may be involved. In particular embodiments, more than one miRNA molecule is introduced into a cell. Moreover, in other embodiments, more than one miRNA inhibitor is introduced into a cell. Furthermore, a combination of miRNA molecule(s) and miRNA inhibitor(s) may be introduced into a cell. The inventors contemplate that a combination of miRNA may act at one or more points in cellular pathways of cells with aberrant phenotypes and that such combination may have increased efficacy on the target cell while not adversely effecting normal cells. Thus, a combination of miRNA may have a minimal adverse effect on a subject or patient while supplying a sufficient therapeutic effect, such as amelioration of a condition, growth inhibition of a cell, death of a targeted cell, alteration of cell phenotype or physiology, slowing of cellular growth, sensitization to a second therapy, sensitization to a particular therapy, and the like.

Certain embodiments of the methods include providing or introducing to a cell a nucleic acid molecule corresponding to a mature miRNA in the cell in an amount effective to achieve a desired physiological result.

Moreover, methods can involve providing synthetic or non-synthetic miRNA molecules. It is contemplated that in these embodiments, that methods may or may not be limited to providing only one or more synthetic miRNA molecules or only one or more non-synthetic miRNA molecules. Thus, in certain embodiments, methods may involve providing both synthetic and non-synthetic miRNA molecules. In this situation, a cell or cells are most likely provided a synthetic miRNA molecule corresponding to a particular miRNA and a non-synthetic miRNA molecule corresponding to a different miRNA.

A method for reducing or inhibiting cell proliferation in a cell can comprise introducing into or providing to the cell an effective amount of (i) an miRNA inhibitor molecule or (ii) a synthetic or non-synthetic miRNA molecule that corresponds to a miRNA sequence. In certain embodiments the methods involves introducing into the cell an effective amount of (i) a miRNA inhibitor molecule having a 5' to 3' sequence that is at least 90% complementary to the 5' to 3' sequence of one or more mature miRNA.

Certain embodiments of the disclosure include methods of treating a pathologic condition, in particular cancer, e.g., a glioma or a melanoma. In one aspect, the method comprises contacting a target cell with one or more of a nucleic acid, a synthetic miRNA, or an miRNA that comprises at least one nucleic acid segment having all or a portion of a miRNA sequence. The segment may be 5, 6, 7, 8, 9, 10, 11, 12, 13, 14, 15, 16, 17, 18, 19, 20, 21, 22, 23, 24, 25, 30 or more nucleotides or nucleotide analog, including all integers there between. An aspect of the disclosure includes the modulation of gene expression, miRNA expression or function or mRNA expression or function within a target cell, such as a cancer cell.

Typically, an endogenous gene, miRNA or mRNA is modulated in the cell. In particular embodiments, the nucleic acid sequence comprises at least one segment that is at least 70, 75, 80, 85, 90, 95, or 100% identical in nucleic acid sequence to one or more miRNA or gene sequence. Modulation of the expression or processing of an endogenous gene, miRNA, or mRNA can be through modulation of the processing of a mRNA, such processing including transcription, transportation and/or translation with in a cell. Modulation may also be effected by the inhibition or enhancement of miRNA activity with a cell, tissue, or organ. Such processing may affect the expression of an encoded product or the stability of the mRNA. In still other embodiments, a nucleic acid sequence can comprise a modified nucleic acid sequence. In certain aspects, one or more miRNA sequences may include or comprise a modified nucleobase or nucleic acid sequence.

It will be understood that a cell or other biological matter such as an organism (including patients) can be provided a miRNA or miRNA molecule corresponding to a particular miRNA by administering to the cell or organism a nucleic acid molecule that functions as the corresponding miRNA once inside the cell. The form of the molecule provided to the cell may not be the form that acts as an miRNA once inside the cell. Thus, it is contemplated that in some embodiments, a synthetic miRNA or a non-synthetic miRNA is provided such that it becomes processed into a mature and active miRNA once it has access to the cell's miRNA processing machinery.

In certain embodiments, methods also include targeting a miRNA to modulate in a cell or organism. The term "targeting a miRNA to modulate" means a nucleic acid of the disclosure will be employed so as to modulate the selected miRNA. In some embodiments the modulation is achieved with a synthetic or non-synthetic miRNA that corresponds to the targeted miRNA, which effectively provides the targeted miRNA to the cell or organism (positive modulation). In other embodiments, the modulation is achieved with a miRNA inhibitor, which effectively inhibits the targeted miRNA in the cell or organism (negative modulation).

In certain methods of the disclosure, there is a step of administering the selected miRNA modulator to a cell, tissue, organ, or organism (collectively "biological matter") in need of treatment related to modulation of the targeted miRNA or in need of the physiological or biological results discussed herein (such as with respect to a particular cellular pathway or result like decrease in cell viability). Consequently, in some methods of the disclosure there is a step of identifying a patient in need of treatment that can be provided by the miRNA modulator(s). It is contemplated that an effective amount of a miRNA modulator can be administered in some embodiments. In particular embodiments, there is a therapeutic benefit conferred on the biological matter, where a "therapeutic benefit" refers to an improvement in the one or more conditions or symptoms associated with a disease or condition or an improvement in the prognosis, duration, or status with respect to the disease. It is contemplated that a therapeutic benefit includes, but is not limited to, a decrease in pain, a decrease in morbidity, a decrease in a symptom. For example, with respect to cancer, it is contemplated that a therapeutic benefit can be inhibition of tumor growth, prevention of metastasis, reduction in number of metastases, inhibition of cancer cell proliferation, induction of cell death in cancer cells, inhibition of angiogenesis near cancer cells, induction of apoptosis of cancer cells, reduction in pain, reduction in risk of recurrence, induction of chemo- or radiosensitivity in cancer cells, prolongation of life, and/or delay of death directly or indirectly related to cancer.

Pharmaceutical Formulations and Delivery

Methods of the present disclosure can include the delivery of an effective amount of a miRNA or an expression construct encoding the same. An "effective amount" of the pharmaceutical composition, generally, is defined as that amount sufficient to detectably and repeatedly achieve the stated desired result, for example, to ameliorate, reduce, minimize or limit the extent of the disease or its symptoms. Other more rigorous definitions may apply, including elimination, eradication or cure of disease.

In certain embodiments, it is desired to kill cells, inhibit cell growth, inhibit metastasis, decrease tumor or tissue size, and/or reverse or reduce the malignant or disease phenotype of cells. The routes of administration will vary, naturally, with the location and nature of the lesion or site to be targeted, and include, e.g., intradermal, subcutaneous, regional, parenteral, intravenous, intramuscular, intranasal, systemic, and oral administration and formulation. Direct injection, intratumoral injection, or injection into tumor vasculature is specifically contemplated for discrete, solid, accessible tumors, or other accessible target areas. Local, regional, or systemic administration also may be appropriate. For tumors of greater than 4 cm, the volume to be administered will be about 4-10 ml (preferably 10 ml), while for tumors of less than 4 cm, a volume of about 1-3 ml will be used (preferably 3 ml).

Multiple injections can be delivered as a single dose comprising about 0.1 to about 0.5 ml volumes. Compositions of the disclosure may be administered in multiple injections to a tumor or a targeted site. In certain aspects, injections may be spaced at approximately 1 cm intervals.

In the case of surgical intervention, the present disclosure may be used preoperatively, to render an inoperable tumor subject to resection. Alternatively, the present disclosure may be used at the time of surgery, and/or thereafter, to treat residual or metastatic disease. For example, a resected tumor bed may be injected or perfused with a formulation comprising a miRNA or combinations thereof. Administration may be continued post-resection, for example, by leaving a catheter implanted at the site of the surgery. Periodic post-surgical treatment also is envisioned. Continuous perfusion of an expression construct or a viral construct also is contemplated.

Continuous administration also may be applied where appropriate, for example, where a tumor or other undesired affected area is excised and the tumor bed or targeted site is treated to eliminate residual, microscopic disease. Delivery via syringe or catherization is contemplated. Such continuous perfusion may take place for a period from about 1-2 h, to about 2-6 h, to about 6-12 h, to about 12-24 h, to about 1-2 d, to about 1-2 wk or longer following the initiation of treatment. Generally, the dose of the therapeutic composition via continuous perfusion will be equivalent to that given by a single or multiple injections, adjusted over a period of time during which the perfusion occurs.

Treatment regimens may vary as well and often depend on tumor type, tumor location, immune condition, target site, disease progression, and health and age of the patient. Certain tumor types will require more aggressive treatment. The clinician will be best suited to make such decisions based on the known efficacy and toxicity (if any) of the therapeutic formulations.

The tumor or affected area being treated may not, at least initially, be resectable. Treatments with compositions of the disclosure may increase the resectability of the tumor due to shrinkage at the margins or by elimination of certain particularly invasive portions. Following treatments, resection may be possible. Additional treatments subsequent to resection may serve to eliminate microscopic residual disease at the tumor or targeted site.

Treatments may include various "unit doses." A unit dose is defined as containing a predetermined quantity of a therapeutic composition(s). The quantity to be administered, and the particular route and formulation, are within the skill of those in the clinical arts. A unit dose need not be administered as a single injection but may comprise continuous infusion over a set period of time. With respect to a viral component of the present disclosure, a unit dose may conveniently be described in terms of mg or mg of miRNA or miRNA mimetic. Alternatively, the amount specified may be the amount administered as the average daily, average weekly, or average monthly dose.

miRNA can be administered to the patient in a dose or doses of about or of at least about 0.5, 1, 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mg or mg, or more, or any range derivable therein.

Alternatively, the amount specified may be the amount administered as the average daily, average weekly, or average monthly dose, or it may be expressed in terms of mg/kg, where kg refers to the weight of the patient and the mg is specified above. In other embodiments, the amount specified is any number discussed above but expressed as mg/m$^2$ (with respect to tumor size or patient surface area).

In some embodiments, the method for the delivery of a miRNA or an expression construct encoding such or combinations thereof is via systemic administration. However, the pharmaceutical compositions disclosed herein may also be administered parenterally, subcutaneously, directly, intratracheally, intravenously, intradermally, intramuscularly, or even intraperitoneally.

Injection of nucleic acids may be delivered by syringe or any other method used for injection of a solution, as long as the nucleic acid and any associated components can pass through the particular gauge of needle required for injection. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, mixtures thereof, and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin. In certain formulations, a water-based formulation is employed while in others, it may be lipid-based.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral, intralesional, and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety, and purity standards as required by FDA Office of Biologics standards.

Combination Treatments

In certain embodiments, the compositions and methods of the present invention can be used in combination with a second therapy to enhance the effect of the mlRNA therapy, or increase the therapeutic effect of another therapy being employed. These compositions would be provided in a combined amount effective to achieve the desired effect, such as the killing of a cancer cell and/or the inhibition of cellular hyperproliferation. This process may involve contacting the cells with the miRNA or second therapy at the same or different time. This may be achieved by contacting the cell with one or more compositions or pharmacological formulation that includes or more of the agents, or by contacting the cell with two or more distinct compositions or formulations, wherein one composition provides (1) miRNA; and/or (2) a second therapy. A second composition or method may be administered that includes a chemotherapy, radiotherapy, surgical therapy, immunotherapy, or gene therapy.

It is contemplated that one may provide a patient with the miRNA therapy and the second therapy within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

In certain embodiments, a course of treatment will last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days or more. It is contemplated that one agent may be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, any combination thereof, and another agent is given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, or any combination thereof. Within a single day (24 -h period), the patient may be given one or multiple administrations of the agent(s). Moreover, after a course of treatment, it is contemplated that there is a period of time at which no treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Various combinations may be employed. For example, but not intended to be limiting, if miRNA therapy is "A" and a second therapy is "B" some possible combinations of treatments can be: A/B/A, B/A/B, B/B/A, A/A/B, A/B/B, B/A/A, A/B/B/B, B/A/B/B, B/B/B/A, B/B/A/B, A/A/B/B, A/B/A/B, A/B/B/A, B/B/A/A, B/A/B/A, B/A/A/B, A/A/A/B, B/A/A/A, A/B/A/A, A/A/B/A, and the like. For example, but not intended to be limiting, the miR-3189-3p (SEQ ID NO: 2) (A) may be co-administered according to the present disclosure with a therapeutic agent such as fenofibrate (FF) (B) in any of the orders herein disclosed.

Administration of any compound or therapy of the present invention to a patient will follow general protocols for the administration of such compounds, taking into account the toxicity, if any, of the vector or any protein or other agent. Therefore, in some embodiments there is a step of monitoring toxicity that is attributable to combination therapy. It is expected that the treatment cycles would be repeated as necessary. It also is contemplated that various standard therapies, as well as surgical intervention, may be applied in combination with the described therapy.

Nucleic Acids

The present disclosure encompasses embodiments of nucleic acids, modified or mimetic nucleic acids, miRNAs, mRNAs, genes, and representative fragments thereof that can be labeled, employed in therapeutic applications, particularly those related to pathological conditions such as cancer, and most advantageously in gliomas and melanomas. The molecules may have been endogenously produced by a cell, or been synthesized or produced chemically or recombinantly. They may be isolated and/or purified. The name of an miRNA is often abbreviated and referred to without a prefix and will be understood as such, depending on the context. A miRNA probe designated by a suffix "5p" or "3p" can be used. "5p" indicates that the mature miRNA derives from the 5' end of the precursor and a corresponding "3p" indicates that it derives from the 3' end of the precursor. Moreover, an miRNA probe is used that does not correspond to a known human miRNA.

In some embodiments of the invention, methods and compositions involving miRNA may concern miRNA, markers (mRNAs), and/or other nucleic acids. Nucleic acids may be, be at least, or be at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length. Such lengths cover the lengths of processed miRNA, miRNA probes, precursor miRNA, miRNA containing vectors, mRNA, mRNA probes, control nucleic acids, and other probes and primers.

Preparation of Nucleic Acids

A nucleic acid may be made by any technique known to one of ordinary skill in the art, such as for example, chemical synthesis, enzymatic production, or biological production. It is particularly contemplated that miRNA probes of the invention may be advantageously, but not exclusively, chemically synthesized.

In some embodiments of the invention, miRNAs of the disclosure may be recovered or isolated from a biological sample. The miRNA may be recombinant or it may be natural or endogenous to the cell (produced from the cell's genome). It is contemplated that a biological sample may be treated in a way so as to enhance the recovery of small RNA molecules such as miRNA. Generally, methods involve lysing cells with a solution having guanidinium and a detergent.

Alternatively, nucleic acid synthesis is performed according to standard methods. See, for example, U.S. Pat. Nos. 4,704,362, 5,221,619, and 5,583,013, each of which is incorporated herein by reference. Non-limiting examples of a synthetic nucleic acid (e.g., a synthetic oligonucleotide), include a nucleic acid made by in vitro chemically synthesis using phosphotriester, phosphite, or phosphoramidite chemistry and solid phase techniques such as described in EP 266,032, incorporated herein by reference, or via deoxynucleoside H-phosphonate intermediates as described in U.S. Pat. No. 5,705,629, incorporated herein by reference. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as by polymerase chain reaction (PCR) (see for example, U.S. Pat. Nos. 4,683,202 and 4,682,195, each incorporated herein by reference), or the synthesis of an oligonucleotide described in U.S. Pat. No. 5,645,897, incorporated herein by reference. See also Sambrook et al., 2001, incorporated herein by reference).

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Recombinant methods for producing nucleic acids in a cell are well known to those of skill in the art. These include the use of vectors (viral and non-viral), plasmids, cosmids, and other vehicles for delivering a nucleic acid to a cell, which may be the target cell (e.g., a cancer cell) or simply a host cell (to produce large quantities of the desired RNA molecule). Alternatively, such vehicles can be used in the context of a cell free system so long as the reagents for generating the RNA molecule are present.

Nucleic acids may be isolated using techniques well known to those of skill in the art, though in particular embodiments, methods for isolating small nucleic acid molecules, and/or isolating RNA molecules can be employed. Chromatography is a process often used to separate or isolate nucleic acids from protein or from other nucleic acids. Such methods can involve electrophoresis with a gel matrix, filter columns, alcohol precipitation, and/or other chromatography. If miRNA from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

In particular methods for separating miRNA from other nucleic acids, a gel matrix can be prepared using polyacrylamide, though agarose can also be used. The gels may be graded by concentration or they may be uniform. Plates or tubing can be used to hold the gel matrix for electrophoresis. Usually one-dimensional electrophoresis is employed for the separation of nucleic acids. Plates are used to prepare a slab gel, while the tubing (glass or rubber, typically) can be used to prepare a tube gel. The phrase "tube electrophoresis" refers to the use of a tube or tubing, instead of plates, to form the gel. Materials for implementing tube electrophoresis can be readily prepared by a person of skill in the art or purchased.

Methods may involve the use of organic solvents and/or alcohol to isolate nucleic acids, particularly miRNA used in methods and compositions of the invention. Generally, this method for efficiently isolating small RNA molecules from cells comprises: adding an alcohol solution to a cell lysate and applying the alcohol/lysate mixture to a solid support before eluting the RNA molecules from the solid support. The amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column has worked particularly well for such isolation procedures.

An advantageous miRNA isolation process can include: a) lysing cells in the sample with a lysing solution comprising guanidinium, wherein a lysate with a concentration of at least about 1 M guanidinium is produced; b) extracting miRNA molecules from the lysate with an extraction solution comprising phenol; c) adding to the lysate an alcohol solution for forming a lysate/alcohol mixture, wherein the concentration of alcohol in the mixture is between about 35% to about 70%; d) applying the lysate/alcohol mixture to a solid support; e) eluting the miRNA molecules from the solid support with an ionic solution; and, f) capturing the miRNA molecules. Typically the sample is dried and resuspended in a liquid and volume appropriate for subsequent manipulation.

Labels and Labeling Techniques

The present disclosure further contemplates that the miRNA compositions may be labeled. It is contemplated that miRNA may first be isolated and/or purified prior to labeling. This may achieve a reaction that more efficiently labels the miRNA, as opposed to other RNA in a sample in which the miRNA is not isolated or purified prior to labeling. In some embodiments of the disclosure, the label can be non-radioactive. Generally, nucleic acids may be labeled by adding labeled nucleotides (one-step process) or adding nucleotides and labeling the added nucleotides (two-step process).

In some embodiments, nucleic acids are labeled by catalytically adding to the nucleic acid an already labeled nucleotide or nucleotides. One or more labeled nucleotides can be added to miRNA molecules. See, for example, U.S. Pat. No. 6,723,509, which is hereby incorporated by reference. In other embodiments, an unlabeled nucleotide or nucleotides is catalytically added to a miRNA, and the unlabeled nucleotide can be modified with a chemical moiety that enables it to be subsequently labeled. In embodiments of the invention, the chemical moiety is a reactive amine such that the nucleotide is an amine-modified nucleotide. Examples of amine-modified nucleotides are well known to those of skill in the art, many being commercially available such as from Ambion, Sigma, Jena Bioscience, and TriLink.

The issue for labeling miRNA is how to label the already existing molecule. For example, the use of an enzyme capable of using a di- or tri-phosphate ribonucleotide or deoxyribonucleotide as a substrate for its addition to a miRNA is contemplated. Labeling may involve using a modified di- or tri-phosphate ribonucleotide, which is added to the 3' end of a miRNA. Enzymes capable of adding such nucleotides include, but are not limited to, poly (A) polymerase, terminal transferase, and polynucleotide phosphorylase. In some embodiments of the disclosure, a non-ligase enzyme can be employed. Terminal transferase can catalyze the addition of nucleotides to the 3' terminus of a nucleic acid. Polynucleotide phosphorylase can polymerize nucleotide diphosphates without the need for a primer.

Labels on miRNA may be colorimetric (includes visible and UV spectrum, including fluorescent), luminescent, enzymatic, or positron emitting (including radioactive). The label may be detected directly or indirectly. Radioactive labels include $^{125}$I, $^{32}$P, $^{33}$P, and $^{35}$S. Examples of enzymatic labels include alkaline phosphatase, luciferase, horseradish peroxidase, and β-galactosidase. Labels can also be proteins with luminescent properties, e.g., green fluorescent protein and phycoerythrin.

The colorimetric and fluorescent labels contemplated for use as conjugates include, but are not limited to, Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB. Specific examples of dyes include, but are not limited to, those identified above and the following: Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides are available from Molecular Probes, and these include, Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences, such as Cy3-UTP and Cy5-UTP.

Examples of fluorescently labeled deoxyribonucleotides include Dinitrophenyl (DNP)-11-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP.

It is contemplated that nucleic acids may be labeled with two different labels. Furthermore, fluorescence resonance energy transfer (FRET) may be employed in methods of the invention. Alternatively, the label may not be detectable per se, but indirectly detectable or allowing for the isolation or separation of the targeted nucleic acid. For example, the label could be biotin, digoxigenin, polyvalent cations, chelator groups and the other ligands, include ligands for an antibody.

A number of techniques for visualizing or detecting labeled nucleic acids are readily available. Such techniques include: microscopy, arrays, Fluorometry, Light cyclers or other real time PCR machines, FACS analysis, scintillation counters, Phosphoimagers, Geiger counters, MRI, CAT, antibody-based detection methods (Western blots, immunofluorescence, immunohistochemistry), histochemical techniques, HPLC (Griffey et al., 1997), spectroscopy, capillary gel electrophoresis (Cummins et al., 1996), spectroscopy; mass spectroscopy; radiological techniques; and mass balance techniques.

When two or more differentially colored labels are employed, fluorescent resonance energy transfer (FRET) techniques may be employed to characterize association of one or more nucleic acid. Furthermore, a person of ordinary skill in the art is well aware of ways of visualizing, identifying, and characterizing labeled nucleic acids, and accordingly, such protocols may be used as part of the invention. Examples of tools that may be used also include fluorescent microscopy, a BioAnalyzer, a plate reader, Storm (Molecular Dynamics), Array Scanner, FACS (fluorescent activated cell sorter), or any instrument that has the ability to excite and detect a fluorescent molecule.

Kits

Any of the compositions described herein may be comprised in a kit. A kit may include reagents for preparation of samples from blood samples. The kit may further include reagents for creating or synthesizing the miRNA probes according to the disclosure. The reagents of the kits can be in suitable container means. The kits may further include various supports, such as glass, nylon, polymeric beads, and the like, and/or reagents for coupling any probes and/or target nucleic acids. It may also include one or more buffers, such as reaction buffer, labeling buffer, washing buffer, or a hybridization buffer, compounds for preparing the miRNA probes, and components for isolating miRNA.

Kits for implementing methods of the disclosure described herein are specifically contemplated. In some embodiments, there are kits for preparing miRNA. In these embodiments, a kit can comprise, in suitable container means, 1, 2, 3, 4, 5, 6, 7, 8, 9, 10, 11, 12 or more of the following: (1) poly(A) polymerase; (2) unmodified nucleotides (G, A, T, C, and/or U); (3) a modified nucleotide (labeled or unlabeled); (4) poly(A) polymerase buffer; and, (5) at least one microfilter; (6) a label that can be attached to a nucleotide; (7) at least one miRNA probe; (8) reaction buffer; (9) a miRNA array or components for making such an array; (10) acetic acid; (11) alcohol; (12) solutions for preparing, isolating, enriching, and purifying miRNAs or miRNA probes or arrays. Other reagents include those generally used for manipulating RNA, such as formamide, loading dye, ribonuclease inhibitors, and DNase.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present disclosure also will typically include a means for containing the nucleic acids, and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly advantageous.

However, the components of the kit may be provided as dried powder(s). When reagents and/or components are provided as a dry powder, the powder can be reconstituted by the addition of a suitable solvent. It is envisioned that the solvent may also be provided in another container means. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 µg or at least or at most those amounts of dried dye are provided in kits of the disclosure.

Such kits may also include components that preserve or maintain the miRNA or that protect against its degradation. Such components may be RNAse-free or protect against RNAses. Such kits generally will comprise, in suitable means, distinct containers for each individual reagent or solution.

A kit most advantageously will also include instructions for employing the kit components as well the use of any other reagent not included in the kit. Instructions may include variations that can be implemented.

Kits of the disclosure may also include one or more of the following: Control RNA; nuclease-free water; RNase-free containers, such as 1.5 ml tubes; RNase-free elution tubes; PEG or dextran; ethanol; acetic acid; sodium acetate; ammonium acetate; guanidinium; detergent; nucleic acid size marker; RNase-free tube tips; and RNase or DNase inhibitors. It is contemplated that such reagents are embodiments of kits of the disclosure. Such kits, however, are not limited to the particular items identified above and may include any reagent used for the manipulation or characterization of miRNA.

One aspect of the disclosure, therefore, encompasses embodiments of a method for decreasing at least one of the proliferation and the migration of a cancer cell, the method comprising contacting a cancer cell with an effective amount of a pharmaceutically acceptable composition comprising a microRNA (miRNA), wherein said miRNA has a nucleotide sequence having at least 80% sequence similarity to the nucleotide sequence SEQ ID NO: 2, thereby decreasing at least one of the proliferation and migration of the cancer cell as compared to a control.

In some embodiments of this aspect of the disclosure, the cancer cell can be a glial tumor cell, a melanoma cell, or a breast cancer cell.

In some embodiments of this aspect of the disclosure, the glial tumor cell can be an astrocytoma tumor cell, an ependymal tumor cell, a glioblastoma multiforme tumor cell, or a primitive neuroectodermal tumor cell.

In some embodiments of this aspect of the disclosure, the glioblastoma multiforme can be located in the brain or the spinal cord of the subject.

In some embodiments of this aspect of the disclosure, the miRNA can reduce the expression of at least one of p63RoGEF and SF3B2 splicing factor in the cancer cell, or modulate the effect of MYC in the cancer cell.

In some embodiments of this aspect of the disclosure, the cancer cell can be an isolated cancer cell, a cultured cell, a cell in a tissue of an animal or human patient, or progeny thereof.

In embodiments of this aspect of the disclosure, the miRNA can have a nucleotide sequence having at least 85%, 90%, 93%, 95%, 96%, 97%, 98%, 99%, or 100% sequence similarity to the nucleotide sequence of SEQ ID NO: 2.

In some embodiments of this aspect of the disclosure, the miRNA can have a nucleotide sequence having at least 95%, sequence similarity to the nucleotide sequence SEQ ID NO: 2.

In some embodiments of this aspect of the disclosure, the miRNA can have a nucleotide sequence having at least 97%, sequence similarity to the nucleotide sequence of SEQ ID NO: 2.

In some embodiments of this aspect of the disclosure, the miRNA can have the nucleotide sequence of SEQ ID NO: 2.

Another aspect of the disclosure encompasses embodiments of method for treating a cancer comprising administering to an animal or human subject in need thereof an effective amount of a pharmaceutically acceptable composition comprising a microRNA (miRNA), wherein said miRNA has a nucleotide sequence having at least 80% sequence similarity to the nucleotide sequence of SEQ ID NO: 2, thereby decreasing at least one of the proliferation and migration of the cancer cell as compared to a control.

In some embodiments of this aspect of the disclosure, the cancer can be a glial tumor, melanoma cell, or a breast cancer cell.

In some embodiments of this aspect of the disclosure, the glial tumor cell can be an astrocytoma tumor cell, an ependymal tumor cell, a glioblastoma multiforme tumor cell, or a primitive neuroectodermal tumor cell.

In some embodiments of this aspect of the disclosure, the glioblastoma multiforme can be located in the brain or the spinal cord of the subject.

In some embodiments of this aspect of the disclosure, the miRNA reduces the expression of at least one of p63RoGEF and SF3B2 splicing factor in the cancer cell, or modulates the effect of MYC in the cancer cell.

In some embodiments of this aspect of the disclosure, the miRNA can have a nucleotide sequence having at least 85%, 90%, 93%, 95%, 96%, 97%, 98%, 99%, or 100% sequence similarity to the nucleotide sequence of SEQ ID NO: 2.

In some embodiments of this aspect of the disclosure, the miRNA can have the nucleotide sequence of miR-3189-3p according to SEQ ID NO: 2.

In some embodiments of this aspect of the disclosure, the pharmaceutically acceptable composition can be administered to the animal or human subject intravenously, subcutaneously, or intratumorally.

In some embodiments of this aspect of the disclosure, the pharmaceutically acceptable composition can be formulated to deliver the miRNA across the blood-brain barrier or to deliver the miRNA as a nucleic acid expression product to the cells of the cancer.

Yet another aspect of the disclosure encompasses embodiments of a composition comprising an oligonucleotide capable of hybridizing under physiological conditions to a nucleotide sequence that is the complement of the nucleotide sequence SEQ ID NO: 2, or the complement thereof, and in an amount effective to reduce at least one of the proliferation and the migration of a cancer cell in a patient administered said composition, and a pharmaceutically acceptable carrier.

In some embodiments of this aspect of the disclosure, the oligonucleotide can have a nucleotide sequence having at least 90% similarity to the nucleotide sequence SEQ ID NO: 2.

In some embodiments of this aspect of the disclosure, the oligonucleotide can have a nucleotide sequence SEQ ID NO: 2.

In some embodiments of this aspect of the disclosure, the composition can further comprise a therapeutic agent therapeutically effective against the cancer cell.

In some embodiments of this aspect of the disclosure, the cancer cell can be a glioblastoma cell, a melanoma cell, or a breast cancer cell.

Still another aspect of the disclosure encompasses embodiments of a kit comprising at least one of: (a) reagents for preparation of samples from blood samples; (b) reagents for creating or synthesizing an miRNA oligonucleotide having at least 80% sequence similarity to the nucleotide sequence of SEQ ID NO: 2, wherein said reagents are in suitable container means, and wherein said reagents are packaged either in aqueous media or in lyophilized form, and instructions for employing the kit components for the synthesis or therapeutic use of the miRNA oligonucleotide in a patient in need thereof.

While the embodiments of the present disclosure are described with reference to various implementations and exploitations, it will be understood that these embodiments are illustrative and that the scope of the disclosures is not limited to them. Many variations, modifications, additions, and improvements are possible. Further still, any steps described herein may be carried out in any desired order, and any desired steps may be added or deleted. Support for the present disclosure and additional embodiments of the present disclosure may be found in the attached documents all of which are expressly incorporated herein in their entirety by reference hereto. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

The meaning of abbreviations is as follows: "sec" means second(s), "min" means minute(s), "h" means hour(s), "d" means day(s), "4" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kb" means kilobase(s).

EXAMPLES

Example 1

Cell Culture, Transfection, and Reagents: LN-229 and U87MG cells were obtained from the American Type Culture Collection (ATCC, Manassas, Va.) and cultured under standard growth conditions. Fenofibrate was from Sigma (St. Louis, Mo.) and in all experiments was used at the concentration of 50 µM. miR-3189-3pmirVana miRNA mimic and miR-3189-3pmirVana miRNA inhibitor (anti-miR-3189-3p (SEQ ID NO: 22)) were purchased from Life Technologies.

For transfection experiments, cells were seeded at a density of $4 \times 10^5$ cells/60 mm dish or $2.5 \times 10^4$ cells/well in 12-well plates, and transfected using Lipofectamine 2000 (Life Technologies, Grand Island, N.Y.) per manufacturer's instructions. SF3B2 and p63RhoGEF siRNAs and controls were purchased from Santa Cruz (Santa Cruz, Calif.), and were used at the final concentration of 10 nM. Human PPARα siRNA was the ON-TARGET plus SMART pool from Thermo Scientific Dharmacon (Lafayette, Colo.), and it was used at the final concentration of 100 nM. The PPARα inhibitor WY146,43 was from Cayman Chemical (St. Louis, Mo.). For the transient transfection experiments, cells were seeded at a density of $4 \times 10^5$ cells/60 mm dish or $2.5 \times 10^4$ cells/well in 12-well plates, and transfected using Lipofectamine 2000 reagent (Life Technologies) per manufacturer's instructions.

Example 2

Quantitative RT-PCR: Total RNA was isolated using the miRVana miRNA extraction kit (Ambion, Austin, Tex., USA). RNA was reverse transcribed using the High Capacity cDNA Reverse Transcription kit for mRNAs or TaqMan assays for microRNAs (Applied Biosystems, Carlsbad, Calif.). Quantitative real-time PCR was performed in duplicate using a Roche LightCycler 480 Real-Time PCR System (Indianapolis, Ind., USA). Each sample was normalized using GAPDH or RNU6B control (ΔCt) and relative quantification of gene expression was calculated using the comparative Ct ($2^{-\Delta\Delta Ct}$) method, as described in (Eletto et al., (2008) *J. Cell. Physiol.* 216: 764-770; Pacifici et al., (2013)

J. Cell. Physiol. 228: 1070-1075; Rom et al., (2010) *FASEB J.* 24: 2292-2300 incorporated herein by reference in their entireties). For the clinical samples relative quantification was represented as 1/ΔCt to maintain real differences in Ct values between samples.

Example 3

Western Blot Analysis: Cells were collected by gently scraping in the presence of PBS (Gibco, Life Technologies), followed by centrifugation and disruption of the cell pellet in lysis buffer (50 mM HEPES, pH 7.5, 150 mM NaCl, 1.5 mM $MgCl_2$, 1 mM EGTA, pH 8.4, 10% glycerol, 1% Triton X-100, 1 mM PMSF, 1 mM sodium orthovanadate ($NA_3VO_4$), Phosphatase and Protease Inhibitor Cocktails (Sigma). Whole-cell lysates (30 to 70 μg) were separated on a 4-15% SDS-PAGE gel (Bio-Rad, Hercules, Calif.). GDF15 and E2F-1 antibodies were purchased from Cell Signaling Technology (Beverly, Mass.). The antibody to detect p63RhoGEF was obtained from GeneTex (Irvine, Calif.). GDF15 antibody was purchased from R&D Systems (Minneapolis, Minn.), and anti-GRB2 was from BD Transduction Laboratories (San Jose, Calif.). SF3B2 and 14-3-3ζ antibodies were obtained from Santa Cruz Biotechnology.

Example 4

ELISA Assay: Mature GDF15 was detected in the cell culture medium using the GDF15 Quantikine ELISA kit from R&D Systems (Minneapolis, Minn.), according to the manufacturer's instructions. Sample absorbance was measured at 450 nm using a Bio-Rad Benchmark Plus microplate reader.

Example 5

RNA-Binding Protein Immunoprecipitation (RIP): RIP assay was performed using Argonaute 2 (Ago2) antibody from Millipore (RIPAb+Ago2 RIP). This kit included negative control mouse IgG antibody and control primers specific for human FOS, which were utilized for the optimization of Ago2-IP in the cellular model. The RIP Ago-IP was performed essentially as previously described (Curtale et al., (2013) *Proc. Nat. Acad. Sci. U.S.A.* 110: 11499-11504). In brief, $10 \times 10^6$ LN-229 cells were used for Ago2-IP and for the IgG isotype control; $2 \times 10^6$ cells were used for the extraction of total RNA and for total protein lysates. The cell monolayer was washed twice with cold PBS, and lysed in 500 μl of Lysis Buffer (150 mM KCl, 25 mM Tris-HCl pH 7.4, 5 mM EDTA, 0.5% NP40, 5 mM DTT) supplemented with 10 mM Protease Inhibitor Cocktail, 10 mM PMSF, 10 mM Phosphatase Inhibitor, 10 mM $Na_3VO_4$ and 100 U/ml RNase Inhibitor (Applied Biosystems). After 30 min of incubation on ice, lysates were centrifuged for 30 min at 14,000 rpm at 4° C. in a microcentrifuge. 30 μL of Protein A/G Magnetic Beads (Pierce, Thermo Scientific, Waltham, Mass.) were washed three times with Blocking Solution (0.5% BSA dissolved in DPBS+/+) and incubated for 1 h at 4° C. with 5 μg of anti-Ago2 mouse monoclonal IgG1κ or with isotype IgG1κ control antibodies (Millipore). The immunocomplexes were washed three times with Blocking Solution. Immunoprecipitations with specific lysates were carried out overnight at 4° C. Next day, the immunocomplexes were washed three times with Lysis Buffer supplemented with the inhibitors. Left-over IP samples before the first wash were collected to determine the efficiency of Ago2 depletion from the cellular lysate. After the last wash, immunocomplexes were resuspended in 40 μL of Lysis Buffer of which 20 μL were used for the RNA extraction and 20 μL for Western blot analysis. RNA extraction from the beads and from the left-over samples was followed by reverse transcription and qRT-PCR, which were performed as described above.

Example 6

Cloning of the p63RhoGEF and SF3B2 Open Reading Frames: Total RNA was isolated from LN-229 cells and reverse transcribed to cDNA using the High Capacity cDNA Reverse Transcription kit containing random hexamers. The cDNA sequence corresponding to the open reading frame (ORF) of p63RhoGEF was PCR amplified. The primers used were: forward, 5'-GGTGGAATTCTGCAGATAT-GCGGGGGGGGCACAAA (SEQ ID NO: 3) and reverse, 5'-CCACTGTGCTGGATTTACAGCTCATCTTCATCCA-GCTTGG (SEQ ID NO: 4). Sequences compatible with pcDNA3.1(+) are underlined.

Next, the pcDNA3.1(+) vector was digested with EcoRV. This vector and the PCR product (above) were digested with the Klenow fragment of DNA polymerase I to generate single-stranded 3'-overhangs compatible between the two DNA molecules. These products were annealed by incubating at incremental reducing temperatures from 95° C. to 45° C. using a PCR cycler (Bio-Rad). The ORF sequence corresponding to the SF3B2 gene was also cloned into the pcDNA3.1(+) vector using the approach described above. The primers used were: forward, 5'-GGTGGAATTCTGCA-GATATGGCGACGGAGCATCCC (SEQ ID NO: 5) and reverse, 5'-CCACTGTGCTGGATCTAAAACTT-GAACTCCTTATATTTCTTGCTGCC (SEQ ID NO: 6). Sequences compatible with pcDNA3.1(+) are underlined.

Example 7

Cloning for microRNA Functional Analysis: The genomic sequence corresponding to the 3'UTR of p63RhoGEF was PCR amplified from LN-229 cells. This PCR product was ligated into the multiple cloning sites downstream of the Renilla luciferase reporter gene in the psiCHECK-2 vector (Promega, Madison, Wis.). This vector also contains a firefly luciferase reporter sequence, which allows for normalization of transfection efficiency. The primers used were: forward, 5'-CCGCTCGAGCTGGTGAAAACCATGGGGGTG (SEQ ID NO: 7), containing the XhoI restriction site (underlined) and reverse, 5'-ATAAGAATGCGGCCGCGCAGC-CTCGGTGATATAACAAAACC (SEQ ID NO: 8), containing the NotI restriction site (underlined). The genomic sequence corresponding to the 3'UTR of SF3B2 was also cloned into the psiCHECK-2 vector. The primers used were: forward, 5'-CCGCTCGAGTTCAAGTTTTAGGTCCCCT-CAC (SEQ ID NO: 9), containing the XhoI restriction site (underlined) and reverse, 5'-ATAAGAATGCGGCCGCG-GAGGCTCAGGAGTGTTAAATATTCATCTC (SEQ ID NO: 10) containing the NotI restriction site (underlined).

Mutations of the miR-3189-3p (SEQ ID NO: 2) putative binding sites in the p63RhoGEF and SF3B2 3'UTR sequences were generated using the QuikChange Lightning site-directed mutagenesis kit (Agilent Technologies, Santa Clara, Calif.) using the respective psiCHECK2/3'UTR plasmids as a template. The oligonucleotides for the mutagenesis of p63RhoGEF sites were as follows: site 1 forward, 5'-TCAGCCGCCTATTCCCCTTCCAGCTTCAGGGCA-GTCCT (SEQ ID NO: 11), site 2 forward, 5'-TGGAGGA-GAACACCTAGACCCTTCCACTTTTTTCTGC- CCAAGGAAC (SEQ ID NO: 12), and site 3 forward, 5'-CCCAAGGACTTTTTTCTGCCCTTCCAACACA-GTTTCCTTCAGCTCC (SEQ ID NO: 13). The oligonucleotides for the mutagenesis of SF3B2 sites were: site 1 forward, 5'-GAACCACCTCTCCCGCAGTTCCCTTC-CACTTGTCATTTCATGTTCTTATT (SEQ ID NO: 14), and site 2 forward, 5'-GACCTGTTTTGTAAATAAAGCT-GTTTCCCTTCCAAAGAGATGAATATTTAACACTCCT-GAGC (SEQ ID NO: 15). Mutated bases in the miR-3189-3p (SEQ ID NO: 2) binding sites in SEQ ID Nos: 11-15 are underlined. The reverse oligonucleotide primers were complementary to the forward primers.

Example 8

Dual Luciferase Assay: LN-229 cells were plated at a density of $8\times10^4$ cells/well in a 12-well plate and transfected with psiCHECK-2 vector expressing target 3'UTR (160 ng/well) alone, target 3'UTR with miR-3189-3p (SEQ ID NO: 2) mimic (30 nM), or target 3'UTR with miRNA mimic and anti-miR-3189-3p (SEQ ID NO: 22) using Lipofectamine 2000. After 24 h, cells were harvested and lysates were assayed for luciferase activity with the Dual-Luciferase Reporter Assay System (Promega) using a Synergy 2 microplate reader (BioTek Instruments, Inc., Winooski, Vt.). Relative units of Renilla luciferase activity were normalized to the firefly luciferase internal control in each sample. Experiments were performed in duplicate.

Example 9

Cell Proliferation Assay: LN-229 or U87MG cells were plated at a density of $2.5\times10^4$ cells/well in a 12-well plate and transfected with mock or miR-3189-3p (SEQ ID NO: 2) mimic+/−anti-miR-3189-3p (SEQ ID NO: 22). At 72 h after transfection, cells were incubated with medium containing 3-(4,5-dimethylthiazol-2-yl)-5-(3-carboxymethoxyphenyl)-2-(4-sulfophenyl)-2H-tetrazolium (MTS) reagent (Promega) diluted according to manufacturer's instructions. Cells were then incubated at 37° C. for 30-60 min and absorbance was measured at a wavelength of 490 nm using a Bio-Rad Benchmark Plus microplate reader.

Example 10

Cell Cycle Analysis: Cells were collected 48 h after transfection and fixed in 70% ethanol overnight at −20° C. Cells were then centrifuged at 300×g, resuspended in 150 µL of Guava Cell Cycle reagent (Guava Technologies, Hayward, Calif.), and stained for 45 min at 25° C. while protected from light. Cells were counted by flow cytometry using a FACSAria (BD Biosciences) in the Comprehensive Alcohol Research Center (CARC) Analytical Core Laboratory at LSU Health Sciences Center. Cell cycle distribution was evaluated using the ModFit LT program (Verity Software House, Topsham, Me.).

Example 11

Scratch Assay: LN-229 or U87MG cells were transfected with miR-3189-3p (SEQ ID NO: 2) and plated in a 35 mm glass bottom dish (MatTek Corporation, Ashland, Mass.) at a density of $1.8\times10^5$ cells/dish. The scratch assay was performed by moving a pipette tip across the cell monolayer. Migration into the cell-free area was monitored for up to 24 h using live cell time-lapse imaging (VivaView FL incubator fluorescent microscope, Olympus, Center Valley, Pa.).

Example 12

Subcutaneous Injection of Mice with LN-229-mCherry Glioblastoma Cells: Female Fox1nu athymic nude mice at 6-8 weeks of age (Harlan Laboratories, Inc., Indianapolis, Ind.) were injected subcutaneously with $2\times10^6$ LN-229 glioblastoma cells stably expressing the mCherry fluorescent protein and mock-transfected, or transfected with miR-3189-3p (SEQ ID NO: 2) mimic. All experiments were performed in accordance with institutional ethical guidelines.

Example 13

Intracranial Injection of Mice with U87MG-Luciferase Glioblastoma Cells: Intracranial implantation of mice was performed as previously described (Wilk et al., (2014) *Mol. Cell Biol.* 35: 182-198; Marrero et al., (2014) *Neoplasia* 16: 874-882, incorporated herein by reference in their entireties). Briefly, female nude-Foxnlnu athymic mice, 6-8 weeks of age (Harlan Laboratories) were anesthetized with 4% isoflurane and secured in a stereotaxic head frame (Harvard Apparatus, Holliston, Mass.). The tumor cells ($3\times10^4$ in 2 µL of artificial cerebrospinal fluid) were injected into the left striatum through a burr hole in the skull using a 10 µl Hamilton syringe.

Example 14

In Vivo Imaging of Tumor Xenografts: In vivo growth of LN-229/mCherry and U87MG/luciferase tumors was monitored by biophotonic imaging using a Xenogen IVIS 200 system (Xenogen, Palo Alto, Calif.). Prior to imaging, mice bearing U87MG/luciferase tumors received an intraperitoneal injection of 100 µL of D-luciferin (30 mg/ml solution) and were anesthetized by 3% isoflurane inhalation. Anesthesia was sustained at 1.5% isoflurane inside the imaging chamber using nose cones. Images were captured and quantified with Xenogen Living Image 4.1 software based on equivalent regions of interest over the lower dorsal flank or cranium of the mouse. Image intensities were expressed as photon flux per second, square centimeter and steradian (photons/sec/cm$^2$/sr).

Example 15

Statistical Analysis: Data are presented as mean±SD. Comparison between two experimental groups was performed using the Student's t-test. One way ANOVA was used to compare three or more groups. P-values ≤0.05 were considered statistically significant.

Example 16

MiR-3189-3p is Downregulated in Glial Tumors and Regulates Growth and Migration of Glioblastoma Cells: Formalin-fixed paraffin-embedded (FFPE) tissue samples from astrocytomas, glioblastomas and normal brains were utilized for total RNA isolation and were subjected to quantitative RT-PCR. FIG. 1A shows significantly less miR-3189-3p (SEQ ID NO: 2) levels in astrocytoma and glioblastoma tissue samples compared to controls (p<0.05 and p<0.001, respectively), with a trend of down-regulation that correlated with the tumor progression.

Figure 1B:
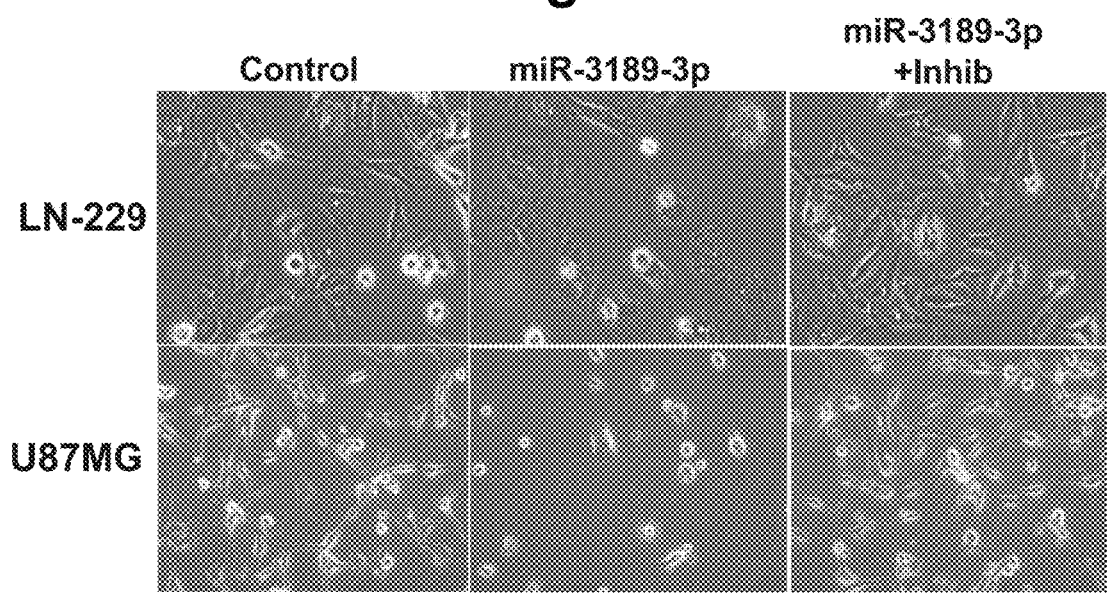
Figure 1C:
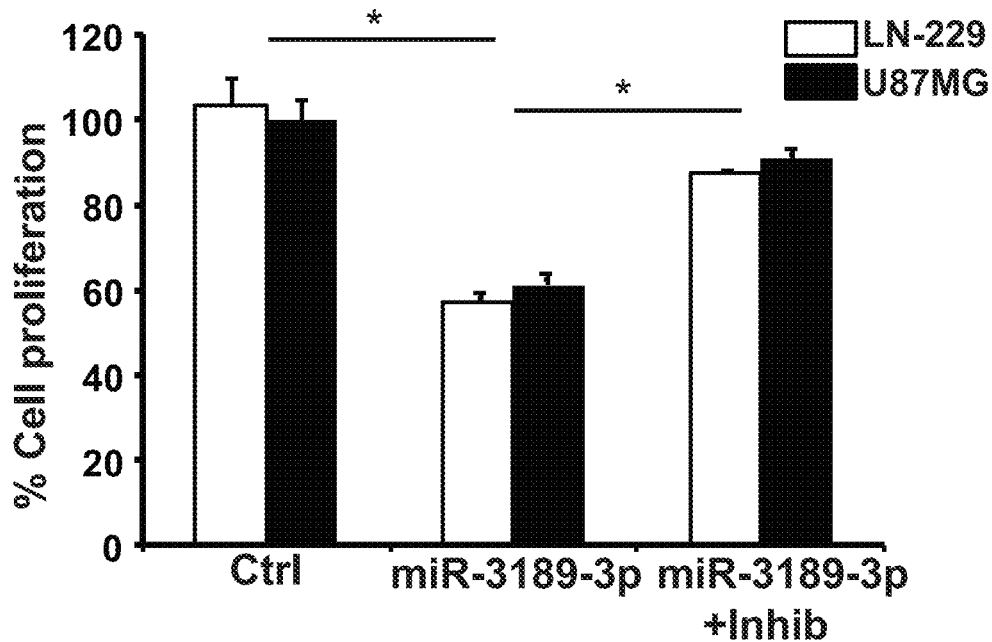
Figure 1D:
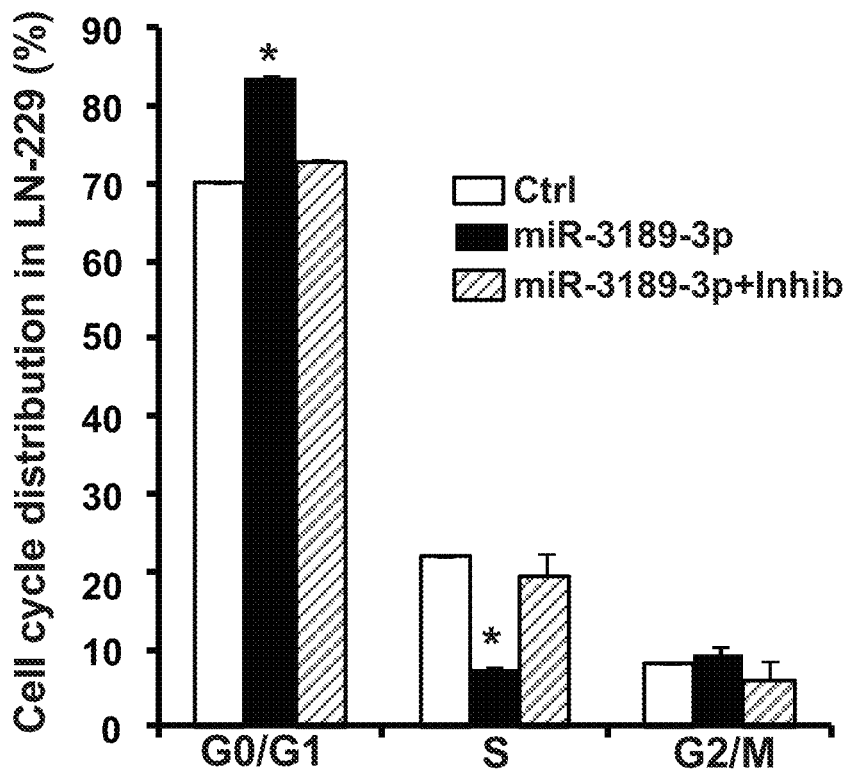
Figure 1E:
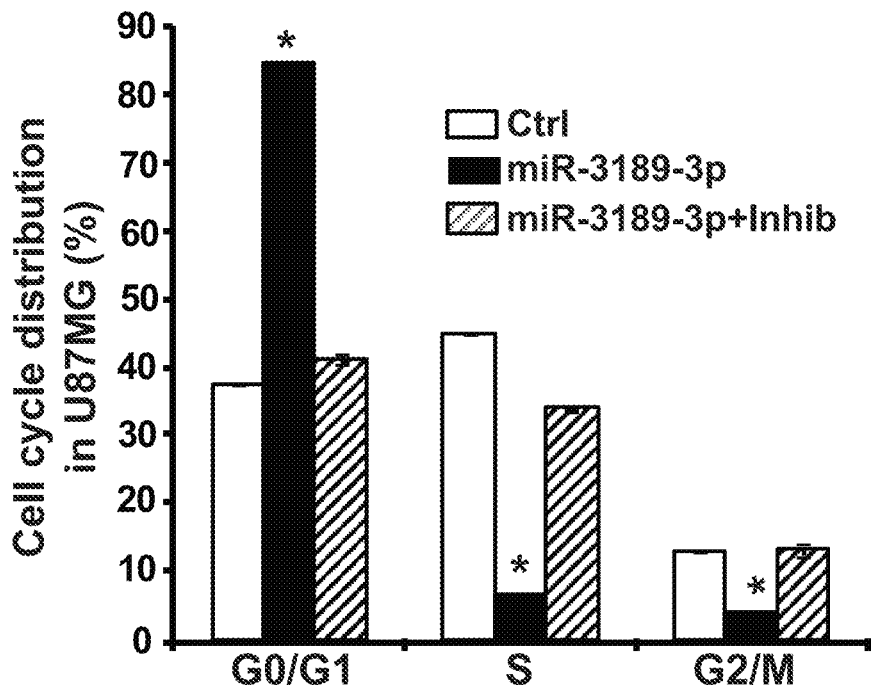

The function of miR-3189-3p (SEQ ID NO: 2) in cell growth and migration of the human glioblastoma cell lines LN-229 and U87MG was then evaluated. At 48 h post-transfection morphology of miR-3189-3p (SEQ ID NO: 2) expressing cells was visibly altered, presenting a more polygonal shape when compared to the typical spindle-shaped cells under normal growth conditions or when both miR-3189-3p (SEQ ID NO: 2) and anti-miR-3189-3p (SEQ ID NO: 22) were co-expressed (FIG. 1B). In addition, the expression of miR-3189-3p (SEQ ID NO: 2) resulted in a 50% reduction in cell proliferation (% decrease in cell number over control; FIG. 1C), accompanied by a significant, 40% reduction in the S phase, as determined by cell cycle distribution analysis (FIGS. 1D and 1E). No significant changes where observed when miR-3189-3p (SEQ ID NO: 2) was co-transfected with anti-miR-3189-3p (SEQ ID NO: 22), and the cells expressing this inhibitor behaved essentially as the control, mock-transfected cells. Similarly, transfection with miR-3189-5p (SEQ ID NO: 21) did not elicit changes in cell morphology, nor inhibited cell proliferation and migration. To minimize possible off-target effects this set of experiments was repeated using another commercially available miR-3189-3p (SEQ ID NO: 2) mimic (mission miRNA mimic, Sigma) and obtained the same results.

Figure 1F:
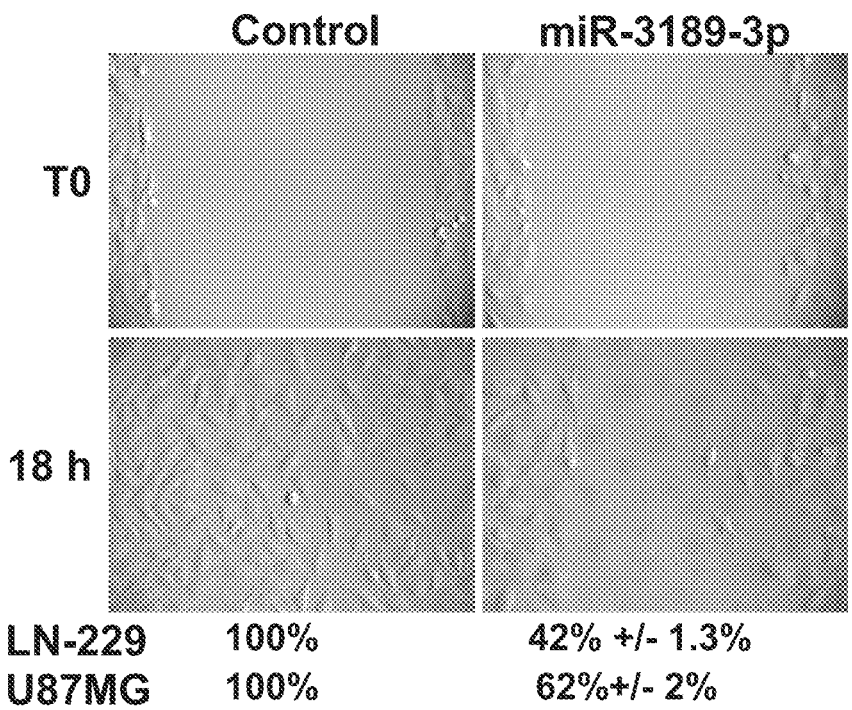

Since glioblastoma cells are characterized by high migratory potentials, possible effects of this microRNA on cell migration was evaluated using scratch assay and by monitoring both cell locomotion and cell division using time-lapse imaging. FIG. 1F shows representative images for LN-229 cells. While control cells populated the entire scratched area in 18 h, LN-229 cells transfected with miR-3189-3p (SEQ ID NO: 2) covered only 42% of the scratched surface in the same time (FIG. 1F). Although with decreased efficiency compared to LN-229 cells, miR-3189-3p (SEQ ID NO: 2) expression inhibited also U87MG cell migration and after 18 h from transfection cells covered only 62% of the available surface. Please note that both decreased cell motility and decreased cell proliferation contributed to delayed invasion of the cell-free space.

Example 17

SF3B2 and p63RhoGEF are Targets of miR-3189-3p (SEQ ID NO: 2): According to microRNA gene target predictions (TargetScan.org), the splicing factor SF3B2 and the Rho guanine nucleotide exchange factor 25, ARHGEF25 (also known as p63RhoGEF) are the top targets of miR-3189-3p (SEQ ID NO: 2) and were chosen for validation studies. The direct contribution of miR-3189-3p (SEQ ID NO: 2) to SF3B2 and p63RhoGEF mRNA and protein levels was evaluated in miR-3189-3p (SEQ ID NO: 2) transfected LN-229 and U87MG cells by quantitative RT-PCR and Western blot analyses. In comparison to controls, nearly 5-fold and 2.5-fold lower levels of SF3B2 mRNA and p63RhoGEF mRNA were detected in miR-3189-3p (SEQ ID NO: 2) expressing cells, respectively (FIG. 2A).

Downregulation of these two transcripts was counteracted by overexpressing the anti-miR-3189-3p (miR-3189-3p inhibitor; (SEQ ID NO: 22)), further supporting the presence of miR-3189-3p (SEQ ID NO: 2)-specific regulation. A remarkable down-regulation of SF3B2 and p63RhoGEF at the translational level was confirmed by Western blots in cells transfected with miR-3189-3p (SEQ ID NO: 2), when compared to control or cells co-transfected with the anti-miR-3189-3p (SEQ ID NO: 22) (FIG. 2B). Notably, the down-regulation SF3B2 and p63RhoGEF was more pronounced in LN-229 cells, and this cell line was selected for the next experiments.

There are two putative binding sites for miR-3189-3p (SEQ ID NO: 2) in the 3'UTR sequence of SF3B2 mRNA, one conserved (MS2) and one non-conserved (MS1) (FIG. 2C), and their expression was tested by a luciferase-based reporter assay (FIG. 2D). A reduction of approximately 75% of luminescence was observed in cells expressing miR-3189-3p (SEQ ID NO: 2), and again this inhibition was almost completely alleviated in the presence of anti-miR-3189-3p (SEQ ID NO: 22). In addition, site directed mutagenesis of the microRNA binding sequences in the 3'UTR showed a slightly different, although cumulative, inhibitory activity.

The conserved microRNA binding site (MS2) appeared to be slightly more effective in microRNA-induced transcript degradation as mutation of this site significantly reversed a decrease in luciferase signal (compare MS1 and MS2). As expected, mutation of both microRNA binding sequences (double mutation, DM) abrogated inhibition by miR-3189-3p (SEQ ID NO: 2). The p63RhoGEF 3'UTR contains three putative binding sites for miR-3189-3p (SEQ ID NO: 2), one conserved and two non-conserved (FIG. 2E). Similarly to SF3B2 3'UTR, p63RhoGEF 3'UTR (FIG. 2F) was tested. Also here, the inhibition was efficiently reverted either in the presence of anti-miR-3189-3p (SEQ ID NO: 22) or by mutating the three binding sequences (triple mutation, TM) of the p63RhoGEF 3'UTR. Quantitatively, one of the non-conserved binding sites did not appear to be required for miR-3189-3p (SEQ ID NO: 2)-induced gene regulation, since mutation of this site (MS1) failed to revert the expected inhibition. Conversely, mutation of the other two microRNA binding sites (MS2 and MS3), one conserved and one non-conserved, showed a stronger and cumulative reversion of inhibition by miR-3189-3p (SEQ ID NO: 2) (FIG. 2F).

Example 18

Role of SF3B2 and p63RhoGEF in the Inhibition of Cellular Proliferation and Migration Induced by miR-3189-3p (SEQ ID NO: 2): Since SF3B2 expression is strongly down-regulated by miR-3189-3p (SEQ ID NO: 2), it was possible that forced expression of SF3B2 might reverse the microRNA-mediated effects on cell proliferation. Results from growth rate analysis in FIG. 3A confirm this assumption. Moreover, constitutive expression of SF3B2 was enough to rescue cell growth to steady-state levels despite addition of miR-3189-3p (SEQ ID NO: 2). Conversely, down-regulation of SF3B2 by siRNA mimics the biological effects of miR-3189-3p (SEQ ID NO: 2) expression by inducing 55% reduction in cell growth (FIG. 3B). When tested on a migration assay, cells in which SF3B2 was silenced behaved essentially as the control cells, indicating that SF3B2 is involved in proliferation but not in migration of these cells.

The impaired growth by SF3B2 is likely mediated by E2F-1, a known molecule downstream of SF3B2 that is important for cell cycle progression (Orr et al., (2012) *Mol. Systems Biol.* 8: 573). The Western blot in FIG. 3E shows marked down-regulation of E2F-1 protein levels in LN-229 cells transfected with miR-3189-3p (SEQ ID NO: 2) and this effect was reversed in the presence of the anti-miR-3189-3p (SEQ ID NO: 22). Therefore, these data suggest that E2F-1 is a potential downstream target of miR-3189-3p (SEQ ID NO: 2)/SF3B2 in coordinating delayed cell growth.

Next, the contribution of p63RhoGEF to the inhibitory effects of miR-3189-3p (SEQ ID NO: 2) expression on cell migration was determined. Silencing p63RhoGEF in LN-229 resulted in 54% (±7%) inhibition of migration (FIG. 3D) confirming previously reported data (Orr et al., (2012) *Mol, Systems Biol.* 8: 573). To test the contribution of p63RhoGEF on the inhibition of migration due to miR-3189-3p (SEQ ID NO: 2), p63RhoGEF was over-expressed in LN-229 cells. When tested using the scratch assay, p63RhoGEF-expressing cells behaved essentially similar to the control cells (transfected with pcDNA3.1 empty vector); however transient transfection with the miR-3189-3p (SEQ ID NO: 2) was still capable of reducing cell migration by 60% (FIG. 3C). Knocking down p63RhoGEF did not alter proliferation of LN-229 cells. Altogether, those results indicate that down-regulation of SF3B2 by miR-3189-3p (SEQ ID NO: 2) is necessary and sufficient for the miR-mediated impairment of cell growth, while down-regulation of p63RhoGEF might be required but is not sufficient for the inhibition of migration by miR-3189-3p (SEQ ID NO: 2).

Example 19

MiR-3189-3p has Tumor Suppressor Activity in Mice: The ability of miR-3189-3p (SEQ ID NO: 2) to inhibit tumor growth in vivo was evaluated. LN-229 cells, bearing the pmCherry plasmid to facilitate detection of the tumor by fluorescence, were mock-transfected or transfected with miR-3189-3p (SEQ ID NO: 2) mimic. Next day, $2 \times 10^6$ of either transfected cells were injected subcutaneously in the flank of nude mice (n=5 per group). Beginning at one week post-injection, mice were visualized via in vivo biophotonic epifluorescence and the mean fluorescence radiance for each tumor was collected. Mice bearing LN-229/miR-3189-3p (SEQ ID NO: 2) cells had a nearly 75% smaller tumors when compared to LN-229/Mock (FIGS. 4A and 4B; p<0.05) or to cells expressing both miR-3189-3p (SEQ ID NO: 2) and its antago-miR.

The anti-tumor effect of miR-3189-3p (SEQ ID NO: 2) was also confirmed in nude mice bearing U87MG glioblastoma cells. In another experimental setting, U87MG cells bearing the luciferase gene were transfected with miR-3189-3p (SEQ ID NO: 2) prior to their intracranial injection in nude mice. Tumor growth was monitored using biophotonic epifluorescence as described above. Results in FIGS. 4C-4F show a strong inhibition of tumor growth in the animals bearing the cells transfected with the microRNA at both 15 and 22 d post-injection (FIGS. 4C-4D and 4E-4F, respectively). Indeed, more than 40 d after the control mice have died because of tumor growth, two of the animals injected with cells transfected with miR-3189-3p (SEQ ID NO: 2) never developed the tumor and were still alive.

FIG. 4G shows the survival data for the two groups of mice. All mice in the control group died because of the intracranial tumor growth. One mouse in the miR-3189-3p (SEQ ID NO: 2) group died after 21 d without apparent signs of tumor formation; two mice developed intracranial tumors and were sacrificed at day 31 and 36. Of note, the mouse that died after 36 d had a delay in developing the tumor, which was visible at day 29 but not at day 22 or 15 (FIG. 4E, mouse labeled with an asterisk). The delay in tumor formation may be attributable to the loss of cells bearing the microRNA over several d combined with the presence of some untransfected cells which later took over and formed the tumor. In fact, levels of miR-3189-3p (SEQ ID NO: 2) in this tumor were comparable to the controls, indicating loss of miR-3189-3p (SEQ ID NO: 2).

Since GDF15 and miR-3189 originate from the same transcript (FIG. 5A) and miR-3189-3p (SEQ ID NO: 2) is down-regulated in clinical samples, it was determined if GDF15 expression would also be down-regulated in human brain tumor extracts compared to controls. Results shown in FIGS. 5B-5D represent the relative expression (1/ΔCt) of the indicated RNA species normalized using GAPDH as reference gene. Interestingly, although GDF15 was not detected by real time PCR in normal brain tissues, its expression yielded a trend specific to tumor type with higher up-regulation in glioblastomas than in astrocytomas (FIG. 5B; p<0.05). These data may indicate that GDF15 and miR-3189 are differentially regulated and conditions or treatments that affect the expression of GDF15 may not alter expression of the microRNA. Of the two major targets of miR-3189-3p (SEQ ID NO: 2), SF3B2 and p63RhoGEF, only SF3B2 showed a statistically significant increase in expression in both astrocytomas and glioblastomas compared to the control group (p<0.01 and p<0.05, respectively) (FIG. 5C), while p63RhoGEF mRNA expression analysis did not result in significant changes between the three groups (FIG. 5D).

Example 20

Expression of GDF15 and miR-3189-3p (SEQ ID NO: 2) is Increased after Fenofibrate Treatment: Previous reports have demonstrated that GDF15 expression is induced following treatment by a variety of chemotherapeutic agents (Yoshioka et al., (2008) *J. Biol. Chem.* 283: 33129-33137; Shimizu et al., (2013) *Biochem. Biophys. Res. Comms.* 430: 1277-1282; Araki et al., (2009) *Angiogenesis* 12: 221-229). In line with these findings, it was reported that this gene is up-regulated in a microarray analysis of glioblastoma cells treated with the metabolically active anticancer compound, fenofibrate (Jeansonne et al., (2013) *Genes* 4: 46-64). Fenofibrate is a potent agonist of peroxisome proliferator activated receptor alpha (PPARα), which has exceptional anticancer properties, especially in tumors of neuroectodermal origin, including glioblastoma (Drukala et al., (2010) *Mol. Cancer* 9: 159; Wilk et al., (2014) *Mol. Cell Biol.* 35: 182-198; Wilk et al., (2012) *Cell Cycle* 11: 2660-2671).

To further analyze the effects of fenofibrate on this gene, the human glioblastoma cell lines, LN-229 and U87MG were exposed to 50 µM fenofibrate and monitored the expression of GDF15 at 24 and 48 h time points. Note that up to 48 h, cells treated with fenofibrate look normal and the toxic effect of fenofibrate is still reversible upon removal of the drug; however, the effects will become irreversible and the cells will die between 48 and 72 h (Wilk et al., (2014) *Mol. Cell Biol.* 35: 182-198). Following the treatment, total RNA was extracted and subjected to quantitative real-time PCR (qRT-PCR) using GDF15-specific and GAPDH-specific primers. The results in FIG. 6A show a 60- and 35-fold up-regulation of GDF15 gene expression in the two cell lines. In agreement with these findings, a large increase in GDF15 protein content was detected by Western blot, and significant levels of secreted GDF15 were detected by ELISA at 48 h following fenofibrate treatment in LN-229 cells (FIGS. 6 B and 6C, respectively).

The two-fold difference in the expression of GDF15 in the two cell lines was reflected also in the levels of miR-3189-3p (SEQ ID NO: 2), since the amount of this microRNA in LN-229 was two times more than in U87MG cells (FIG. 6D). Expression of miR-3189-5p (SEQ ID NO: 21) did not change in response to fenofibrate treatment in the cell lines tested. In addition to fenofibrate, it was determined whether treatment of glioblastoma cells with common chemotherapeutic agents would trigger up-regulation of GDF15 and miR-3189-3p (SEQ ID NO: 2). FIG. 6E shows results from quantitative PCR to detect GDF15 mRNA and miR-3189-3p (SEQ ID NO: 2) in LN-229 cells treated for 48 h with doxorubicin (Marrero et al., (2014) *Neoplasia* 16: 874-882), paclitaxel (mitotic inhibitor) and fenofibrate for 48 h. Relative expression compared to untreated cells indicates up-regulation of miR-3189-3p (SEQ ID NO: 2) only in fenofibrate treated cells, with 4.8-fold increase. GDF15 mRNA was also highly up-regulated by fenofibrate (more than 60 folds). This experiment confirms the specificity of the treatment and suggests an independent regulation of expression of GDF15 and miR-3189-3p (SEQ ID NO: 2).

Fenofibrate exerts its proapoptotic action in cancer cells through PPARα-dependent and -independent mechanisms Drukala et al., (2010) *Mol. Cancer* 9: 159; Wilk et al., (2014) *Mol. Cell Biol.* 35: 182-198; Wilk et al., (2012) *Cell Cycle* 11: 2660-2671) and, therefore, the contribution of an increased expression of miR-3189-3p (SEQ ID NO: 2) to the fenofibrate-mediated tumor cell toxicity could be difficult to determine. Indeed, treatment of LN-229 cells with anti-miR-3189-3p (SEQ ID NO: 22) did not rescue cells from fenofibrate-induced cells death. Yet, in the presence of fenofibrate miR-3189-3p (SEQ ID NO: 2) is functionally associated to Ago2 complexes, as determined by RNA-IP (FIG. 7B). Although endogenous levels of Ago2 were undetectable in LN-229 cells by Western blot, it was efficiently immunoprecipitated in all conditions tested (FIG. 7A). When compared to untreated cells, nearly 35-fold overexpression of miR-3189-3p (SEQ ID NO: 2) linked to Ago2 immunocomplexes was measured in extracts from FF-treated cells (FIG. 7B).

Finally, it was determined whether the fenofibrate-mediated increase in GDF15 and miR-3189-3p (SEQ ID NO: 2) was a PPARα-dependent event. PPARα activity was inhibited at the level of receptor by a specific ligand/inhibitor WY146,43 (Wilk et al., (2014) Mol. Cell Biol. 35: 182-198; Wilk et al., (2012) *Cell Cycle* 11: 2660-2671) or through its down-regulation via siRNAs. Total RNA was extracted 48 h after the treatment/transfection and levels of GDF15 and miR-3189-3p (SEQ ID NO: 2) were determined by quantitative PCRs. Results shown in FIGS. 7C and 7D, indicate no significant impact by either compounds on the levels of GDF15 and miR-3189-3p (SEQ ID NO: 2), since their expression triggered by fenofibrate was comparable to the controls. Although miR-3189-3p (SEQ ID NO: 2) expression showed a reproducible, moderate reduction in both experiments, this difference was not statistically significant. Efficacy of the siRNA to down-regulate PPARα was determined by RT-PCR and is included in FIG. 7D.

Example 21

Triple negative breast cancer (TNBC) is an aggressive subtype of breast cancer characterized by the lack of estrogen receptor, progesterone receptor, and HER-2. Consequently, TNBC cannot be treated by the available hormone therapies and receptor targeted treatments. MYC, a regulatory gene involved in cell growth, metabolism, differentiation, and apoptosis, is disproportionately overexpressed in many TNBCs, making it a valuable therapeutic target. MicroRNAs, small, non-coding RNA molecules involved in the regulation of gene expression, have been identified as key players in cancer pathogenesis; however, the specific microRNAs and pathways involved in TNBC are still largely unknown.

It has been found that MYC protein is down-regulated in these cancer cells following treatment with miR-3189-3p. Additional studies revealed that miR-3189-3p treatment resulted in a marked decrease in TNBC proliferation and migration.

What is claimed is:

1. A method for decreasing at least one of the proliferation and the migration of a glial tumor cell, comprising contacting the cancer cell with a pharmaceutically acceptable composition comprising a microRNA (miRNA) having the nucleotide sequence SEQ ID NO: 2, thereby decreasing at least one of the proliferation and migration of the cancer cell as compared to a control.

2. The method of claim 1, wherein the glial tumor cell is an astrocytoma tumor cell, an ependymal tumor cell, a glioblastoma multiforme tumor cell, or a primitive neuroectodermal tumor cell.

3. The method of claim 2, wherein the glioblastoma multiforme is located in the brain or the spinal cord of the subject.

4. The method of claim 1, wherein the miRNA reduces the expression of at least one of p63RoGEF and SF3B2 splicing factor in the cancer cell, or modulates the effect of MYC in the cancer cell.

5. The method of claim 1, wherein the cancer cell is an isolated cancer cell, a cultured cell, a cell in a tissue of an animal or human patient, or progeny thereof.

6. A method for treating a cancer, wherein the cancer is a glial tumor, the method comprising administering to an animal or human subject in need thereof an effective amount of a pharmaceutically acceptable composition consisting essentially of a microRNA (miRNA) having the nucleotide sequence SEQ ID NO: 2, thereby decreasing at least one of the proliferation and migration of the cancer cell as compared to a control.

7. The method of claim 6, wherein the glial tumor cell is an astrocytoma tumor cell, an ependymal tumor cell, a glioblastoma multiforme tumor cell, or a primitive neuroectodermal tumor cell.

8. The method of claim 6, wherein the glioblastoma multiforme is located in the brain or the spinal cord of the subject.

9. The method of claim 6, wherein the miRNA reduces the expression of at least one of p63RoGEF and SF3B2 splicing factor in the cancer cell, or modulates the effect of MYC in the cancer cell.

10. The method of claim 6, wherein the pharmaceutically acceptable composition is administered to the animal or human subject intravenously, subcutaneously, or intratumorally.

11. The method of claim 6, wherein the pharmaceutically acceptable composition is formulated to deliver the miRNA across the blood-brain barrier or to deliver the miRNA as a nucleic acid expression product to the cells of the cancer.

* * * * *